(12) United States Patent
Villiger-Oberbek et al.

(10) Patent No.: US 11,060,058 B2
(45) Date of Patent: Jul. 13, 2021

(54) PERFUSION CULTURING METHODS AND USES THEREOF

(71) Applicant: Genzyme Corporation, Cambridge, MA (US)

(72) Inventors: Agata Villiger-Oberbek, Cambridge, MA (US); Jianguo Yang, Sudbury, MA (US); Yang Yang, Hopkinton, MA (US); Gabrielle Lorenzo, West Seneca, NY (US)

(73) Assignee: Genzyme Corporation, Cambridge, MA (US)

( * ) Notice: Subject to any disclaimer, the term of this patent is extended or adjusted under 35 U.S.C. 154(b) by 286 days.

(21) Appl. No.: 14/732,325

(22) Filed: Jun. 5, 2015

(65) Prior Publication Data

US 2016/0017280 A1    Jan. 21, 2016

Related U.S. Application Data

(60) Provisional application No. 62/009,058, filed on Jun. 6, 2014.

(51) Int. Cl.
| | | |
|---|---|---|
| C12N 5/071 | (2010.01) | |
| C12P 21/00 | (2006.01) | |
| C12M 1/00 | (2006.01) | |
| C12M 1/32 | (2006.01) | |
| C12M 3/04 | (2006.01) | |

(52) U.S. Cl.
CPC .......... *C12N 5/0602* (2013.01); *C12M 23/12* (2013.01); *C12M 27/10* (2013.01); *C12M 29/10* (2013.01); *C12P 21/00* (2013.01); *C12N 2510/02* (2013.01); *C12N 2527/00* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppestein et al. | |
| 6,455,298 B1 | 9/2002 | Groner et al. | |
| 7,354,579 B2 | 4/2008 | Kakkis et al. | |
| 7,767,446 B2* | 8/2010 | Robbins | C12M 23/12 435/289.1 |
| 8,617,879 B2* | 12/2013 | Yu | C12M 29/10 435/283.1 |
| 9,909,101 B2 | 3/2018 | Yang et al. | |
| 10,421,949 B2 | 9/2019 | Yang et al. | |
| 10,421,987 B2* | 9/2019 | Huang | C12N 5/0018 |
| 2003/0096366 A1 | 5/2003 | Knudsen | |
| 2003/0113915 A1 | 6/2003 | Heidemann et al. | |
| 2005/0019914 A1 | 1/2005 | Staerk et al. | |
| 2005/0186669 A1 | 8/2005 | Ho et al. | |
| 2008/0199958 A1 | 8/2008 | Hui | |
| 2008/0206819 A1 | 8/2008 | Tsao et al. | |
| 2008/0274507 A1 | 11/2008 | Gomes et al. | |
| 2009/0042253 A1 | 2/2009 | Hiller et al. | |
| 2009/0233334 A1 | 9/2009 | Hildinger et al. | |
| 2010/0076380 A1 | 3/2010 | Hui | |
| 2011/0020929 A1 | 1/2011 | Schober et al. | |
| 2011/0212493 A1* | 9/2011 | Hirschel | C12M 23/28 435/91.4 |
| 2012/0164066 A1 | 6/2012 | Greene et al. | |
| 2013/0260419 A1 | 10/2013 | Ransohoff et al. | |
| 2014/0154726 A1 | 6/2014 | Yang et al. | |
| 2014/0255994 A1 | 9/2014 | Konstantinov et al. | |
| 2014/0273206 A1 | 9/2014 | Jin et al. | |
| 2015/0158907 A1 | 6/2015 | Zhou et al. | |
| 2015/0183821 A1 | 7/2015 | Konstantinov et al. | |
| 2015/0202595 A1 | 7/2015 | Godawat et al. | |
| 2015/0203529 A1 | 7/2015 | Godawat et al. | |
| 2015/0203531 A1 | 7/2015 | Godawat et al. | |
| 2015/0203532 A1 | 7/2015 | Godawat et al. | |
| 2015/0232505 A1 | 8/2015 | Konstantinov et al. | |
| 2015/0353896 A1 | 12/2015 | Bruninghaus et al. | |
| 2016/0002594 A1 | 1/2016 | Yang et al. | |
| 2016/0017280 A1 | 1/2016 | Villiger-Oberbek et al. | |
| 2016/0017291 A1 | 1/2016 | Yang et al. | |
| 2016/0177361 A1 | 6/2016 | Bae et al. | |

FOREIGN PATENT DOCUMENTS

| | | |
|---|---|---|
| CA | 2901940 | 8/2014 |
| CN | 1373799 | 10/2002 |
| CN | 1564863 | 1/2005 |
| CN | 101875917 | 11/2010 |
| CN | 201933090 | 11/2010 |
| CN | 104450597 | 3/2015 |
| CN | 104480897 | 4/2015 |
| EP | 1451290 | 9/2004 |
| EP | 1508576 | 2/2005 |
| EP | 2020433 | 2/2009 |
| EP | 2163640 | 3/2010 |

(Continued)

OTHER PUBLICATIONS

Corning-24, Corning Costar Ultra-low attachment multiwell plates, Sigma-Aldrich Catalog Webpage, Aug. 10, 2017.*

Huang et al., Maximizing Productivity of CHO Cell-Based Fed-Batch Culture Using Chemically Defined Media Conditions and Typical Manufacturing Equipment, American Institute of Chemical Engineers Biotechnol. Prog., 26: 1400-1410, 2010.*

Jayapal et al., Recombinant protein therapeutics form CHO cells—20 years and counting, CHO consortium, SBE special section, Chemical Engineering Progress, vol. 103, Issue 10, Oct. 2007, p. 40-47.*

Schirmer et al., Primary Clarification of Very High-Density Cell Culture Harvests By Enhanced Cell Settling, BioProcess International, Jan. 2010.*

(Continued)

*Primary Examiner* — Blaine Lankford
(74) *Attorney, Agent, or Firm* — Fish & Richardson P.C.

(57) ABSTRACT

Provided herein are methods of culturing a mammalian cell and various methods that utilize these culturing methods. Also provided are multi-well cell culture plates, e.g., for use in perfusion culturing methods.

18 Claims, 17 Drawing Sheets

(56) References Cited

FOREIGN PATENT DOCUMENTS

| | | |
|---|---|---|
| EP | 3152299 | 11/2019 |
| JP | 2010-519917 | 6/2010 |
| JP | 2011-072322 | 4/2011 |
| JP | 2013-520975 | 6/2013 |
| RU | 2058992 | 4/1996 |
| RU | 2215748 | 11/2003 |
| RU | 2380412 | 1/2010 |
| RU | 2016152238 | 7/2018 |
| WO | WO 2001/018175 | 3/2001 |
| WO | WO 02/050251 | 6/2002 |
| WO | WO 03/029442 | 4/2003 |
| WO | WO 2003/039459 | 5/2003 |
| WO | WO 2006/033935 | 3/2006 |
| WO | WO 2006/138143 | 12/2006 |
| WO | WO 06/039588 | 5/2007 |
| WO | WO 08/073620 | 6/2008 |
| WO | WO 2008/106515 | 9/2008 |
| WO | WO 08/127087 | 10/2008 |
| WO | WO 2009/023562 | 2/2009 |
| WO | WO 2009/034186 | 3/2009 |
| WO | WO 2012/098055 | 7/2012 |
| WO | WO 12/078677 | 8/2012 |
| WO | WO 2012/152945 | 11/2012 |
| WO | WO 2013/006479 | 1/2013 |
| WO | WO 2013/116449 | 8/2013 |
| WO | WO 2013/151616 | 10/2013 |
| WO | WO 2014/066519 | 5/2014 |
| WO | WO 2012/127523 | 7/2014 |
| WO | WO 2014/130864 | 8/2014 |
| WO | WO 2014/130872 | 8/2014 |
| WO | WO 14/137903 | 9/2014 |
| WO | WO 14/143691 | 9/2014 |
| WO | WO 15/039115 | 3/2015 |
| WO | WO 2015/095809 | 6/2015 |
| WO | WO 15/109146 | 7/2015 |
| WO | WO 15/109151 | 7/2015 |
| WO | WO 15/188009 | 12/2015 |
| WO | WO 15/188106 | 12/2015 |
| WO | WO 15/191462 | 12/2015 |
| WO | WO 16/106192 | 6/2016 |

OTHER PUBLICATIONS

Shevitz et al., An Economic Comparison of Three Cell Culture Techniques, BioPharm International, vol. 24, Issue 2, Feb. 1, 2011 (Year: 2011).*
Enzyscreen, Cultivation of CHO cells in microplates, Webpage, May 3, 2014 (Year: 2014).*
Klockner, Advances in shaking technologies, Trends in Biotechnology, Jun. 2012, vol. 30, No. 6 (Year: 2012).*
Tao et al., Development and Implementation of a Perfusion-Based High Cell Density Cell Banking Process, Biotechnology Progess, 27, p. 824-829, 2011 (Year: 2011).*
Quinlan et al., A Semicontinuous Culture Model that Links Cell Growth to Extracellular Nutrient Concentration, Biotechnology and Bioengineering, vol. XXVIII, pp. 1455-1461 (1986) (Year: 1986).*
GB-1ml, Greiner Bio 96 Well MASTERBLOCK 1ml, Catalog Webpage, 2020 (Year: 2020).*
GB-2ml, Greiner Bio 96 Well MASTERBLOCK 2ml, Catalog Webpage, 2020 (Year: 2020).*
U.S. Appl. No. 14/061,657, filed Oct. 23, 2013, Yang et al.
U.S. Appl. No. 14/769,772, filed Aug. 21, 2015, Yang et al.
U.S. Appl. No. 14/769,783, filed Aug. 21, 2015, Yang et al.
U.S. Appl. No. 14/976,486, filed Dec. 21, 2015, Bae et al.
U.S. Appl. No. 14/976,486, Bae et al., filed Dec. 21, 2016.
Barrett et al., "Microwell engineering characterization for mammalian cell culture process development," *Biotechnol Bioeng.*, 105(2):260-275, Feb. 1, 2010.
Chaturvedi et al., "Comparison of the behavior of CHO cells during cultivation in 24-square deep well microplates and conventional shake flask systems." *Biotechnology Reports.*, 1 (2014): 22-26.

Danielson et al., "Maximizing cell densities in miniprep-scale cultures with H15 medium and improved oxygen transfer," Biochemical Engineering J, 17:175-180, 2004.
Domansky et al., "Perfused multiwell plate for 3D liver tissue engineering," Lab on a Chip, 10(1):51-58 (Jan. 1, 2010).
Nam et al., "The effects of microcarrier culture on recombinant CHO cells under biphasic hypothermic culture conditions," *Cytotechnology*, 59(2):81-91, Epub May 2, 2009.
Rodrigues et al., "Technological progresses in monoclonal antibody production systems," *Biotechnol. Prog.*, 26(2):332-351, Mar.-Apr. 2010.
Scott, "Growth of mesenchymal stromal cells in automated microwell cultures: influence of the engineering environment on cell growth kinetics and non-directed differentiation," (Doctoral dissertation, UCL (University College London), 202 pages, Sep. 2008.
Silk et al., "Fed-batch operation of an industrial cell culture process in shaken microwells," *Biotechnol Lett.* 32(1):73-78, print Jan. 2010, Epub Sep. 17, 2009.
Strnad et al., "Optimization of cultivation conditions in spin tubes for Chinese hamster ovary cells producing erythropoietin and the comparison of glycosylation patterns in different cultivation vessels," Biotechnology Progress, 26(3):653-663 (2010).
Zhang et al., "A robust high-throughput sandwich cell-based drug screening platform," Biomaterials, 32(4):1229-124 (Feb. 1, 2011).
International Preliminary Report on Patentability for PCT/US2014/017785, dated Sep. 3, 2015, 8 pages.
International Preliminary Report on Patentability for PCT/US2014/017803, dated Sep. 3, 2015, 8 pages.
International Preliminary Report on Patentability in International Application No. PCT/US2013/066410, dated May 7, 2015, 8 pages.
International Search Report and Written Opinion for PCT/US2014/017785, dated May 20, 2014, 11 pages.
International Search Report and Written Opinion for PCT/US2014/017803, dated May 20, 2014, 11 pages.
International Search Report and Written Opinion in International Application No. PCT/US2015/034494, dated Nov. 30, 2015, 24 pages.
Invitation to Pay for PCT/US2015/034494, dated Aug. 12, 2015, 6 pages.
Notification of Transmittal of the International Search Report and the Written Opinion issued in PCT/US2013/066410 dated Jan. 31, 2014 (12 pages).
Non-final Office Action issued in U.S. Appl. No. 14/061,657 dated Nov. 5, 2015, 12 pages.
Chinese Office Action in Chinese Patent Application No. 201380067513.8, dated Apr. 13, 2016, 23 pages.
Chinese Office Action in Chinese Patent Application No. 2013-80067513.8, dated Dec. 29, 2016.
Clincke et al., "Very high density of CHO cells in perfusion by ATF or TFF in WAVE bioreactor. Part I. Effect of the cell density on the process," *Biotechnol. Prog.* 29(3):754-767, May 2013.
Communication in European Patent Application No. 13786587.9, dated Feb. 21, 2017, 4 pages.
Communication in European Patent Application No. 13786587.9, dated Mar. 15, 2016.
Communication in European Patent Application No. 14709829.7 dated Jun. 27, 2016.
Costa et al., "The impact of microcarrier culture optimization on the glycosylation profile of a monoclonal antibody," *Springer Plus* 2(25):1-10, Jan. 28, 2013.
De Jesus et al., "Tubespin Satellites: A fast track approach for process development with animal cells using shaking technology," *Biotechnol. Bioeng. J.* 17:217-223, Mar. 2004.
European Office Action in European Application No. 13786587.9, dated Sep. 27, 2016, 11 pages.
European Office Action in European Application No. 14709829.7, dated Jun. 27, 2016, 5 pages.
Fernandes-Platzgummer et al., Scale-up of mouse embryonic stem cell expansion in stirred bioreactors, American Institute Chemical Engineers, dated Sep./Oct. 2011vol. 27, Issue 5, pp. 1421-1432.
Gargi et al. "Development of a new bioprocess scheme using frozen seed train intermediates to initiate CHO cell culture manufacturing campaigns," *Biotech. Bioeng.* 110(5):1376-1385, May 4, 2013.

(56) References Cited

OTHER PUBLICATIONS

Gebauer and Skerra, "Engineered protein scaffolds as next-generation antibody therapeutics," *Curr. Opin. Chem. Biol.* 13(3):245-255, Jun. 2009.
International Preliminary Report on Patentability in Application No. PCT/US2013/066410, dated Apr. 28, 2015.
International Search Report and Written Opinion in International Application No. PCT/US2015/034709, dated Oct. 30, 2015, 13 pages.
International Search Report and Written Opinion in International Application No. PCT/US2015/067040, dated Sep. 5, 2016, 19 pages.
Katakam et al., "Effect of Surfactants on the physical stability of recombinant human growth hormone," *J. Pharm. Sciences* 84(6):713-716, Jun. 1, 1995.
Kim et al., "Batch, Fed-Batch and Microcarrier Cultures with CHO cell lines in a pressure-cycle driven miniturized bioreactor," *Biotechnol. Bioeng.* 109(1):137-145, Oct. 2011.
Non-final Office Action in U.S. Appl. No. 14/061,657 dated Aug. 19, 2016.
Non-final Office Action in U.S. Appl. No. 14/061,657 dated Nov. 5, 2015, 12 pages.
Non-final Office Action in U.S. Appl. No. 14/769,783, dated Nov. 3, 2016, 36 pages.
Non-final Office Action in U.S. Appl. No. 14/733,630 dated Nov. 15, 2016, 13 pages.
Non-final Office Action in U.S. Appl. No. 14/769,772, dated Dec. 6, 2016, 19 pages.
Pohlscheidt et al., "Optimizing capacity utilization by large scale 3000 L perfusion in seed train bioreactors," *Biotech. Prog.* 27(5):222-229, Jan. 1, 2012.
Rosario, "Growth of Msenchymal Stromal Cells in Automated Microwell Cultures, Influence of the Engineering Environment on Cell Growth Kinetics and Non-Directed Differentiation Thesis submitted for the degree of Doctor of Philpsphy", Sep. 1, 2008.
Senger et al., "Effect of shear stress on intrinsic CHO culture state and glycosylation of recombinant tissue-type plasminogen activator protein," *Biotechnology Progress* 19(4):1199-209, Jul.-Aug. 2003; Abstract only.
Smelko et al., "Performance of high intensity fed-batch mammalian cell cultures in disposable bioreactor systems," *Biotechnology Progress* 27(5):1358-1364, Sep. 2011.
Soyer et al., "Introducing shear stress in the study of bacterial adhesion," *J. Vis. Exp.* (55), e3241, Sep. 2011.
Tao et al., "Development and implementation of a perfusion-based high cell density cell banking process," *Biotechnol. Prog.* 27(3):824-829, May-Jun. 2011.
Tordahl et al., "Study of a perfusion process of Chinese hamster ovary cells by ATF filtration in bioreactor ovary cells by ATF filtration in bioreactor," Sep. 11, 2009.
Villiger-Oberbek, "Development and application of a high-throughput platform for perfusion-based cell culture processes," *J. Biotechnol.* 212:21-29, Oct. 2015.
Wright et al., "A novel seed-train process: using high-density cell banking, a disposable bioreactor, and perfusion technologies," *BioProcess Int.* Mar. 10, 2015 Supplement.
Written Opinion in Singapore Patent Application No. 11201503085V, dated Dec. 7, 2016, 9 pages.
Written Opinion in Singapore Patent Application No. 11201506339R, dated Jul. 21, 2016.
Written Opinion in Singapore Patent Application No. 11201506343Q, dated Jun. 27, 2016, 5 pages.
Yang et al., "Perfusion seed cultures improve biopharmaceutical fed-batch production capacity and product quality," *Biotech. Prog.* 30(3):616-625, May 1, 2014.
U.S. Appl. No. 62/095,734, filed Dec. 22, 2014, Bae et al.
Chinese Office Action in Application No. 2013-80067513.8, dated Dec. 29, 2017, 22 pages.
European Office Action in European Application No. 13786587.9, dated Feb. 20, 2017, 6 pages.
Fernandes-Platzgummer et al., Scale-up of mouse embryonic stem cell expansion in stirred bioreactors, American Institute Chemical Engineers, vol. 27, Issue 5, pp. 1421-1432, Sep./Oct. 2011.
International Preliminary Report on Patentability in International Application No. PCT/US2015/034494, dated Dec. 6, 2016, 14 pages.
Office Action in U.S. Appl. No. 14/769,772, dated Dec. 6, 2016, 19 pages.
Office Action Issued in U.S. Appl. No. 14/769,783, dated Nov. 3, 2016, 36 pages.
Qi Yizheng et al., Oxygen transfer reaction characteristics, Chemical Industry Press, Bioreaction Engineering, dated Jul. 31, 2004, pp. 134-139.
Shi et al., Expansion of Mouse Sertoli Cells on Microcarriers, Cell Proliferation, vol. 43, Issue 3, pp. 275-286, Jun. 2010.
Singapore Written Opinion in Application No. 11201503085V, dated Dec. 7, 2016, 9 pages.
Singapore Written Opinion in Application No. 11201610167W, dated Oct. 12, 2017, 7 pages.
Japanese Office Action in Application No. 2016-571259, dated Apr. 16, 2019, 6 pages.
Russian Office Action in Application No. 2016152238, dated Feb. 13, 2019, 10 pages.
Russian Office Action in Application No. 2016152238, dated May 30, 2019, 6 pages.
Singapore Written Opinion in Application No. 11201610167W, dated May 27, 2019, 5 pages.
Chinese Office Action in Application No. 201380067513.8, dated Jun. 6, 2017, 22 pages.
Chinese Office Action in Application No. 201480022715.5, dated Feb. 13, 2018, 43 pages.
Chinese Office Action in Application No. 201480022715.5, dated May 15, 2017, 66 pages.
Chinese Office Action in Application No. 2014-80022766.8, dated May 4, 2017, 21 pages.
Communication in European Office Action in European Application No. 14709829.7, dated Aug. 31, 2017, 3 pages.
Communication in European Office Action in European Application No. 15730933.7 dated Oct. 23, 2017, 2 pages.
European Office Action in Application No. 15731177.0, dated Jul. 12, 2018, 5 pages.
Final Office Action in U.S. Appl. No. 14/733,630, dated May 11, 2017, 14 pages.
Final Office Action in U.S. Appl. No. 14/769,772, dated May 9, 2017, 23 pages.
Final Office Action in U.S. Appl. No. 14/769,783, dated Mar. 28, 2017, 38 pages.
Huang et al., "Maximizing productivity of CHO cell-based fed-batch culture using chemically defined media conditions and typical manufacturing equipment," *Am. Institute Chem. Eng. Biotechnol. Prog.* 26:1400-1410, Sep. 2010.
Jayapal et al., "Recombinant Protein Therapeutics from CHO cells—20 years and counting," Chemical Engineering Progress 103(10):40-47, Oct. 2007.
Kirti et al., "Comparison of the behavior of CHO cells during cultivation in 24-square deep well microplates and conventional shake flask systems," *Biotechnology Reports* 1-2:22-26, dated Jun. 2014.
Non-Final Office Action issued in U.S. Appl. No. 14/769,783, dated Oct. 10, 2017, 23 pages.
Non-final Office Action issued in U.S. Appl. No. 14/061,657 dated Nov. 24, 2017, 9 pages.
Schirmer et al., "Primary clarification of very high density cell culture harvests by enhanced cell settling," *BioProcress International*, pp. 32-39, Jan. 2010.
Written Opinion in Australian Patent Application No. 2013334602, dated May 23, 2017, 2 pages.
Written Opinion in Singapore Patent Application No. 11201506339R, dated Jul. 20, 2017, 5 pages.
Written Opinion in Singapore Patent Application No. 11201506343Q, dated Jul. 13, 2017, 5 pages.
Written Opinion in Singapore Patent Application No. 11201610216U, dated Oct. 11, 2017, 6 pages.

(56) References Cited

OTHER PUBLICATIONS

Israel Office Action in Application No. 249384, dated Dec. 18, 2018, 12 pages.
Brazil Office Action in Patent Application No. BR112016028512-3, dated Nov. 23, 2019, 9 pages.
Chinese Search Report in Patent Application No. 201580042017.6, dated Aug. 2, 2019, 2 pages.
Israel Office Action in Patent Application No. 249384, dated Dec. 8, 2019, 4 pages.
Japanese Office Action in Patent Application No. 2016-571259, dated Jan. 28, 2020, 9 pages.
Communication in European Office Action in Patent Application No. 15731177.0, dated Mar. 23, 2020, 10 pages.
Canadian Office Action in Patent Application No. 2,889,022, dated Dec. 30, 2020, 3 pages.
Australian Office Action in Patent Application No. 201569184, dated Aug. 12, 2020, 6 pages.
Chinese Office Action in Patent Application No. 201580042017.6, dated Jun. 12, 2020, 16 pages.
India Office Action in Patent Application No. 201737000152, dated Jun. 22, 2020, 10 pages.
Mexican Office Action in Patent Application No. MX/a/2016/016142, dated Mar. 11, 2020, 7 pages.
Russian Office Action in Patent Application No. 2019138327, dated Apr. 1, 2020, 5 pages.
U.S. Appl. No. 14/195,481, Konstantinov et al., filed Mar. 3, 2014.
U.S. Appl. No. 14/212,607, Jin et al., filed Mar. 14, 2014.
U.S. Appl. No. 62/009,553, Bruninghaus et al., filed Jun. 9, 2014.
Abu-Absi et al., "Cell Culture Process Operations for Recombinant Protein Production," Adv Biochem Eng Biotechnol, Oct. 24, 2013, 139: 35-68.
Abu-Absi, "Mammalian Cell Cultures for Biologics," Advances in Biochemical Engineering/Biotechnology, Oct. 24, 2013, Confirmation about date of publication, 25 pages.
Adams et al., "Increasing efficiency in protein supply and cell production by combining single-use bioreactor technology and perfusion," BioPharm International, May 2, 2011, pp. 4-11.
Australian Office Action in Patent Application No. 2014218715, dated Nov. 27, 2019, 3 pages.
Australian Office Action in Patent Application No. 201334602, dated May 23, 2017, 2 pages.
Australian Office Action in Patent Application No. 2014218723, dated Mar. 15, 2019, 3 pages.
Australian Office Action in Patent Application No. 2018222985, dated May 22, 2020, 7 pages.
Banik et al., "An investigation of cell density effects on hybridoma metabolism in a homogeneous perfusion reactor," Bioprocess Engineering, 1994, vol. 11: 229-237.
Birch et al., "Antibody production," Advanced Drug Delivery, 2006, vol. 58, pp. 671-685.
Boedeker, "Recombinant factor VIII (Kogenate®) for the treatment of hemophilia A: The first and only world-wide licensed recombinant protein produced in high-throughput perfusion culture," Modern Biopharmaceuticals: Recent Success Stories, First Edition, Apr. 2013, pp. 429-443.
Bonham-Carter et al., "A brief history of perfusion biomanufacturing: How high-concentration cultures will characterize the factory of the future," Bioprocess International, Oct. 2011, 9(9):24-30.
Brazilian Office Action in Application No. BR112016028891-2, dated Dec. 3, 2019, 5 pages.
Canadian Office Action in Patent Application No. 2,889,022, dated Oct. 24, 2019, 5 pages.
Canadian Office Action in Patent Application No. 2,901,940, dated Dec. 12, 2019, 4 pages.
Canadian Office Action in Patent Application No. 2901950, dated Dec. 4, 2019, 3 pages.
Castilho, "Continuous Animal Cell Perfusion Processes: The First Step Toward Integrated Continuous Biomanufacturing", Continuous Processing in Pharmaceutical Manufacturing, Dec. 5, 2014, Chapter 6.
Castilho, "Continuous Animal Cell Perfusion Processes: The First Step Toward Integrated Continuous Biomanufacturing," Continuous Processing in Pharmaceutical Manufacturing, Dec. 5, 2014, Confirmation about date of publication, 3 pages.
Chinese Office Action in Chinese Patent Application No. 201810153403.8, dated Nov. 4, 2020, 18 pages.
Chinese Office Action in Patent Application No. 201480022715.5, dated Aug. 31, 2018, 69 pages.
Chinese Office Action in Patent Application No. 201480022715.5, dated Feb. 13, 2018, 53 pages.
Chinese Office Action in Patent Application No. 201480022715.5, dated Jul. 21, 2020, 44 pages.
Chinese Office Action in Patent Application No. 201480022766.8, dated Jan. 3, 2018, 7 pages.
Chinese Office Action in Patent Application No. 201480022766.8, dated Jan. 9, 2019, 23 pages.
Chinese Office Action in Patent Application No. 201480022766.8, dated Jun. 5, 2019, 28 pages.
Chinese Office Action in Patent Application No. 201580042488.7, dated Feb. 7, 2020, 8 pages.
Chinese Office Action in Patent Application No. 201580042488.7. dated Feb. 11, 2019, 2 pages.
Chinese Office Action in Patent Application No. 201580042488.7. dated Oct. 8, 2019, 7 pages.
Chmiel, "Kultivierung von Saugerzellen," BioProzesstechnik, 2011, Chapter 11, 57 pages.
Chotteau, "Perfusion Processes," Animal Cell Culture, 2015, Chapter 13, 38 pages.
Chotteau, "Perfusion Processes," Confirmation of Publication, Animal Cell Culture, 2015, Chapter 13, 38 pages.
Clincke et al., "Very high density of Chinese hamster ovary cells in perfusion by alternating tangential flow or tangential flow filtration in WAVE Bioreactor™, Part II: Applications for antibody production and Cryopreservation," Biotechnol. Prag., May 2013, 29(3):768-777.
coleparmer.com [online], "Corning 4500-1L ProCulture Spinner Flask, 1000 mL; 1/Pk from Cole-Parmer", 2018, retrieved on Mar. 12, 2018, retrieved from URL: <https://www.coleparmer.com/i/mn/0183706>, 2 pages.
Communication in European Patent Application No. 13786587.9, dated Sep. 27, 2016, 11 pages.
Communication in European Patent Application No. 14709106.0, dated Dec. 6, 2018, 8 pages.
Communication in European Patent Application No. 14709106.0, dated Jul. 1, 2019, 4 pages.
Communication in European Patent Application No. 14709106.0, dated Mar. 30, 2020, 7 pages.
Communication in European Patent Application No. 14709106.0, dated Oct. 17, 2017, 5 pages.
Communication in European Patent Application No. 14709829.7, dated Aug. 31, 2017, 5 pages.
Communication in European Patent Application No. 14709829.7, dated Jun. 27, 2016, 5 pages.
Communication in European Patent Application No. 18205923.8, dated Apr. 23, 2020, 6 pages.
Communication in European in Patent Application No. 19209942.2, dated Jan. 14, 2020, 10 pages.
Duvar et al., "Developing an upstream process for a monoclonal antibody including medium optimization," BMC Proceedings, Jun. 2013, 7(Suppl. 6):34.
Ecker et al., "Mammalian cell culture capacity for biopharmaceutical manufacturing," Adv. Bicochem. Eng. Biotechnol., Jun. 2013, 139:185-225.
Environmental Protection Agency, "Integrated Pollution Prevention and Control Licensing," Application Form, Office of Licensing & Guidance, Jan. 20, 2006, 81 pages.
Environmental Protection Agency, "Integrated Pollution Prevention and Control Licensing," Proof of Publication, Office of Licensing & Guidance, Jan. 20, 2006, 2 pages.
Eriksson et al., "The manufacturing process for B-domain deleted Recombinant Factor VI 11," Seminars in Hematology, Apr. 2001, 38(2):24-31, Suppl. 4.

(56) References Cited

OTHER PUBLICATIONS

European Opposition in Patent Application No. 15730933.7, dated Aug. 19, 2020, 2020, 29 pages.
European Opposition in Patent Application No. 15730933.7, dated Aug. 25, 2020, 35 pages.
European Opposition in Patent Application No. 15730933.7, dated Aug. 26, 2020, 94 pages.
Examination Report in Singapore Patent Application No. 11201506339R, dated Jul. 13, 2017, 7 pages.
Examination Report in Singapore Patent Application No. 11201506339R, dated Jul. 21, 2016.
Examination Report in Singapore Patent Application No. 11201506343Q, dated Jun. 27, 2016, 5 pages.
Examination Report in Singapore Patent Application No. 11201506339R, dated Mar. 26, 2019, 5 pages.
Examination Report in Singapore Patent Application No. 1120160167W, dated Jun. 23, 2020, 6 pages.
Examination Report in Singapore Patent Application No. 11201506339R, dated Jul. 21, 2016, 5 pages.
Examination Report in Singapore Patent Application No. 11201610216U, dated Nov. 10, 2017, 6 pages.
Extended European Search Report in Application No. 18205923.8, dated Jan. 14, 2019, 9 pages.
Extended European Search Report in Application No. 20188132.3, dated Oct. 1, 2020, 9 pages.
Fenge et al., "Cell Culture Bioreactors," Cell Culture Technology for Pharmaceutical and Cell-Based Therapies, 2006, Chapter 6.
Final Office Action in U.S. Appl. No. 14/733,630, dated Feb. 7, 2019, 8 pages.
Final Office Action issued in U.S. Appl. No. 14/061,657, dated Aug. 19, 2016, 14 pages.
Final Office Action issued in U.S. Appl. No. 14/061,657, dated Jun. 18, 2018, 10 pages.
GE Healthcare Life Sciences, "Highly efficient inoculum propagation in perfusion culture using WAVE Bioreactor system," Application Note, 2012.
Gorfien et al., "Recombinant Protein Production by CHO Cells Cultured in a Chemically Defined Medium," Animal Cell Technology: Basic & Applied Aspects, 1998, pp. 247-252.
Griffiths et al., "Mammalian Cell Culture Reactors, Scale-Up", Encyclopedia of Bioprocess Technology: Fermentation, Biocatalysis, and Bioseparation, 1999, pp. 1594-1607.
Gupta et al., "Optimization of agitation speed in spinner flask for microcarrier structural integrity and expansion of induced pluripotent stem cells", Cytotechnology, 2014, 15 pages.
Hecht et al., "Efficiency improvement of an antibody production process by increasing the inoculum density," Biotechnol. Prag., Feb. 2014, 30(3):607-615.
Heidemann et al., "A new seed-train expansion method for recombinant mammalian cell lines," Cytotechnology, 2002, vol. 38, pp. 99-108.
Henry et al., "Simpler Noninstrumented Batch and Semicontinuous Cultures Provide Mammalian Cell Kinetic Data Comparable to Continuous and Perfusion Cultures," Biotechnology Progress, Jul. 2008, 24(4):921-931.
Indian Examination Report in Patent Application No. 2763/KOLNP/2015, dated May 15, 2020, 11 pages.
Israeli Office Action in Patent Application No. 249452, dated Nov. 15, 2018, 7 pages.
Israeli Office Action in Patent Application No. 249452, dated Dec. 1, 2019, 8 pages.
Japanese Office Action in Patent Application No. 2016-571259, dated Oct. 6, 2020, 8 pages.
Japanese Office Action in Patent Application No. 2016-572251, dated Jan. 7, 2020, 5 pages.
Kaisermayer et al., "Highly efficient inoculum propagation in perfusion culture using WAVE BioreactorTM systems," BMC Proceedings, Dec. 2013, 7(Suppl 6):P7.
Kantardjieff et al., "Mammalian cell cultures for biologics manufacturing," Mammalian Cell Cultures for Biologics Manufacturing, 2013, 18 pages.
Kloth et al., "Inoculum Expansion Methods, Recombinant Mammalian Cell Lines", Encyclopedia of Industrial Biotechnology: Bioprocess, Bioseparation, and Cell Technology, 2010, pp. 2988-3000.
Kompala et al., "Optimization of high cell density perfusion bioreactors", Cell Culture Technology for Pharmaceutical and Cell-Based Therapies, 2006, Chapter 11.
Konstantinov, "Developing an integrated Continuous Bioprocessing Platform", BioProcess Int., Dec. 1, 2012, 6 pages.
Kshirsagar et al., "Controlling Trisulfide Modification in Recombinant Monoclonal Antibody Produced in Fed-Batch Cell Culture", Biotechnology and Bioengineering, 2012, 109(10): 2523-2532.
Langer, "Trends in perfusion bioreactors—the next revolution in bioprocessing?" BioProcess International, Nov. 2011, 9(10):18-22.
Loffelholz et al., "Dynamic single-use bioreactors used in modern liter and m3-scale biotechnological processes: Engineering characteristics and scaling up," Adv. Biochem. Eng. Biotechnol., Apr. 2013, 138:1-44.
Mexican Office Action in Patent Application No. MX/a/2015/005206, dated Aug. 24, 2018, 6 pages.
Mexican Office Action in Patent Application No. MX/a/2015/005206, dated May 28, 2018, 6 pages.
Mexican Office Action in Patent Application No. MX/a/2015/010941, dated Feb. 1, 2019, 9 pages.
Mexican Office Action in Patent Application No. MX/a/2015/010941, dated Nov. 20, 2018, 6 pages.
Mexican Office Action in Patent Application No. MX/a/2015/010943, dated Jun. 4, 2019, 9 pages.
Mexican Office Action in Patent Application No. MX/a/2016/016301, dated Feb. 17, 2020, 6 pages.
Mexican Office Action in Patent Application No. MX/a/2016/016301, dated Oct. 30, 2018.
Mexican Office Action in Patent Application No. MX/a/2019/003638, dated Jul. 27, 2020, 9 pages.
Mexican Office Action in Patent Application No. MX/a/2019/009189, dated Jul. 27, 2020, 7 pages.
Michiels, "Response to Communication," Apr. 11, 2019, 6 pages.
Nelson, "Facility Design", Cell Culture Technology for Pharmaceutical and Cell-Based Therapies, 2006, Chapter 16, 51 pages.
New Webster's Dictionary, "Dispose", 1975, pp. 452-453.
Non-Final Office Action in U.S. Appl. No. 14/769,783 dated Oct. 1, 2018, 32 pages.
Non-Final Office Action in U.S. Appl. No. 15/874,645, dated Jul. 1, 2019, 7 pages.
Non-Final Office Action issued in U.S. Appl. No. 14/061,657, dated May 4, 2020, 23 pages.
Non-Final Office Action issued in U.S. Appl. No. 14/733,630, dated Feb. 21, 2018, 6 pages.
Non-Final Office Action issued in U.S. Appl. No. 14/733,630, dated Nov. 15, 2016, 13 pages.
Non-Final Office Action issued in U.S. Appl. No. 14/769,772, dated Dec. 6, 2016, 19 pages.
Non-Final Office Action Issued in U.S. Appl. No. 14/769,783, dated Nov. 3, 2016, 31 pages.
Ohashi et al., "Perfusion cell culture in disposable bioreactors," Animal Cell Technology: From Target to Market, 2001, pp. 403-409.
Ongena et al., "Determining Cell Number During Cell Culture using the Scepter Cell Counter", JOVE, 2010, 45(e2204): 1-5.
Oosterhuis et al., "Single-use bioreactors for microbial cultivation," Pharmaceutical Bioprocessing, 2013, 1(2):167-177.
Ozturk, "Equipment for large-scale mammalian cell culture," Adv. Biochem. Eng. Biotechnol., Sep. 5, 2013, 139:69-92.
Ozturk, "Equipment for large-scale mammalian cell culture," Confirmation about date of publication, Advances in Biochemical Engineering/Biotechnology, Jan. 1, 2014, 2 pages.
Padawer et al., "Case Study: an accelerated 8-day monoclonal antibody production process based on high seeding densities", Biotechnol Prog., 2013, 29(3): 829-832.

(56) References Cited

OTHER PUBLICATIONS

Pollock et al., "Fed-batch and perfusion culture processes: Economic, environmental, and operational feasibility under uncertainty," Biotechnology and Bioengineering, Jan. 2013, 110(1):206-219.
Raja et al., "Challenges in scaling up a perfusion process", BMC Proceedings, 2011, vol. 5, Suppliment 8, p. P122.
Russian Office Action in Patent Application No. 2016151316, dated Nov. 14, 2018.
Russian Office Action in Patent Application No. 2016152238, dated Feb. 13, 2019, 10 pages.
Russian Office Action in Patent Application No. 2016152238, dated Oct. 1, 2019, 14 pages.
Russian Office Action in Patent Application No. 2019138327, dated Jul. 22, 2020, 13 pages.
Senger et al., "Effect of shear stress on intrinsic CHO culture state and glycosylation of recombinant tissue-type plasminogen activator protein," Biotechnology Progress, Jul.-Aug. 2003, 19(4): 1199-1209.
Seth et al., "Development of a New Bioprocess Scheme Using Frozen Seed Train Intermediates to Initiate CHO Cell Culture Manufacturing Campaigns", Biotechnology and Bioengineering, 2012, 110(5): 1376-1385.
Soyer et al., "Introducing shear stress in the study of bacterial adhesion," J. Vis. Exp., Sep. 2011, (55):e3241.
Su, "Bioreactors, perfusion", Encyclopedia of Industrial Biotechnology: Bioprocess, Bioseparation, and Cell Technology, 2009, pp. 1-16.
Taiwan Office Action in Patent Application No. 104118071, dated Sep. 30, 2020, 15 pages.
Taiwan Office Action in Patent Application No. 104118240, dated Feb. 17, 2020, 1 page.
Tang et al., "Perfusion Culture of Hybridoma Cells for Hyperproduction of IgG2a Monoclonal Antibody in a Wave Bioreactor-Perfusion Culture System", 2007, vol. 23, pp. 255-264.
Technical specification of Vi-Cell XR Cell Viability Analyzer, 2010.
Technical specifications of CHO-S Cells by Invitrogen, Jan. 2003.
TPP, TPP centrifuge tubes, Sigma Aldrich Catalog, 2020, 3 pages.
Voisard et al., "Potential of cell retention techniques for large-scale high-density perfusion culture of suspended mammalian cells," Biotechnology and Bioengineering, Jun. 2003, 82(7):751-756.
Warikoo et al., "Integrated continuous production of recombinant therapeutic proteins," Biotechnology and Bioengineering, Dec. 2012, 109(12):3018-3029.
Wave Bioreactor™ 500/1000 System, GE Healthcare Life Sciences data sheet, 2012.
Werner et al., "Innovative, non-stirred bioreactors in scales from milliliters up to 1000 liters for suspension cultures of cells using disposable bags and containers—A Swiss contribution," Chimia, 2010, 64(11):819-823.
Wurm, "Production of recombinant protein therapeutics in cultivated mammalian cells", Nature Biotechnology, 2004, 22(11): 1393-1398.
Yang et al., "Development and application of perfusion culture producing seed cells in WAVE™ bioreactor," Chinese Journal of Biotechnology, Mar. 25, 2012, (28)3:358-367 (with English translation).
Yang et al., "Perfusion seed cultures improve biopharmaceutical fed-batch production capacity and product quality," Biotechnol Prog., May 1, 2014, 30(3):616-625.
Yizheng et al., "Oxygen transfer reaction characteristics," Chemical Industry Press, Bioreaction Engineering, Jul. 31, 2004, pp. 134-139.
Zhang et al., "A robust high-throughput sandwich cell-based drug screening platform," Biomaterials, Feb. 1, 2011, 32(4):1229-1241.
Australian Office Action in Patent Application No. 2015274897, dated Oct. 9, 2020, 5 pages.
Chinese Office Action in Patent Application No. 201480022715.5, dated Jan. 6, 2021, 109 pages.
Mexican Office Action in Application No. MX/a/2016/016142, dated Dec. 14, 2020, 10 pages.

\* cited by examiner

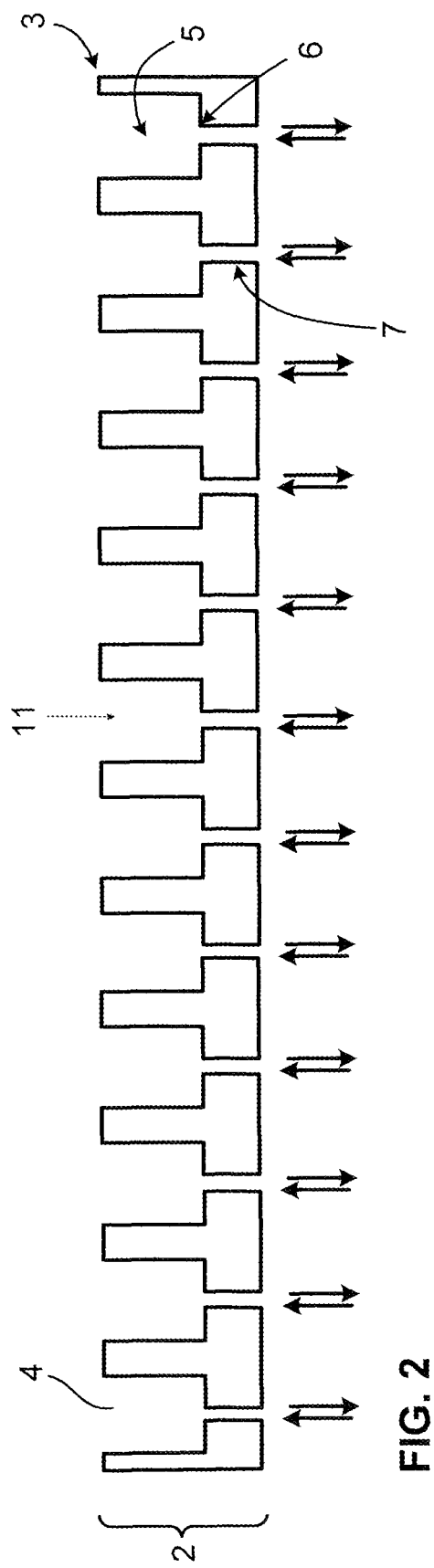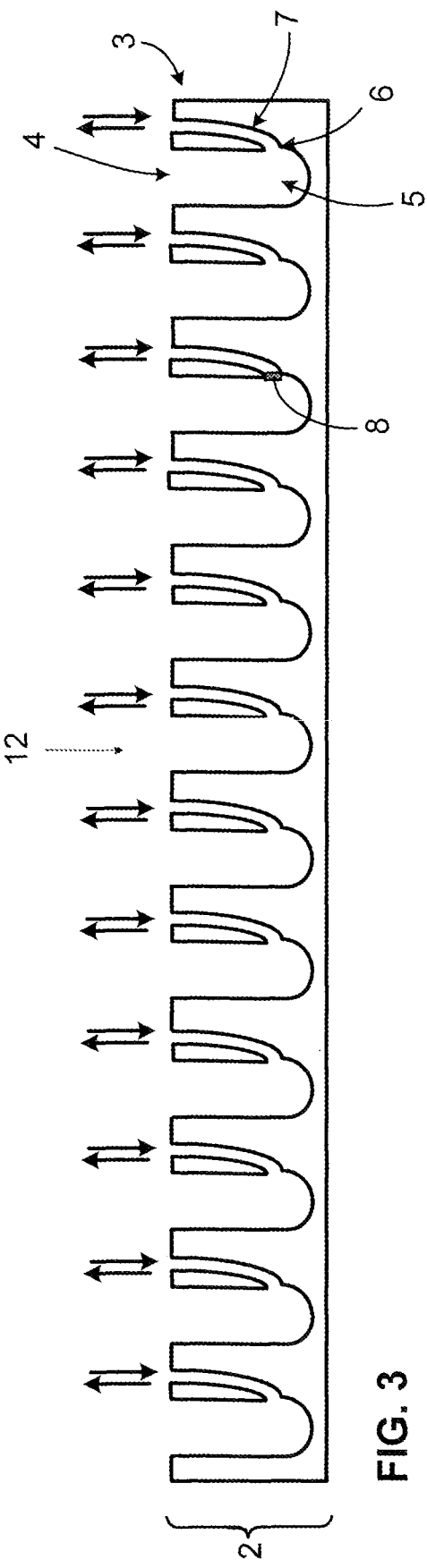

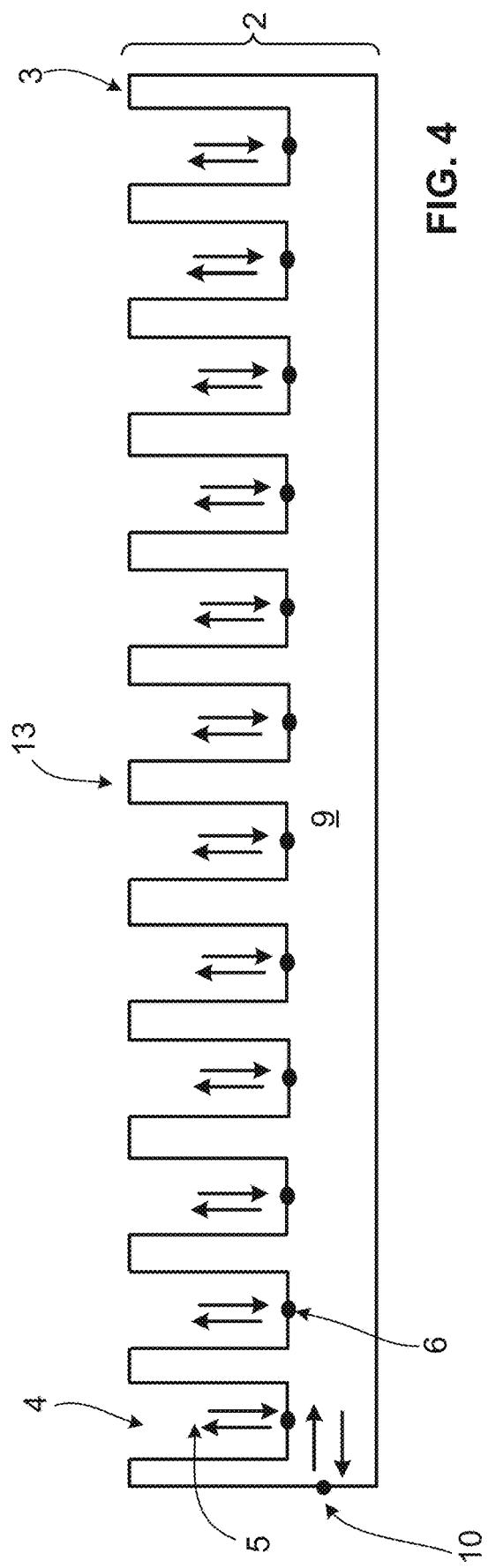

PERFUSION CULTURING METHODS AND USES THEREOF

CROSS-REFERENCE TO RELATED APPLICATIONS

This application claims priority to U.S. Provisional Patent Application Ser. No. 62/009,058, filed Jun. 6, 2014; the entire contents of which are herein incorporated by reference.

TECHNICAL FIELD

This invention relates to methods of molecular biology, cell culture process development, and the manufacture of recombinant proteins.

BACKGROUND

Mammalian cells containing a nucleic acid that encodes a recombinant protein are often used to produce therapeutically or commercially important proteins. Although several high throughput (HT) cell culture systems have been used within the biotechnology industry for fed-batch processes for years, no HT model for a perfusion-based cell culture using a multi-well plate is known to exist.

SUMMARY

The present invention is based, at least in part, on the discovery that culturing a mammalian cell in a multi-well plate in the specific manner described herein results in a substantially improved viable cell density and recombinant protein production, and provides an accurate model of culture performance in large-scale perfusion, production bioreactors. In view of this discovery, provided herein are methods culturing a mammalian cell, methods of producing a recombinant protein, and methods for testing a manufacturing process for making a recombinant protein. Also provided are multi-well cell culture plate systems that can be used, e.g., to perform any of the methods described herein.

Provided herein are methods of culturing a mammalian cell that include: providing a multi-well plate including at least one well containing a mammalian cell disposed in a first liquid culture medium, where the first liquid culture medium occupies about 5% to about 70% of the volume of the well; incubating the multi-well plate for a period of time at about 31° C. to about 40° C. and with a rotary agitation of about 320 revolutions per minute (RPM) to about 500 RPM; and continuously or periodically, during the period of time, removing a first volume of the first liquid culture medium and adding to the first liquid culture medium a second volume of a second liquid culture medium, wherein the first and second volumes are about equal. In some embodiments of these methods, the mammalian cell is a Chinese hamster ovary (CHO) cell. In some embodiments of these methods, the CHO cell contains a nucleic acid encoding a recombinant protein (e.g., an immunoglobulin, an enzyme, a growth factor, a protein fragment, or an engineered protein).

Also provided are methods of producing a recombinant protein that include: providing a multi-well plate including at least one well containing a mammalian cell disposed in a first liquid culture medium, where the first liquid culture medium occupies about 5% to about 70% of the volume of the well and the mammalian cell contains nucleic acid that encodes a recombinant protein; incubating the multi-well plate for a period of time at about 31° C. to about 40° C. and with a rotary agitation of about 320 revolutions per minute (RPM) to about 500 RPM; continuously or periodically, during the period of time, removing a first volume of the first liquid culture medium and adding to the first liquid culture medium a second volume of a second liquid culture medium, wherein the first and second volumes are about equal; and recovering the recombinant protein from the mammalian cell or from the first or second culture medium. In some embodiments of these methods, the recombinant protein (e.g., an immunoglobulin, an enzyme, a growth factor, a protein fragment, or an engineered protein) is recovered from the mammalian cell. In some embodiments of these methods, the recombinant protein (e.g., a secreted immunoglobulin, a secreted enzyme, a secreted growth factor, a secreted protein fragment, or a secreted engineered protein) is recovered from the first or second liquid culture medium.

Also provided are methods for testing a manufacturing process for making a recombinant protein that include: providing a multi-well plate including at least one well containing a mammalian cell disposed in a first liquid culture medium, where the first liquid culture medium occupies about 5% to about 70% of the volume of the well and the mammalian cell contains a nucleic acid that encodes a recombinant protein; incubating the multi-well plate for a period of time at about 31° C. to about 40° C. and with a rotary agitation of about 320 revolutions per minute (RPM) to about 500 RPM; continuously or periodically, during the period of time, removing a first volume of the first liquid culture medium and adding to the first liquid culture medium a second volume of a second liquid culture medium, wherein the first and second volumes are about equal; detecting the recombinant protein in the mammalian cell or in the first or second liquid culture medium; and comparing the amount of recombinant protein present in the mammalian cell or in the first or second liquid culture medium to a reference level of recombinant protein. In some embodiments of these methods, the reference level of recombinant protein is a level of recombinant protein produced using a different culturing method. In some embodiments of these methods, the different culturing method utilizes a different first or second liquid culture medium, a different mammalian cell, a different temperature, a different level of agitation, or a different multi-well plate. In some embodiments of these methods, the different culturing method utilizes different raw materials, anti-clumping agents, or chemically-defined liquid culture media. In some embodiments, these methods can be used, e.g., to perform high throughput cell culture experiments to perform a design-of-experiment (DOE) or a quality-by-design (QDB) study. In some embodiments of these methods, the recombinant protein (e.g., a secreted immunoglobulin, a secreted enzyme, a secreted growth factor, a secreted protein fragment, or a secreted engineered protein) is detected in the first or second liquid culture medium. In some embodiments of these methods, the recombinant protein (e.g., an immunoglobulin, an enzyme, a growth factor, a protein fragment, or an engineered protein) is detected in the cell.

In some embodiments of any of the methods described herein, the first volume of the first liquid culture medium is substantially free of mammalian cells. In some embodiments of any of the methods described herein, the first liquid culture medium occupies about 10% to about 60% of the volume of the well. In some embodiments of any of the methods described herein, the mammalian cell is a Chinese hamster ovary (CHO) cell. In some embodiments of any of the methods described herein, the rotary agitation is about 320 RPM to about 400 RPM. In any of the methods described herein the removing of the first volume of the first liquid culture medium and the adding of the second volume of the second liquid culture medium is performed simultaneously. In any of the methods described herein, the removing of the first volume of the first liquid culture medium and the adding of the second volume of the second liquid culture medium is performed continuously or periodically. In some embodiments of any of the methods described herein, the first volume of the first liquid culture medium removed and the second volume of the second liquid culture medium added are increased over time.

In some embodiments of any of the methods described herein, the multi-well plate is incubated for a period of time greater than 7 days, and on days 1 through 3 of incubation, in each 24-hour period, the first volume of the first liquid culture medium removed and the second volume of the second liquid culture medium added is between about 30% to about 50% of the volume of the first liquid culture medium; on days 4 through 6 of the incubation, in each 24-hour period, the first volume of the first liquid culture medium removed and the second volume of the second liquid culture medium added is between about 40% and about 70% of the volume of the first liquid culture medium; and on day 7 and onwards of incubation, in each 24-hour period, the first volume of the first liquid culture medium removed and the second volume of the second liquid culture medium added is about 90% to about 150% of the volume of the first liquid culture medium. In some embodiments of any of the methods described herein, the well has a volume of between about 1 mL to about 18 mL (e.g., between about 1 mL and about 7 mL or between about 1 mL and about 3.5 mL). In some embodiments of any of the methods described herein, the multi-well plate is a 6-well plate, a 12-well plate, a 24-well plate, a 48-well plate, or a 96-well plate. In some embodiments of any of the methods described herein, the multi-well plate is a deep-well plate. In some embodiments of any of the methods described herein, the diameter of the bottom of the well is between about 6.0 mm and about 35 mm (e.g., about 12 mm to about 50 mm). In some embodiments of any of the methods described herein, the height of the well is about 12 mm to about 50 mm. In some embodiments of any of the methods described herein, the mammalian cell is suspended in about 150 µL to about 15 mL (e.g., about 150 µL to about 10 mL, about 150 µL to about 5 mL, or about 150 µL to about 150 µL) of the first culture medium.

In some embodiments of any of the methods described herein, the first liquid culture medium and/or second liquid culture medium is selected from the group consisting of: a chemically-defined liquid culture medium, a serum-free liquid culture medium, a serum-containing liquid culture medium, an animal-derived component free liquid culture medium, and a protein-free medium. In some embodiments of any of the methods described herein, after about the first 24 to 48 hours of the period of time, in each 24-hour period, the first volume of the first liquid culture medium removed and the second volume of the second liquid culture medium added is about 30% to about 150% of the volume of the first liquid culture medium. In some embodiments of any of the methods described herein, the agitation is ceased for a period of time of at least 30 seconds prior to removing the first volume of the first liquid culture medium. In some embodiments of any of the methods described herein, the multi-well plate is sealed with a gas-permeable disposable membrane or a gas-permeable silicone layer. In some embodiments of any of the methods described herein, the well has a flat bottom or a round bottom.

Some embodiments of any of the methods described herein further include periodically adding an additional volume of second liquid culture medium to each of the plurality of wells in order to offset any decrease in the volume of the first liquid culture medium due to evaporation. In some embodiments of any of the methods described herein, the removing of the first volume of the first liquid culture medium and the adding to the first liquid culture medium the second volume of the second liquid culture medium is performed using an automated device. In some embodiments of any of the methods described herein, the multi-well plate is any of the multi-well cell culture plate systems described herein. In some embodiments of any of the methods described herein, the method results in a viable cell density of between $15 \times 10^6$ cells/mL and $60 \times 10^6$ cells/mL in the well.

Also provided are methods of culturing a mammalian cell that include: culturing in a gradient perfusion process a mammalian cell suspended in a liquid culture medium disposed within a well of a multi-well plate under conditions that generate in the medium a fluid sheer force and dissolved oxygen ($O_2$) concentration that is essentially the same as that achieved in a medium occupying about 15% to about 25% of the volume of a square-bottom well having a diameter of between about 6.0 mm and about 35 mm and a height of between about 40 mm and about 50 mm, when the square-bottom well is incubated at a temperature of about 31° C. to about 40° C., and rotary agitated at a frequency of about 320 revolutions per minute (RPM) to about 360 RPM. In some embodiments of these methods, the mammalian cell is a Chinese hamster ovary (CHO) cell (e.g., a CHO cell containing a nucleic acid encoding a recombinant protein (e.g., an immunoglobulin, an enzyme, a growth factor, a protein fragment, or an engineered protein)).

Also provided are methods of producing a recombinant protein that include: culturing in a gradient perfusion process a mammalian cell suspended in a liquid culture medium disposed within a well of a multi-well plate under conditions that generate in the medium a fluid sheer force and dissolved oxygen ($O_2$) concentration that is essentially the same as that achieved in a medium occupying about 15% to about 25% of the volume of a square-bottom well having a diameter of between about 6.0 mm and about 35 mm, and a height of between about 40 mm and about 50 mm, when the square-bottom well is incubated at a temperature of about 31° C. to about 40° C., and rotary agitated at a frequency of about 320 revolutions per minute (RPM) to about 360 RPM; and recovering the recombinant protein from the mammalian cell or the liquid culture medium. In some embodiments of any of these methods, the recombinant protein (e.g., an immunoglobulin, an enzyme, a growth factor, a protein fragment, or an engineered protein) is recovered from the mammalian cell. In some embodiments of any of these methods, the recombinant protein (e.g., a secreted immunoglobulin, a secreted enzyme, a secreted growth factor, a secreted protein fragment, or a secreted engineered protein) is recovered from the liquid culture medium. In some embodiments of these methods, the mammalian cell is a Chinese hamster ovary (CHO) cell.

In some embodiments of any of the methods described herein, the multi-well plate is selected a 6-well plate, a 12-well plate, a 24-well plate, a 48-well plate, or a 96-well plate. In some embodiments of any of the methods described herein, the multi-well plate is a deep-well plate. In some embodiments of any of the methods described herein, the liquid culture medium is selected from the group consisting of: a chemically-defined liquid culture medium, a serum-free liquid culture medium, a serum-containing liquid culture medium, an animal-derived component free liquid culture medium, and a protein-free medium. In some embodiments of any of the methods described herein, the multi-well plate is sealed with a gas-permeable disposable membrane or a gas-permeable silicone layer. In some embodiments of any of the methods described herein, the multi-well plate comprises wells having a flat bottom or a round bottom. In some embodiments of any of the methods described herein, the multi-well plate is one of the multi-well cell culture plate systems described herein. In some embodiments of any of the methods described herein, the culturing results in a viable cell density of between $15 \times 10^6$ cells/mL and $60 \times 10^6$ cells/mL in the well.

Also provided are multi-well cell culture plate systems that include: a unitary support plate including a first surface including a plurality of apertures; a plurality of culture vessels disposed within the support plate and configured to house cell cultures having a volume of between about 200 µL to about 18 mL in volume, wherein each aperture is paired with and defines an opening into each culture vessel and wherein each culture vessel further includes at least one port configured to accommodate a flow of fluid into and/or out of the culture vessel. In some embodiments of any of the systems described herein, the unitary support plate is configured to include a reservoir for housing and supplying liquid to the port. In some embodiments of any of the systems described herein, the culture vessel includes at least first and second ports, wherein the first port is configured to accommodate a one-way flow of fluid into the culture vessel and the second port is configured to accommodate a one-way flow of fluid out of the culture vessel. In some embodiments of any of the systems described herein, the port includes a filter configured to selectively prevent cells from flowing into and out of the culture vessel. In some embodiments of any of the systems described herein, the first and second ports each comprise a filter configured to selectively prevent cells from flowing into and out of the culture vessel. Some embodiments of any of the systems described herein further include at least one conduit disposed within the unitary support plate and in fluid connection with the port, wherein the conduit is configured to flow fluid to and/or from the culture vessel. Some embodiments of any of the systems described herein further include at least one fluid flow regulator operably connected to the at least one port. Some embodiments of any of the systems described herein further include at least one fluid flow meter operably connected to the at least one conduit.

As used herein, the word "a" before a noun represents one or more of the particular noun. For example, the phrase "a mammalian cell" represents "one or more mammalian cells."

The term "mammalian cell" means any cell from or derived from any mammal (e.g., a human, a hamster, a mouse, a green monkey, a rat, a pig, a cow, or a rabbit). In some embodiments, a mammalian cell can be an immortalized cell. In some embodiments, the mammalian cell is a differentiated cell. In some embodiments, the mammalian cell is an undifferentiated cell.

The term "day 0" means the time point at which a mammalian cell is seeded into the first liquid culture medium.

The term "day 1" means a time period between day 0 and about 24 hours following the seeding of a mammalian cell into the first liquid culture medium.

The term "day 2" means a time period of about 24 hours to about 48 hours following the seeding of a mammalian cell into the first liquid culture medium.

The term "day 3" means a time period of about 48 hours to about 72 hours following the seeding of a mammalian cell into the first liquid culture medium.

The term "day 4" means a time period of about 72 hours to about 96 hours following the seeding of a mammalian cell into the first liquid culture medium. The term for each additional day ("day 5," "day 6," "day 7," and so on) is meant a time period that ranges over an additional about 24-hour period from the end of the immediately preceding day.

The term "substantially free" means a composition (e.g., a liquid culture medium) that is at least or about 90% free (e.g., at least or about 95%, 96%, 97%, 98%, or at least or about 99% free, or about 100% free) of a specific substance (e.g., a mammalian cell).

The term "0.5× volume" means about 50% of the volume. The term "0.6× volume" means about 60% of the volume. Likewise, 0.7×, 0.8×, 0.9×, and 1.0× means about 70%, 80%, 90%, or 100% of the volume, respectively.

The term "culturing" or "cell culturing" is meant the maintenance or growth of a mammalian cell under a controlled set of physical conditions.

The term "liquid culture medium" means a fluid that contains sufficient nutrients to allow a mammalian cell to grow in vitro. For example, a liquid culture medium can contain one or more of: amino acids (e.g., 20 amino acids), a purine (e.g., hypoxanthine), a pyrimidine (e.g., thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, iron sulfate, copper sulfate, zinc sulfate, and sodium bicarbonate. In some embodiments, a liquid culture medium can contain serum from a mammal. In some embodiments, a liquid culture medium does not contain serum or another extract from a mammal (a defined liquid culture medium). In some embodiments, a liquid culture medium can contain trace metals, a mammalian growth hormone, and/or a mammalian growth factor. Non-limiting examples of liquid culture medium are described herein. Additional examples of liquid culture medium are known in the art and are commercially available. A liquid culture medium can contain any density of mammalian cells. For example, as used herein, a first volume of the first culture medium removed from the well can be substantially free of mammalian cells.

The term "first liquid culture medium" means a volume of liquid culture medium that is suitable for the culture of a mammalian cell.

The term "second liquid culture medium" means a volume of liquid culture medium that is suitable for the culture of a mammalian cell that is separate from the volume of the first liquid culture medium prior to any mixing of the first and second liquid culture media.

The term "animal-derived component free liquid culture medium" means a liquid culture medium that does not contain any components (e.g., proteins or serum) derived from a mammal.

The term "serum-free liquid culture medium" means a liquid culture medium that does not contain the serum of a mammal.

The term "serum-containing liquid culture medium" means a liquid culture medium that contains a mammalian serum.

The term "chemically-defined liquid culture medium" means a liquid culture medium in which all of the chemical components are known. For example, a chemically-defined liquid culture medium does not contain fetal bovine serum, bovine serum albumin, or human serum albumin, as these preparations typically contain a complex mix of albumins and lipids.

The term "protein-free liquid culture medium" means a liquid culture medium that does not contain any protein (e.g., any detectable protein).

The term "agitation" means the movement of a multi-well plate containing at least one well containing a liquid culture medium in order to increase the dissolved $O_2$ concentration in the liquid culture medium. Agitation, such as rotary agitation, can be performed using any art known method, e.g., an instrument that moves the multi-well plate in a circular or ellipsoidal motion, such as a rotary shaker. Exemplary devices that can be used to agitate a multi-well plate are described herein. Additional examples of such devices are also known in the art and are commercially available.

The term "immunoglobulin" means a polypeptide containing an amino acid sequence of at least 15 amino acids (e.g., at least 20, 30, 40, 50, 60, 70, 80, 90, or 100 amino acids) of an immunoglobulin protein (e.g., a variable domain sequence, a framework sequence, or a constant domain sequence). The immunoglobulin may, for example, include at least 15 amino acids of a light chain immunoglobulin, e.g., at least 15 amino acids of a heavy chain immunoglobulin. The immunoglobulin may be an isolated antibody (e.g., an IgG, IgE, IgD, IgA, or IgM). The immunoglobulin may be a subclass of IgG (e.g., IgG1, IgG2, IgG3, or IgG4). The immunoglobulin may be an antibody fragment, e.g., a Fab fragment, a F(ab')2 fragment, or a scFv fragment. The immunoglobulin may also be a bi-specific antibody or a tri-specific antibody, or a dimer, trimer, or multimer antibody, or a diabody, an Affibody®, or a Nanobody®. The immunoglobulin can also be an engineered protein containing at least one immunoglobulin domain (e.g., a fusion protein). Non-limiting examples of immunoglobulins are described herein and additional examples of immunoglobulins are known in the art.

The term "protein fragment" or "polypeptide fragment" means a portion of a polypeptide sequence that is at least or about 4 amino acids, at least or about 5 amino acids, at least or about 6 amino acids, at least or about 7 amino acids, at least or about 8 amino acids, at least or about 9 amino acids, at least or about 10 amino acids, at least or about 11 amino acids, at least or about 12 amino acids, at least or about 13 amino acids, at least or about 14 amino acids, at least or about 15 amino acids, at least or about 16 amino acids, at least or about 17 amino acids, at least or about 18 amino acids, at least or about 19 amino acids, or at least or about 20 amino acids in length, or more than 20 amino acids in length. A recombinant protein fragment can be produced using any of the methods described herein.

The term "engineered protein" means a polypeptide that is not naturally encoded by an endogenous nucleic acid present within an organism (e.g., a mammal). Examples of engineered proteins include enzymes (e.g., with one or more amino acid substitutions, deletions, insertions, or additions that result in an increase in stability and/or catalytic activity of the engineered enzyme), fusion proteins, antibodies (e.g., divalent antibodies, trivalent antibodies, or a diabody), and antigen-binding proteins that contain at least one recombinant scaffolding sequence.

The term "fluid sheer force" means a stress caused by a liquid flowing roughly parallel to a surface (e.g., a surface of a cell or a surface of a well). Fluid sheer force is generally defined as the force applied divided by the cross-sectional area of material with area parallel to the applied force vector. Exemplary methods of calculating fluid sheer force are described herein and are known in the art.

The term "dissolved $O_2$ concentration" or "dissolved oxygen concentration" means the amount of oxygen gas dissolved in a liquid culture medium (e.g., any of the liquid culture media described herein or known in the art). Non-limiting methods for measuring the dissolved $O_2$ concentration in a liquid culture medium are described herein and others are known in the art.

The term "recovering" means partially purifying or isolating (e.g., at least or about 5%, e.g., at least or about 10%, 15%, 20%, 25%, 30%, 40%, 45%, 50%, 55%, 60%, 65%, 70%, 75%, 80%, 85%, 90%, or at least or about 95% pure by weight) a recombinant protein from one or more other components present in the cell culture medium (e.g., mammalian cells or culture medium proteins) or one or more other components (e.g., DNA, RNA, or other proteins) present in a mammalian cell lysate. Non-limiting methods for recovering a protein from a liquid culture medium or from a mammalian cell lysate are described herein and others are known in the art.

The term "secreted protein" or "secreted recombinant protein" means a protein or a recombinant protein that originally contained at least one secretion signal sequence when it is translated within a mammalian cell, and through, at least in part, enzymatic cleavage of the secretion signal sequence in the mammalian cell, is released into the extracellular space (e.g., a liquid culture medium).

The phrase "gradient perfusion" refers to the incremental change (e.g., increase or decrease) in the volume of culture medium removed and added over incremental periods (e.g., an about 24-hour period, a period of between about 1 minute and about 24-hours, or a period of greater than 24 hours) during the culturing period (e.g., the culture medium refeed rate on a daily basis). For example, one embodiment of a gradient perfusion process may entail refeed protocols as follows: days 1-3 refeed of about 0.5× reactor volume of culture medium (RV)/day, days 4-6 refeed of about 0.7×RV/day, and day 7 and onwards refeed of about 1.0×RV/day. This particular example can vary with respect to the number of days having a certain refeed rate and/or with respect to the refeed rate over any particular 24-hour period. The fraction of media removed and replaced each day can vary depending on the particular cells being cultured, the initial seeding density, and the cell density at a particular time. "RV" or "reactor volume" means the volume of the culture medium present at the beginning of the culturing process (e.g., the total volume of the culture medium present after seeding).

The term "feed-batch culture" means the incremental or continuous addition of a second liquid culture medium to an initial cell culture without substantial or significant removal of the first liquid culture medium from the cell culture. In some embodiments of feed-batch culture, the second liquid culture medium is the same as the first liquid culture medium. In some embodiments of feed-batch culture, the second liquid culture medium is a concentrated form of the first liquid culture medium. In some embodiments of feed-batch culture, the second liquid culture medium is added as a dry powder.

"Specific productivity rate" or "SPR" as used herein refers to the mass or enzymatic activity of a recombinant protein produced per mammalian cell per day. The SPR for a recombinant antibody is usually measured as mass/cell/day. The SPR for a recombinant enzyme is usually measured as units/cell/day or (units/mass)/cell/day.

"Volume productivity rate" or "VPR" as used herein refers to the mass or enzymatic activity of recombinant protein produced per volume of culture (e.g., per L of bioreactor, vessel, or tube volume) per day. The VPR for a recombinant antibody is usually measured as mass/L/day. The VPR for a recombinant enzyme is usually measured as units/L/day or mass/L/day.

The term "microcarrier" means a particle (e.g., an organic polymer) that has a size of between 20 µm to about 1000 µm that contains a surface that is permissive or promotes attachment of a mammalian cell (e.g., any of the mammalian cells described herein or known in the art). A microcarrier can contain one or more pores (e.g., pores with an average diameter of about 10 µm to about 100 µm). Non-limiting examples of microcarriers are described herein. Additional examples of microcarriers are known in the art. A microcarrier can contain, e.g., a polymer (e.g., cellulose, polyethylene glycol, or poly-(lactic-co-glycolic acid)).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2 is a schematic diagram of a side view of an exemplary multi-well plate system.

FIG. 3 is a schematic diagram of a side view of an alternative multi-well plate system.

FIG. 4 is a schematic diagram of a side view of an alternative multi-well plate system.

DETAILED DESCRIPTION

Figure 1:
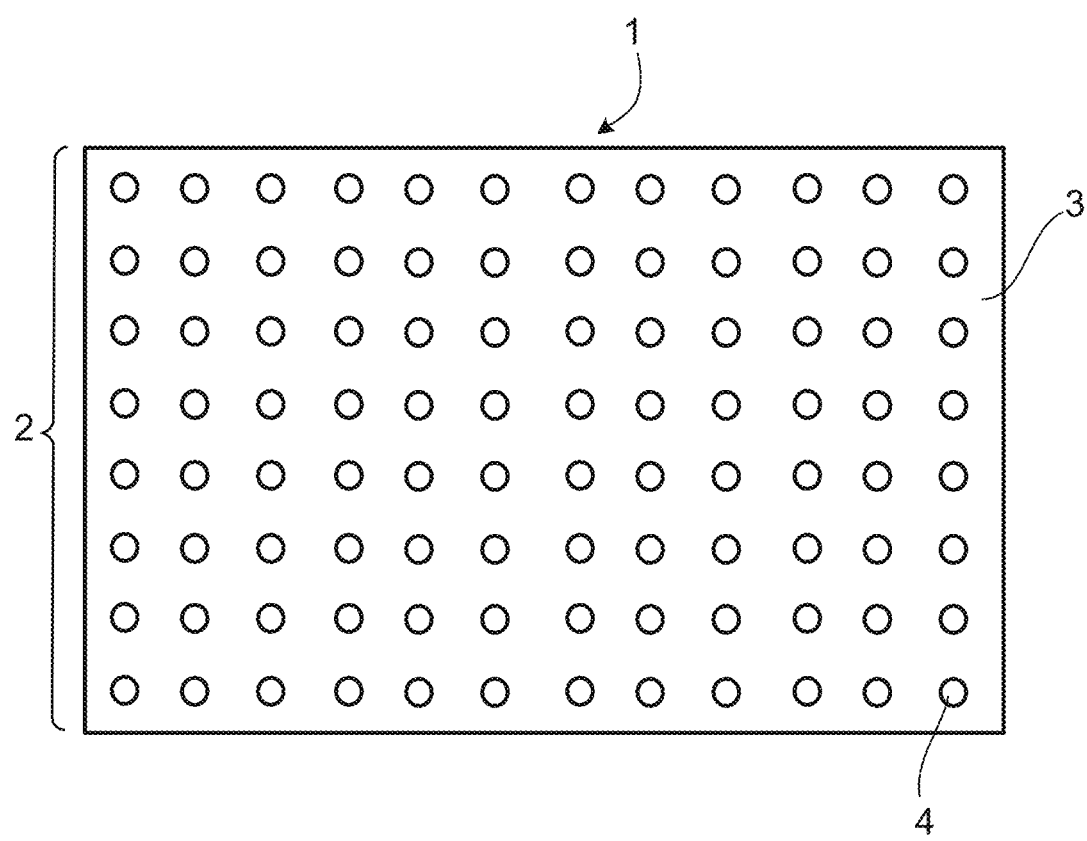
FIG. 1 is a schematic diagram of a top view of an exemplary multi-well plate system.

Provided herein are improved methods of culturing a mammalian cell in a multi-well plate. The culturing methods can achieve a viable mammalian cell concentration (e.g., in the liquid culture medium, e.g., the first liquid culture medium, or a combination of the first and second liquid culture medium) similar to that achieved by a larger scale production perfusion bioreactor, e.g., a viable mammalian cell density greater than $10 \times 10^6$ cells per mL, greater than $15 \times 10^6$ cells/mL, greater than $20 \times 10^6$ cells/mL, greater than $25 \times 10^6$ cells/mL, greater than $30 \times 10^6$ cells/mL, greater than $35 \times 10^6$ cells/mL, greater than $40 \times 10^6$ cells/mL, greater than $45 \times 10^6$ cells/mL, greater than $50 \times 10^6$ cells/mL, greater than $55 \times 10^6$ cells/mL, or greater than $60 \times 10^6$ cells/mL. For example, the culturing method can result in a viable mammalian cell concentration of between $10 \times 10^6$ cells/mL and $70 \times 10^6$ cells/mL, between $10 \times 10^6$ cells/mL and $65 \times 10^6$ cells/mL, between $10 \times 10^6$ cells/mL and $60 \times 10^6$ cells/mL, between $10 \times 10^6$ cells/mL and $50 \times 10^6$ cells/mL, between $10 \times 10^6$ cells/mL and $40 \times 10^6$ cells/mL, between $10 \times 10^6$ cells/mL and $30 \times 10^6$ cells/mL, between $15 \times 10^6$ cells/mL and $70 \times 10^6$ cells/mL, between $15 \times 10^6$ cells/mL and $65 \times 10^6$ cells/mL, between $15 \times 10^6$ cells/mL and $60 \times 10^6$ cells/mL, between $15 \times 10^6$ cells/mL and $55 \times 10^6$ cells/mL, between $15 \times 10^6$ cells/mL and $50 \times 10^6$ cells/mL, between $15 \times 10^6$ cells/mL and $45 \times 10^6$ cells/mL, between $15 \times 10^6$ cells/mL and $40 \times 10^6$ cells/mL, between $15 \times 10^6$ cells/mL and $35 \times 10^6$ cells/mL, between $20 \times 10^6$ cells/mL and $70 \times 10^6$ cells/mL, between $20 \times 10^6$ cells/mL and $65 \times 10^6$ cells/mL, between $20 \times 10^6$ cells/mL and $60 \times 10^6$ cells/mL, between $20 \times 10^6$ cells/mL and $55 \times 10^6$ cells/mL, between $20 \times 10^6$ cells/mL and $50 \times 10^6$ cells/mL, between $20 \times 10^6$ cells/mL and $45 \times 10^6$ cells/mL, between $20 \times 10^6$ cells/mL and $40 \times 10^6$ cells/mL, between $25 \times 10^6$ cells/mL and $70 \times 10^6$ cells/mL, between $25 \times 10^6$ cells/mL and $65 \times 10^6$ cells/mL, between $25 \times 10^6$ cells/mL and $60 \times 10^6$ cells/mL, between $25 \times 10^6$ cells/mL and $55 \times 10^6$ cells/mL, between $25 \times 10^6$ cells/mL and $50 \times 10^6$ cells/mL, between $25 \times 10^6$ cells/mL and $45 \times 10^6$ cells/mL, between $30 \times 10^6$ cells/mL and $70 \times 10^6$ cells/mL, between $30 \times 10^6$ cells/mL and $65 \times 10^6$ cells/mL, between $30 \times 10^6$ cells/mL and $60 \times 10^6$ cells/mL, between $30 \times 10^6$ cells/mL and $55 \times 10^6$ cells/mL, between $30 \times 10^6$ cells/mL and $50 \times 10^6$ cells/mL, between $35 \times 10^6$ cells/mL and $70 \times 10^6$ cells/mL, between $35 \times 10^6$ cells/mL and $65 \times 10^6$ cells/mL, between $35 \times 10^6$ cells/mL and $60 \times 10^6$ cells/mL, between $35 \times 10^6$ cells/mL and $55 \times 10^6$ cells/mL, between $40 \times 10^6$ cells/mL and $70 \times 10^6$ cells/mL, between $40 \times 10^6$ cells/mL and $65 \times 10^6$ cells/mL, between $40 \times 10^6$ cells/mL and $60 \times 10^6$ cells/mL, between $40 \times 10^6$ cells/mL and $55 \times 10^6$ cells/mL, between $45 \times 10^6$ cells/mL and $70 \times 10^6$ cells/mL, or between $45 \times 10^6$ cells/mL and $65 \times 10^6$ cells/mL. A variety of different methods can be used to determining the cell density or viable cell density. For example, the sample of the cell culture can be diluted in physiological buffer, the diluted cell suspension placed in a hemocytometer, and the cells counted using light microscopy. In another method, the viable cell density can be determined using a similar method, but including in the physiological buffer a dye that is selectively taken up by non-viable cells (e.g., trypan blue, such as Vi-CELL method from Beckman Coulter (see Beckman Coulter website)). In yet another example, the cell density or viable cell density can be determined using fluorescence-assisted flow cytometry (e.g., GUAVA from Merck Millipore (see Millipore website), and other cell counting methods.

In some embodiments, the culturing method results in a significantly improved specific productivity rate. For example, the specific productivity rate achieved by the methods provided herein is at least 2-fold, 3-fold, 4-fold, 5-fold, 6-fold, 7-fold, 8-fold, 9-fold, 10-fold, 15-fold, 20-fold, 30-fold, 40-fold, 50-fold, 60-fold, 70-fold, 80-fold, 90-fold, or 100-fold greater than the specific productivity rate achieved under substantially the same culturing conditions, but without removing a volume of the first culture medium and adding a second volume of the second culture medium. The productivity achieved by the present methods can be at least 10,000 units/L, at least 15,000 units/L, at least about 20,000 units/L, at least about 25,000 units/L, at least about 30,000 units/L, at least about 35,000 units/L, or at least about 40,000 units/L (in the first and/or second liquid culture medium). In some embodiments, the productivity achieved by the present methods can be at least 1 g/L, at least 1.5 g/L, at least 2.0 g/L, at least 2.5 g/L, at least 3.0 g/L, at least 4.0 g/L, at least 4.5 g/L, or at least 5.0 g/L.

The biological activity of a recombinant protein can be assessed using a variety of methods known in the art, and will depend on the activity of the specific recombinant protein. For example, the biological activity of a recombinant protein that is an immunoglobulin (e.g., an antibody or an antibody fragment) can be determined by measuring the affinity of the antibody to bind to its specific epitope (e.g., using Biocore or competitive enzyme-linked immunosorbent assays). The recombinant protein may be an enzyme (e.g., a recombinant galactosidase, e.g., a recombinant alpha-galactosidase) and the biological activity may be determined by measuring the enzyme's activity (e.g., determining the catalytic rate constant of the enzyme by measuring a decrease in the concentration of a detectable substrate or an increase in the concentration of a detectable product (e.g., using spectrophotometry or light emission). For example, the biological activity of a recombinant galactosidase can be detected by measuring a decrease in the level of globotriasylceramide (GL-3) or galabiosylceramide, or an increase in the level of ceramide dihexoside or galactose.

Also provided are multi-well cell culture plate systems that can be used to perform, e.g., any of the methods described herein.

Methods for Testing a Manufacturing Process

Provided herein are methods for testing a manufacturing process for making a recombinant protein (e.g., any of the recombinant proteins described herein or known in the art). These methods include performing a method of producing a recombinant protein described herein and, during the method and/or afterward, detecting or measuring at least one (e.g., two, three four, five, six, seven, eight, nine, ten, eleven, twelve, thirteen, or fourteen) culture readout (e.g., the amount of recombinant protein in the cell or in the first and/or second culture medium, glucose consumption, viable cell concentration, lactate production, volumetric productivity rate, specific productivity rate, lactate yield from glucose, glutamine concentration, glutamate concentration, pH of culture medium, partial pressure or concentration of dissolved $CO_2$, concentration or partial pressure of dissolved $O_2$, metabolite mass transfer, and metabolite mass balance); and comparing the at least one culture readout to a reference level of the at least one (e.g., two, three, four, five, six, seven, eight, nine, ten, eleven, twelve, or thirteen) culture readout (e.g., a reference level of the amount of recombinant protein present (e.g., detected) in the cell or in the first and/or second culture medium, glucose consumption, viable cell concentration, lactate production, volumetric productivity rate, specific productivity rate, lactate yield from glucose, glutamine concentration, glutamate concentration, pH of culture medium, concentration or partial pressure of dissolved $CO_2$, concentration or partial pressure of dissolved $O_2$, metabolite mass transfer, and metabolite mass balance).

Skilled practitioners will appreciate that any of the various culture parameters (e.g., multi-well plates, volumes, rates or frequencies of replacing culture volumes, agitation frequencies, temperatures, media, $CO_2$ concentrations, and reactor angle) described herein can be used in any combination in to perform these methods. Further, any of the mammalian cells described herein or known in the art can be used in the methods.

The reference level of the at least one culture readout (e.g., amount of recombinant protein in the cell or in the first and/or second culture medium, glucose consumption, viable cell concentration, lactate production, volumetric productivity rate, specific productivity rate, lactate yield from glucose, glutamine concentration, glutamate concentration, pH of culture medium, concentration or partial pressure of dissolved $CO_2$, concentration or partial pressure of dissolved $O_2$, metabolite mass transfer, and metabolite mass balance) can be a level produced using a different culturing method, e.g., a culturing method that utilizes at least one different culture parameter (e.g., a different first and/or second liquid culture medium, a different mammalian cell, a different frequency and/or type of agitation, a different multi-well plate, a different batch refeed or perfusion rate (e.g., 10% to 200% of the well volume or the first liquid culture medium volume over a 24-hour time period or other incremental time period), and any of the other culture parameters described herein). The reference amount of recombinant protein can be, e.g., a level of recombinant protein produced using a set of culturing parameters that result in a different level of dissolved $O_2$ and/or a different level of liquid sheer stress.

The methods described herein can be used to test the effect of any component or feature of a manufacturing process. For example, the method described herein can be used to test the effect of different raw materials, agitation levels, multi-well plates, anti-clumping agents, culture media (e.g., chemically-defined culture media), or nutrient elements or compounds on the at least one culture readout (e.g., any of the culture readouts described herein, e.g., the effect on recombinant protein production and/or mammalian cell growth). For example, provided herein are methods of testing the efficacy of a first or second liquid culture medium, a raw ingredient or supplement present in a first or second liquid culture medium, or a source of a mammalian cell for use in a method of producing a recombinant protein that include providing a multi-well plate containing at least one well containing a mammalian cell disposed in a first liquid culture medium occupying about 5% to about 70% of the volume of the well; incubating the multi-well plate for a period of time at about 31° C. to about 40° C. with a rotary agitation of about 320 RPM to about 500 RPM; continuously or periodically, during the period of time, removing a first volume of the first liquid culture medium and adding to the first liquid culture medium a second volume of a second liquid culture medium, where the first and second volumes are about equal; detecting or determining at least one culture readout (e.g., any of the culture readouts described herein, e.g., the amount of recombinant protein in the cell or in the first and/or second culture medium); comparing the at least one culture readout to a reference level of the at least one culture readout (e.g., any of the culture readouts described herein, e.g., amount of recombinant protein in the cell or in the first and/or second liquid culture medium) produced by a different culturing method that uses one or more of a different first or second liquid culture medium, or a different source of a mammalian cell; and identifying the first or second liquid culture medium, the raw ingredient or supplement present in the first or second liquid culture medium, or the source of the mammalian cell that is associated with beneficial change (e.g., increase or decrease) in the at least one culture readout (e.g., an increased amount of recombinant protein) as compared to the reference level as being efficacious for use in a method of producing a recombinant protein. For example, an increase in recombinant protein level, an increase in viable cell concentration, an increase in volumetric productivity rate, an increase in specific productivity rate, and an increase in glucose consumption compared to the reference level indicates that the first or second liquid culture medium, the raw ingredient or supplement present in a first or second liquid culture medium, or the source of the mammalian cell are efficacious for use in a method of producing a recombinant protein.

The methods described herein can also be used to test the effect of changing any of the various cell culturing parameters described herein or known in the art (e.g., the volume, height, diameter, or bottom shape of a well, the frequency or type of agitation, the sheer force, the culture seeding density, the pH of the first or second liquid culture medium, dissolved $O_2$ concentration or partial pressure, the inner surface coating of the well, the various contents within a liquid culture media (e.g., the first and/or second liquid culture media), the mammalian cell type or line, the $CO_2$ exposure or dissolved $CO_2$ concentration or partial pressure, the temperature, the volume of liquid culture medium (e.g., the volume of the first and/or second liquid culture media), and/or the rate or frequency of removing the first volume of the first culture medium and adding the second volume of the second culture medium to the first culture medium). The methods can also be used to test the quality of water used to prepare the liquid culture medium (e.g., the first and/or second liquid culture medium) and/or the effect of different trace metals in the liquid culture medium on at least one culture readout (e.g., any of the culture readouts described herein, e.g., the effect on recombinant protein production and/or mammalian cell growth). The methods can also be used to test the effect of a growth factor or growth hormone on at least one culture readout (e.g., any of the culture readouts described herein, e.g., the effect on recombinant protein production and/or mammalian cell growth). The method can also be used to test filtration processes and filters used to prepare the first and/or second liquid culture medium. The method can also be used to test liquid culture medium stability and the effect of a liquid culture medium on biological functions (e.g., at least one of any of the culture readouts described herein, e.g., the effect on recombinant protein production and/or mammalian cell growth). The method can also be used to screen various recombinant cell lines and cell banks for their ability to produce a desired recombinant protein (e.g., a desired secreted therapeutic protein). As noted herein, the method can also be used to screen any cell culture process parameter, including but limited to, the type and frequency of agitation, sheer force, perfusion rate and volume, culture seeding density, and others.

The method described herein can also be used to test for the presence of a contaminant in a first or second liquid culture medium, a raw material used to generate a first or second liquid culture medium, or a source of a mammalian cell. For example, provided herein are methods of testing for the presence of a contaminant in a first or second liquid culture medium, raw materials used to generate a first or second liquid culture medium, or a source of a mammalian cell that include providing a multi-well plate containing at least one well containing a mammalian cell suspended in a first liquid culture medium occupying about 5% to about 70% of the volume of the well; incubating the multi-well plate for a period of time at about 31° C. to about 40° C. and with an agitation of about 320 revolutions per minute (RPM) to about 500 RPM; continuously or periodically, during the period of time, removing a first volume of the first liquid culture medium and adding to the first liquid culture medium a second volume of a second liquid culture medium, where the first and second volumes are about equal; detecting or determining at least one culture readout (e.g., any of the culture readouts described herein, e.g., the amount of recombinant protein in the cell or in the first and/or second liquid culture medium); comparing the at least one culture readout to a reference level of the at least one culture readout (e.g., any of the culture readouts described herein, e.g., amount of recombinant protein present in the cell or in the first and/or second culture medium) produced by a different culturing method that uses one or more of a different first or second liquid culture medium, different raw materials to generate the first or second liquid culture medium, or a different source of the mammalian cell; and identifying the first or second liquid culture medium, the raw materials used to generate the first or second liquid culture medium, or the source of a mammalian cell as containing a contaminant when the level of the at least one culture parameter is detrimentally changed (e.g., increased or decreased) compared to the reference level. For example, a decrease in recombinant protein production (e.g., a decrease in recombinant protein in the cell or in the first and/or second culture medium), volumetric productivity rate, or viable cell concentration as compared to the reference level is a detrimental change that indicates the presence of a contaminant in the first or second liquid culture medium, a raw material used to generate the first or second liquid culture medium, or the source of the mammalian cell. Some methods further include one or more assays to determine the identity of the contaminant present in the first or second liquid culture medium, the raw material used to generate the first or second liquid culture medium, or the source of the mammalian cell. The contaminant can be a biological contaminant (e.g., a *mycobacterium*, a fungus, a bacterium, a virus, or an undesired mammalian cell). The contaminant can also be a physically uncharacterized substance.

The methods can used to conduct high throughput cell culture experiments to perform a design-of-experiment (DOE) or a quality-by-design (QBD) optimization of cell culturing methods. For example, provided herein are methods of optimizing a manufacturing process of producing a recombinant protein that include providing a multi-well plate containing at least one well containing a mammalian cell suspended in a first liquid culture medium occupying about 5% to about 70% of the volume of the well; incubating the multi-well plate for a period of time at about 31° C. to about 40° C. and with a rotary agitation of about 320 RPM to about 500 RPM; continuously or periodically, during the period of time, removing a first volume of the first liquid culture medium and adding to the first liquid culture medium a second volume of a second liquid culture medium, where the first and second volumes are about equal; detecting at least one culture readout (e.g., any of the culture readouts described herein, e.g., amount of recombinant protein in the cell or in the first and/or second liquid culture medium);

comparing the at least one culture readout to a reference level of the at least one culture readout (e.g., any of the culture readouts described herein, e.g., amount of recombinant protein present in the cell or in the first and/or second liquid culture medium) produced by a different culture method; and identifying and removing or altering in the manufacturing process any culture components or parameters that are associated with a detrimental change (e.g., increase or decrease) in the at least one culture readout (e.g., any of the culture readouts described herein, e.g., amount of recombinant protein produced) as compared to the reference level of the at least one culture readout (e.g., any of the culture readouts described herein, e.g., recombinant protein produced), or identifying and adding to a manufacturing process any culture components or parameters that are associated with a beneficial change (e.g., increase or decrease) in the at least one culture readout (e.g., any of the culture readouts described herein, e.g., amount of recombinant protein produced) as compared to the reference level of the at least one culture readout (e.g., any of the culture readouts described herein, e.g., recombinant protein produced). For example, an increase in the amount of recombinant protein produced, volumetric productivity rate, specific productivity rate, or viable cell concentration is a beneficial change in a culture readout, and a decrease in the amount of recombinant protein produced, volumetric productivity rate, specific productivity rate, or viable cell concentration is a detrimental change in a culture readout. In some instances, the method is used to identify in a high throughput fashion, optimized cell culture conditions that can be used for up-scaled (e.g., bioreactor) production of a recombinant protein.

In any of the methods described in this section, the reference level of the at least one culture readout can be from a larger-scale culture (e.g., a perfusion bioreactor, e.g., a 2000-L perfusion bioreactor, 40-L perfusion bioreactor, or a 12-L perfusion bioreactor). In some embodiments of any of the methods described in this section, the mammalian cell is cultured in a multi-well plate using any of the methods described herein over the same time period that a larger-scale culture is performed (cultured in paralleled). For example, the inoculum used to inoculate the multi-well plate in any of the methods described herein is also used to inoculate a larger-scale perfusion bioreactor at approximately the same time.

In one embodiment, the inoculum that is used to seed the well(s) is obtained from a larger-scale culture (e.g., a larger-scale perfusion bioreactor). For example, an aliquot from a larger-scale culture at any time point (e.g., removed during the growth phase, the transition phase (e.g., an optional period when the culture is being transitioned to a different set of growth conditions, e.g., a different liquid culture medium and/or temperature), or the harvest phase) and used to inoculate the well(s) (e.g., used to start a satellite multi-well plate culture). An aliquot can be removed from the larger-scale culture during the growth phase and used to inoculate or seed a multi-well plate containing at least one well containing a liquid culture medium, and the well(s) is then incubated under conditions that replicate or are similar to the growth phase conditions employed in the larger-scale culture. An aliquot can alternatively, or additionally, be removed from the larger-scale culture during a transition phase and used to inoculate or seed a multi-well plate containing at least one well containing a liquid culture medium, and the well(s) is then incubated under conditions that replicate or are similar to the transition phase conditions employed in the larger-scale culture. An aliquot can alternatively, or additionally, be removed from the larger-scale culture during the harvest phase and used to inoculate or seed a multi-well plate containing at least one well containing a liquid culture medium, and the well(s) is then incubated under conditions that replicate or are similar to the harvest phase conditions employed in the larger-scale culture. In any of these methods, one or more culture parameters can be altered in the methods used to culture the mammalian cell in the multi-well plate (as compared to the culture parameters or components used to culture the mammalian cell in the larger-scale culture), at least one culture readout is measured, and the at least one culture readout is compared to the at least one culture readout determined for the larger-scale culture. As can be appreciated by those in the art, these methods can be used to test the effect of a specific culture parameter or component on at least one culture readout during one or more specific phases in the culturing process (e.g., the effect of one or more culture parameters and/or culture component(s) on at least one culture readout during the growth phase, optional transition phase, and/or harvest phase).

In certain embodiments, these methods can also be performed to determine whether a contaminant is present in the larger-scale bioreactor, by determining or detecting at least one culture readout in the multi-well plate (e.g., inoculated with an aliquot of the larger-scale bioreactor culture or the same frozen cell bank used to inoculate the larger-scale bioreactor), comparing the at least one culture readout to a reference level of the at least one culture readout (e.g., a level of the at least one culture readout from a culture that is substantially free of contamination), and identifying the larger-scale bioreactor as containing a contaminant when the at least one culture readout in the well as compared to the reference level of the at least one culture readout indicates that a contaminant is present in the well. The contaminant can be, for example, a biological contaminant, such as a virus, a fungus, an undesired mammalian cell, or a bacterium, such as a *mycobacterium*. The contaminant can be, for example, a vesivirus.

Multi-Well Cell Culture Plate Systems

The present specification provides exemplary multi-well cell culture plate systems useful for culturing a mammalian cell (e.g., using any of the methods described herein). These systems are designed to allow for the continuous or periodic removal of fluid (e.g., a first liquid culture medium) present in a culturing vessels) and adding to the culturing vessels) a fluid (e.g., a second liquid culture medium) through at least one port configured to accommodate a flow of fluid into and/or out of the culture vessel(s).

Exemplary Multi-Well Cell Culture Plate Systems

A top view of a non-limiting example of a multi-well cell culture plate system 1 is provided in FIG. 1. Multi-well cell culture plate system 1 includes a unitary support plate 2 comprising a surface 3 having a plurality of apertures 4. Apertures can be arranged in any format and while FIG. 1 shows apertures in a line and row format, skilled practicioners will appreciate that any configuration of apertures can be employed.

A side view of an exemplary multi-well culture plate system 11 is shown in FIG. 2. The multi-well culture plate system 11 includes a unitary support plate 2 having a surface 3 that includes a plurality of apertures 4. The unitary support plate 2 can be made of any biologically compatible material (e.g., polystyrene or any other biologically compatible material known in the art). The unitary support plate 2 can have at least 2 apertures 4 (e.g., 4, 6, 9, 10, 12, 15, 18, 20, 24, 36, 48, 60, 72, or 96 apertures 4) or can have at least 3, 4, 5, 6, 12, 18, 24, 36, 48, or 96 apertures 4. The multi-well culture plate system 11 shown in FIG. 2 also has a plurality of culture vessels 5 that are formed or disposed within the support plate 2 and configured to house cell cultures (e.g., any of the exemplary mammalian cells and/or tissue culture media described herein). The vessels 5 can be configured to house cell cultures of any volume, e.g., those having a volume of between about 0.3 mL and about 25 mL (e.g., between about 0.3 mL and about 24 mL, between about 0.3 mL and about 22 mL, between about 0.3 mL and about 20 mL, between about 0.3 mL and about 18 mL, between about 0.3 mL and about 16 mL, between about 0.3 mL and about 14 mL, between about 0.3 mL and about 12 mL, between about 0.3 mL and about 10 mL, between about 0.3 mL and about 8 mL, between about 0.3 mL and about 6 mL, between about 0.3 mL and about 5 mL, between about 0.3 mL and about 4 mL, between about 0.3 mL and about 3 mL, between about 0.3 mL and about 2 mL, between about 0.3 mL and about 1 mL, between about 0.5 mL and about 25 mL, between about 0.5 mL and about 24 mL, between about 0.5 mL and about 22 mL, between about 0.5 mL and about 0.5 mL and about 20 mL, between about 0.5 mL and about 18 mL, between about 0.5 mL and about 16 mL, between about 0.5 mL and about 14 mL, between about 0.5 mL and about 12 mL, between about 0.5 mL and about 10 mL, between about 0.5 mL and about 8 mL, between about 0.5 mL and about 6 mL, between about 0.5 mL and about 5 mL, between about 0.5 mL and about 4 mL, between about 0.5 mL and about 3 mL, between about 0.5 mL and about 2 mL, between about 0.5 mL and about 1 mL, between about 1 mL and about 25 mL, between about 1 mL and about 24 mL, between about 1 mL and about 22 mL, between about 1 mL and about 20 mL, between about 1 mL and about 18 mL, between about 1 mL and about 16 mL, between about 1 mL and about 14 mL, between about 1 mL and about 12 mL, between about 1 mL and about 10 mL, between about 1 mL and about 8 mL, between about 1 mL and about 7 mL, between about 1 mL and about 6 mL, between about 1 mL and about 5 mL, between about 1 mL and about 4 mL, between about 1 mL and about 3.5 mL, between about 1 mL and about 3 mL, between about 1 mL and about 2.5 mL, between about 1 mL and about 2 mL, between about 1 mL and about 1.5 mL, between about 1.5 mL and about 25 mL, between about 1.5 mL and about 24 mL, between about 1.5 mL and about 22 mL, between about 1.5 mL and about 20 mL, between about 1.5 mL and about 18 mL, between about 1.5 mL and about 16 mL, between about 1.5 mL and about 14 mL, between about 1.5 mL and about 12 mL, between about 1.5 mL and about 10 mL, between about 1.5 mL and about 8 mL, between about 1.5 mL and about 6 mL, between about 1.5 mL and about 5 mL, between about 1.5 mL and about 4 mL, between about 1.5 mL and about 3.5 mL, between about 1.5 mL and about 3 mL, between about 1.5 mL and about 2.5 mL, between about 1.5 mL to about 2.0 mL, between about 2 mL and about 25 mL, between about 2 mL and about 24 mL, between about 2 mL and about 22 mL, between about 2 mL and about 20 mL, between about 2 mL and about 18 mL, between about 2 mL and about 16 mL, between about 2 mL and about 14 mL, between about 2 mL and about 12 mL, between about 2 mL and about 10 mL, between about 2 mL and about 8 mL, between about 2 mL and about 6 mL, or between about 2 mL and about 5 mL), where each aperture 3 is paired with and defines an opening into each culture vessel 4.

The culture vessel(s) 5 can have different shapes. Non-limiting examples of shapes of the culture vessel(s) can be a substantially cylinder or cylinder shape with an end opposite to that of the aperture 4 that is, e.g., flat, hemispherical, pyramidal, or conical. The diameter of the aperture 4 can be, e.g., between about 4.0 mm and about 50 mm (e.g., between about 4.0 mm and about 45 mm, between about 4.0 mm and about 40 mm, between about 4.0 mm and about 35 mm, between about 4.0 mm and about 30 mm, between about 4.0 mm and about 25 mm, between about 4.0 mm and about 20 mm, between about 4.0 mm and about 15 mm, between about 4.0 mm and about 10 mm, between about 6.0 mm and about 50 mm, between about 6.0 mm and about 45 mm, between about 6.0 mm and about 40 mm, between about 6.0 mm and about 35 mm, between about 6.0 mm and about 30 mm, between about 6.0 mm and about 25 mm, between about 6.0 mm and about 25 mm, between about 6.0 mm and about 20 mm, between about 6.0 mm and about 15 mm, between about 6.0 mm and about 10 mm, between about 8 mm and about 50 mm, between about 8 mm and about 45 mm, between about 8 mm and about 40 mm, between about 8 mm and about 35 mm, between about 8 mm and about 30 mm, between about 8 mm and about 25 mm, between about 8 mm and about 20 mm, between about 8 mm and about 15 mm, between about 10 mm and about 50 mm, between about 10 mm and about 45 mm, between about 10 mm and about 40 mm, between about 10 mm and about 35 mm, between about 10 mm and about 30 mm, between about 10 mm and about 25 mm, between about 10 mm and about 20 mm, between about 15 mm and about 50 mm, between about 15 mm and about 45 mm, between about 15 mm and about 40 mm, between about 15 mm and about 35 mm, between about 15 mm and about 30 mm, between about 15 mm and about 25 mm, or between about 15 mm and about 20 mm) The culture vessel(s) 5 can have a height of between 1 cm and about 12 cm (e.g., between about 1 cm and about 11 cm, between about 1 cm and about 10 cm, between about 1 cm and about 9 cm, between about 1 cm and about 8 cm, between about 1 cm and about 7 cm, between about 1 cm and about 6 cm, between about 1 cm and about 5 cm, between about 1 cm and about 4 cm, between about 1 cm and about 3 cm, between about 1.2 cm and about 12 cm, between about 1.2 cm and about 11 cm, between about 1.2 cm and about 10 cm, between about 1.2 cm and about 9 cm, between about 1.2 cm and about 8 cm, between about 1.2 cm and about 7 cm, between about 1.2 cm and about 6 cm, between about 1.2 cm and about 5 cm, between about 1.2 cm and about 4 cm, between about 1.2 cm and about 3 cm, between about 1.5 cm and about 11 cm, between about 1.5 cm and about 10 cm, between about 1.5 cm and about 9 cm, between about 1.5 cm and about 8 cm, between about 1.5 cm and about 7 cm, between about 1.5 cm and about 6 cm, between about 1.5 cm and about 5 cm, between about 1.5 cm and about 4 cm, between about 1.5 cm and about 3 cm, between about 2 cm and about 12 cm, between about 2 cm and about 11 cm, between about 2 cm and about 10 cm, between about 2 cm and about 9 cm, between about 2 cm and about 8 cm, between about 2 cm and about 7 cm, between about 2 cm and about 6 cm, between about 2 cm and about 5 cm, between about 2 cm and about 4 cm, between about 2 cm and about 3 cm, between about 2.5 cm and about 12 cm, between about 2.5 cm and about 11 cm, between about 2.5 cm and about 10 cm, between about 2.5 cm and about 9 cm, between about 2.5 cm and about 8 cm, between about 2.5 cm and about 7 cm, between about 2.5 cm and about 6 cm, between about 2.5 cm and about 5 cm, between about 2.5 cm and about 4 cm, between about 3 cm and about 12 cm, between about 3 cm and about 11 cm, between about 3 cm and about 10 cm, between about 3 cm and about 9 cm, between about 3 cm and about 8 cm, between about 3 cm and about 7 cm, between about 3 cm and about 6 cm, between about 3 cm and about 5 cm, between about 4 cm and about 12 cm, between about 4 cm and about 11 cm, between about 4 cm and about 10 cm, between about 4 cm and about 9 cm, between about 4 cm and about 8 cm, between about 4 cm and about 7 cm, between about 4 cm and about 6 cm, between about 5 cm and about 12 cm, between about 5 cm and about 11 cm, between about 5 cm and about 10 cm, between about 5 cm and about 9 cm, between about 5 cm and about 8 cm, or between about 5 cm and about 7 cm).

The multi-well cell culture plate system 11 shown in FIG. 2 also includes a port 6, e.g., a one or two way valve, configured to accommodate a flow of fluid into and out of the culture vessel 5. The port 6 can be fluidly connected to the culture vessel 5 at any location. A multi-well cell culture plate system described herein can have at least one, e.g., two, three, or at least four ports 6 fluidly connected to each culture vessel 5. Exemplary positions for the connection of a port 6 to a culture vessel 5 are shown in FIG. 2 and FIG. 3. A port 6 can be configured to flow fluid in one direction (e.g., into or out of the culture vessel 5) or in both directions (into and out of the culture vessel 5). In some embodiments, a first port 6 can be configured to accommodate a one-way flow into the culture vessel 5 and the second port 6 is configured to accommodate a one-way flow out of the culture vessel 5.

FIG. 3 shows a multi-well cell culture plate system 12 that includes a filter 8 configured to selectively prevent cells from flowing into and out of the culture vessel 5. A filter 8 can be any of the art-known micro- or nano-filters used to filter mammalian cells. A multi-well cell culture plate system having two or more ports 6 can have a filter 8 configured on or within each port 6 to selectively prevent cells from flowing into and out of the culture vessel 5.

The multi-well cell culture plate systems 12 and 13 shown in FIG. 2 and FIG. 3, respectively, also include at least one conduit 7 disposed within the unitary support plate 2 and in fluid communication with the port 6, wherein the conduit 7 is configured to flow fluid to and from the culture vessel 5. In some examples, a multi-well cell culture plate system can have a conduit 7 in fluid communication with each port 6 (e.g., configured to flow fluid to and/or from each culture vessel 5).

The multi-well cell culture plate systems provided herein can further include at least one fluid flow regulator operably linked to the port(s) 6. The multi-well cell culture plate systems provided herein can further include at least one fluid flow regulator operably connected to the conduit(s) 7. Non-limiting examples of fluid flow regulators can control fluid flow rate and/or flow direction by detecting changes in fluid volume and/or fluid pressure within the culture vessel(s) 5. In some examples, fluid flow regulators can be programmed to flow fluid at a specific rate for a specific period of time in a specific flow direction (e.g., into and/or out of the culture vessel(s) 5).

In some embodiments, the unitary support plate 2 is configured to include a reservoir for housing and supplying liquid to the port(s) 6 or conduit(s) 7. In some examples, the multi-well cell culture plate system includes a reservoir for housing and supplying liquid to the port(s) 6 or conduit(s) 7 configured such that it is external to the unitary support plate 2 and fluidly connected to the port(s) 6 or conduit(s) 7, respectively (wherein the port(s) 6 or conduit(s) 7 performs the function of flowing a fluid into the culture vessel(s) 5). In some embodiments, the unitary support plate 2 is configured to include a reservoir for housing and storing a liquid removed from the culture vessel(s) 5, where the reservoir for housing and storing a liquid removed is external to the unitary support plate 2 and is fluidly connected to the port(s) 6 or conduit(s) 7 (wherein the port(s) 6 or conduit(s) 7 performs the function of flowing a fluid out of the culture vessel(s) 5).

An exemplary unitary support plate 2 configured to include an internal reservoir 9 for housing and supplying liquid to the port(s) 6 is shown in FIG. 4. The unitary support plate 2 in FIG. 4 further includes an exchange port 10 for removing or adding a liquid to the internal reservoir 9. A unitary support plate that includes an internal reservoir 9 can include one- and/or two-way exchange ports 10 (e.g., one- or two-way valves). For example, a unitary support plate 2 that includes an internal reservoir 9 can have a first exchange port 10 that allows for the flow of liquid into the internal reservoir and a second exchange port that allows for the flow of liquid out of the internal reservoir. In another example, a unitary support plate 2 that includes an internal reservoir 9 can have a single two-way exchange port 10 that allows for the flow of liquid into and out of the internal reservoir 10. The fluid present in the internal reservoir 10 can be flowed into and/or out of the vessel(s) 5 through the use of one or more ports 6 and/or conduits 7.

In some examples, the multi-well cell culture plate further comprises a cover plate configured to cover the unitary support plate 2 and the aperture(s) 4 (e.g., all of the apertures 4 in the unitary support plate 2), prevent contamination (e.g., bacterial (e.g., mycobacterial), viral, or fungal contamination) of the culture vessel(s) 5, and allow for gas exchange between the culture vessel(s) 5 and the external environment. In some embodiments, the multi-well culture plate further comprises a gas-permeable disposable membrane or a gas-permeable silicone layer disposed between the cover plate and the unitary support plate 2 to prevent contamination of the culture vessel(s) 5, while allowing for gas exchange between the culture vessel(s) 5 and the external environment.

A fluid can be flowed through any of the systems (e.g., into and/or out of the system, e.g., into and/or out of a port 6, into and/or out of a conduit 7, or into and/or out of an exchange port 10) described herein using one or more of a variety of methods known in the art for, e.g., fluid pressure, air pressure, gravitational force, and mechanical pressure. For example, fluid can be moved through any of the systems described herein using a pump, gravitational force, centrifugal force, or mechanical pressure. Additional methods for flowing a fluid through any of the systems described herein are well known in the art.

Methods of Culturing a Mammalian Cell

In a method that is exemplary of those described herein, a multi-well plate is first provided. A first liquid culture medium is added to the well(s) such that the medium occupies between about 5% and about 80% (e.g., between about 5% to about 75%, between about 5% to about 70%, between about 5% to about 65%, between about 5% to about 60%, between about 5% to about 55%, between about 5% to about 50%, between about 5% to about 45%, between about 5% to about 40%, between about 5% and about 35%, between about 5% and about 30%, between about 10% and about 80%, between about 10% and about 75%, between about 10% and about 70%, between about 10% and about 65%, between about 10% and about 60%, between about 10% and about 55%, between about 10% and about 50%, between about 10% and about 45%, between about 10% and about 40%, between about 10% and about 35%, between about 15% and about 80%, between about 15% and about 75%, between about 15% and about 70%, between about 15% and about 65%, between about 15% and about 60%, between about 15% and about 55%, between about 15% and about 50%, between about 15% and about 45%, between about 15% and about 40%, between about 20% and about 80%, between about 20% and about 75%, between about 20% and about 70%, between about 20% and about 65%, between about 20% and about 60%, between about 20% and about 55%, between about 20% and about 50%, between about 20% and about 45%, between about 25% and about 80%, between about 25% and about 75%, between about 25% and about 70%, between about 25% and about 65%, between about 25% and about 60%, between about 25% and about 55%, or between about 25% and about 50%) of the volume of the well. At least one mammalian cell is added to the first liquid culture medium, i.e., either before the medium is added to the well or afterward. The multi-well plate is incubated for a period of time at about 31° C. to about 40° C. and agitated, e.g., on a rotary shaking device, at about 300 RPM to about 600 RPM (e.g., any of the exemplary ranges of agitation described herein). The cells can be incubated, for example, in an incubator, such as a shake incubator with throw (orbit) diameter from about 3 mm to about 50 mm. During incubation, continuously or periodically over the period of time, a first volume of the first liquid culture medium (e.g., containing any mammalian cell concentration, e.g., a first volume of first liquid culture medium which is or is made substantially free of mammalian cells) is removed, and a second volume of a second liquid culture medium is added to the first liquid culture medium. Typically, the first and the second volumes are roughly equal, but can vary by a small amount, e.g., by about 1% to about 10% (e.g., about 1% to about 8%, about 1% to about 5%, or about 1% and about 3%) when the first and second volumes are compared. In some embodiments, the second volume of the second liquid culture medium added is less (e.g., at most about 1%, 2%, 3%, 4%, 5%, 6%, 7%, 8%, 9%, or 10% less) than the first volume of the first liquid culture medium removed. As is known in the art, the term incubating can include short periods of time (e.g., at most 1 minute, at most 2 minutes, at most 3 minutes, at most 4 minutes, at most 5 minutes, at most 10 minutes, at most 20 minutes, at most 30 minutes, at most 40 minutes, at most 50 minutes, or at most 1 hour) in which a multi-well plate containing the mammalian cell and liquid culture medium is removed from an incubator in order to remove the first volume of the first liquid culture medium and add the second volume of the second liquid culture medium. In some examples, the term incubating does not include short periods of time in which a multi-well plate containing the mammalian cell and liquid culture medium is removed from an incubator in order to remove the first volume of the first liquid culture medium and add the second volume of the second liquid culture medium (e.g., through the use of a multi-well culture plate system described herein).

Various non-limiting examples of each aspect of these culturing methods are described below. The exemplary aspects of the methods provided herein can be used in any combination without limitation.

Mammalian Cells

The methods provided herein can be used to culture a variety of different mammalian cells. The mammalian cell can be, e.g., a cell that grows in suspension or can be an adherent cell. Non-limiting examples of mammalian cells that can be cultured using any of the methods described herein include: Chinese hamster ovary (CHO) cells, Sp2.0, myeloma cells (e.g., NS/0), B-cells, hybridoma cells, T-cells, human embryonic kidney (HEK) cells (e.g, HEK 293E and HEK 293F), African green monkey kidney epithelial cells (Vero) cells, and Madin-Darby Canine (Cocker Spaniel) kidney epithelial cells (MDCK) cells. Additional mammalian cells that can be cultured using the methods described herein are known in the art.

The mammalian cell can contain a recombinant nucleic acid (e.g., a nucleic acid stably integrated in the mammalian cell's genome) that encodes a recombinant protein. Non-limiting examples of recombinant nucleic acids that encode exemplary recombinant proteins are described below, as are recombinant proteins that are producible using the methods described herein. In some instances, the mammalian cell disposed in the multi-well plate for culturing is derived from a larger culture. For example, the mammalian cell in the multi-well plate can be derived from a large-scale bioreactor culture, i.e., a satellite culture can be prepared using the methods.

Culture Media

Liquid culture media are known in the art. The first and/or second tissue culture medium can be supplemented with a mammalian serum (e.g., fetal calf serum and bovine serum), and/or a growth hormone or growth factor (e.g., insulin, transferrin, and epidermal growth factor). Alternatively or in addition, the first and/or second liquid culture medium can be a chemically-defined liquid culture medium, an animal-derived component free liquid culture medium, a serum-free liquid culture medium, a serum-containing liquid culture medium, or a protein-free liquid culture medium. Non-limiting examples of chemically-defined liquid culture media, animal-derived component free liquid culture media, serum-free liquid culture media, and serum-containing liquid culture media are commercially available.

A liquid culture medium typically contains an energy source (e.g., a carbohydrate, such as glucose), essential amino acids (e.g., the basic set of twenty amino acids plus cysteine), vitamins and/or other organic compounds required at low concentrations, free fatty acids, and/or trace elements. The first and/or second liquid culture medium can, if desired, be supplemented with, e.g., a mammalian hormone or growth factor (e.g., insulin, transferrin, or epidermal growth factor), salts and buffers (e.g., calcium, magnesium, and phosphate salts), nucleosides and bases (e.g., adenosine, thymidine, and hypoxanthine), protein and tissue hydrolysates, and/or any combination of these additives.

Non-limiting examples of liquid culture media that are particularly useful in the presently described methods include, e.g., CD CHO, Opti CHO, and Forti CHO (all available from Life Technologies; Grand Island, N.Y.), Hycell CHO medium (Thermo Fisher Scientific, Inc.; Waltham, Mass.), Ex-cell CD CHO Fusion medium (Sigma-Aldrich Co.; St. Louis, Mo.), and PowerCHO medium (Lonza Group, Ltd.; Basel, Switzerland). Medium components that also may be useful in the present methods include, but are not limited to, chemically-defined (CD) hydrolysates, e.g., CD peptone, CD polypeptides (two or more amino acids), and CD growth factors. Additional examples of liquid tissue culture medium and medium components are known in the art.

In some examples of any of the methods described herein, the mammalian cell is suspended in about 100 µL to about 25 mL (e.g., about 100 µL to about 20 mL, about 100 µL to about 15 mL, about 100 µL to about 10 mL, about 100 µL to about 8 mL, about 100 µL to about 6 mL, about 100 µL to about 4 mL, about 100 µL to about 3 mL, about 100 µL to about 2.5 mL, about 100 µL to about 2.0 mL, about 100 µL to about 1.5 mL, about 100 µL to about 1.0 mL, about 100

μL to about 800 μL, about 100 μL to about 600 μL, about 100 μL to about 500 μL, about 100 μL to about 400 μL, about 100 μL to about 300 μL, about 100 μL to about 250 μL, about 100 μL to about 200 μL, about 150 μL to about 25 mL, about 150 μL to about 20 mL, about 150 μL to about 15 mL, about 150 μL to about 10 mL, about 150 μL to about 8 mL, about 150 μL to about 6 mL, about 150 μL to about 4 mL, about 150 μL to about 3 mL, about 150 μL to about 2.5 mL, about 150 μL to about 2.0 mL, about 150 μL to about 1.5 mL, about 150 μL to about 1.0 mL, about 150 μL to about 800 μL, about 150 μL to about 600 μL, about 150 μL to about 500 μL, about 150 μL and about 400 μL, about 150 μL to about 300 μL, about 150 μL to about 200 μL, about 250 μL to about 25 mL, about 250 μL to about 20 mL, about 250 μL to about 15 mL, about 250 μL to about 10 mL, about 250 μL to about 8 mL, about 250 μL to about 6 mL, about 250 μL to about 5 mL, about 250 μL to about 4 mL, about 250 μL to about 3 mL, about 250 μL to about 2.5 mL, about 250 μL to about 2 mL, about 250 μL to about 1 mL, about 500 μL to about 25 mL, about 500 μL to about 20 mL, about 500 μL to about 15 mL, about 500 μL to about 10 mL, about 500 μL to about 8 mL, about 500 μL to about 6 mL, about 500 μL to about 5 mL, about 500 μL to about 4 mL, about 500 μL to about 3 mL, about 500 μL to about 2.5 mL, about 500 μL to about 2 mL, about 500 μL to about 1 mL, about 1 mL to about 25 mL, about 1 mL to about 20 mL, about 1 mL to about 15 mL, about 1 mL to about 10 mL, about 1 mL to about 8 mL, about 1 mL to about 6 mL, about 1 mL to about 5 mL, about 1 mL to about 4 mL, about 1 mL to about 3 mL, about 1 mL to about 2.5 mL, or about 1 mL to about 2 mL) of the first culture medium.

Skilled practitioners will appreciate that the first liquid culture medium and the second liquid culture medium described herein can be the same type of media or different media.

Microcarriers

In some examples where the mammalian cell is an adherent cell, the first and/or second liquid culture medium include a plurality of microcarriers. For example, the well can contain a final concentration of microcarriers of, e.g., about 1.0 g/L to about 15.0 g/L, (e.g., a final concentration in the shake flask of between about 1.0 g/L to about 2.5 g/L, about 1.0 g/L to about 2.0 g/L, about 1.0 g/L to about 1.75 g/L, about 1.0 g/L to about 1.5 g/L, about 1.0 g/L to about 1.25 g/L, about 2.5 g/L to about 5.0 g/L, about 5.0 g/L to about 7.5 g/L, about 7.5 g/L to about 10.0 g/L, about 10.0 g/L to about 12.5 g/L, about 12.5 g/L to about 15.0 g/L, about 1.0 g/L to about 5.0 g/L, about 5.0 g/L to about 10.0 g/L, about 10.0 g/L to about 15.0 g/L, about 2.5 g/L to about 3.5 g/L, about 3.0 g/L to about 4.0 g/L, about 4.0 g/L to about 5.0 g/L, about 5.0 g/L to about 6.0 g/L, about 6.0 g/L to about 7.0 g/L, about 7.0 g/L to about 8.0 g/L, about 8.0 g/L to about 9.0 g/L, about 9.0 g/L to about 10.0 g/L, about 10.0 g/L to about 11.0 g/L, about 11.0 g/L to about 12.0 g/L, about 12.0 g/L to about 13.0 g/L, about 13.0 g/L to about 14.0 g/L, or about 14.0 g/L to about 15.0 g/L).

In some embodiments, the plurality of microcarriers can have an average diameter of between about 20 μm to about 1 mm (e.g., between about 20 μm and about 250 μm, between about 100 μm to about 250 μm, between about 150 μm to about 250 μm, between about 250 μm and 500 μm, between about 200 μm to about 300 μm, between about 750 μm and 1 mm, between about 200 μm to about 800 μm, between about 200 μm and about 500 μm, or between about 500 μm and about 800 μm), where the microcarriers have a surface that is permissive or promotes attachment of a mammalian cell (e.g., any of the mammalian cells described herein or known in the art). In some examples, a microcarrier can contain one or more pores (e.g., one or more pores with an average diameter of about 10 μm to about 100 μm (e.g., between about 10 μm and 20 μm, about 20 μm to about 30 μm, about 30 μm to about 40 μm, about 50 μm to about 60 μm, about 60 μm to about 70 μm, about 70 μm to about 80 μm, about 80 μm to about 90 μm, about 90 μm to about 100 μm, about 10 μm to about 45 μm, about 45 μm to about 80 μm, about 25 μm to about 35 μm, or about 30 μm)). In some embodiments, the surface of the plurality of microcarriers and/or the surface of the one or more pores in the plurality of microcarriers are coated with an agent that promotes the attachment of a mammalian cell to the microcarrier (e.g., attachment to the outer surface of the microcarriers and/or the surface of the pores in the microcarrier). Examples of such agents that can be used to promote the attachment of a mammalian cell include, but are not limited to, gelatin, collagen, poly-L-ornithine, polystyrene, and laminin.

In some examples, the microcarriers have an average effective cell binding surface area of between about 0.5 m$^2$/g dry and 2.0 m$^2$/g dry (e.g., between about 0.75 m$^2$/g dry and 1.25 m$^2$/dry, between about 1.0 m$^2$/g dry and about 1.5 m$^2$/dry, between about 1.25 m$^2$/dry and about 1.5 m$^2$/dry, about 1.5 m$^2$/dry and about 2.0 m$^2$/dry, or about 1.1 m$^2$/dry). In some examples, the microcarriers have an average volume of about 10 mL/g dry to about 70 mL/g dry (e.g., about 10 mL/g dry to about 20 mL/g dry, about 20 mL/g dry to about 30 mL/g dry, about 30 mL/g dry to about 40 mL/g dry, about 40 mL/g dry to about 50 mL/g dry, about 50 mL/g dry to about 60 mL/g dry, about 60 mL/g dry to about 70 mL/g dry, about 10 mL/g dry to about 40 mL/g dry, about 30 mL/g dry to about 40 mL/g dry, about 40 mL/g dry to about 70 mL/g dry, or about 40 mL/g dry). In some embodiments, the average relative density of the microcarriers is between 0.8 g/mL to about 1.2 g/mL (e.g., about 0.8 g/mL to about 0.9 g/mL, about 0.9 g/mL to about 1.0 g/mL, about 1.0 g/mL to about 1.1 g/mL, about 1.0 g/mL, about 1.1 g/mL to about 1.2 g/mL, about 0.95 g/mL to about 1.05 g/mL, or about 1.03 g/mL).

In some embodiments, the microcarriers are approximately spherical or ellipsoidal in shape. In other examples, the microcarriers have an abraded or rough surface with small protuberances that increase the total outer surface area of the microcarrier. In some embodiments, the microcarriers have a network structure. In some examples, the microcarriers are hygroscopic. In some examples, the microcarriers contain cellulose.

In some embodiments, the microcarriers have an outer surface and/or the microcarrier pores have a surface that is positively charged (e.g., positively charged due to the presence of N,N,-diethylaminoethyl groups). In some examples, the microcarriers have a network or net-like or web-like structure. The microcarriers can have an average charge density of about 0.5 me/g to about 2.5 me/g (e.g., about 0.5 me/g to about 1.5 meq/g, about 0.75 meq/g to about 1.25 meq/g, about 1.1 meq/g, about 1.5 meq/g to about 2.5 meq/g, about 1.5 meq/g to about 2.0 meq/g, about 1.8 meq/g, about 0.5 meq/g to about 1.0 meq/g, or about 1.0 meq/g to about 1.5 meq/g).

In some instances, the microcarrier can contain a natural polymer and/or a synthetic polymer. Non-limiting examples of synthetic polymers include polyethylene glycol (PEG), polyethylene oxide, polyethyleneimine, diethyleneglycol, triethyleneglycol, polyalkalene glycol, polyalkaline oxide, polyvinyl alcohol, sodium polyphosphate, polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyglycerine, polyaspartamide, polyoxyethlene-polyoxypropylene copolymer (poloxamer), carboxylic acids (e.g., acrylic acid, methacrylic acid, itaconic acid, and maleic acid), polyoxyethylenes, polyethyleneoxide, unsaturated ethylenic monodicarboxylic acids, polylactic acid (PLA), polypropylene oxide, poly(lactide-co-glycolide) (PLGA), poly(epsilon-caprolactone), poly(ethylethylene), polybutadiene, polyglycolide, polymethylacrylate, polyvinylbutylether, polystyrene, polycyclopentadienylmethylnorbornene, polyethylenepropylene, polyethylethylene, polyisobutylene, polysiloxane, methyl acrylate, ethyl acrylate, propyl acrylate, n-butyl acrylate, isobutyl acrylate, 2-ethyl acrylate, t-butyl acrylate, methacrylates (e.g., ethyl methacrylate, n-butyl methacrylate, and isobutyl methacrylate), acrylonitriles, methacrylonitrile, vinyls (e.g., vinyl acetate, vinylversatate, vinylpropionate, vinylformamide, vinylacetamide, vinylpyridines, and vinyllimidazole), aminoalkyls (e.g., aminoalkylacrylates, aminoalkylsmethacrylates, and aminoalkyl(meth)acrylamides), styrenes, polyalkalene glycol, polyalkaline oxide, and lactic acids. Non-limiting examples of natural polymers include cellulose, lecithin, and hyaluronic acid. A microcarrier can contain a mixture of different polymers (e.g., any combination of one or more polymers described herein or known in the art) in the same or different ratios. Any of the microcarriers described herein can contain a core containing one or more polymers (e.g., any of the polymers described herein or known in the art) and an outer layer that contains one or more different polymers (e.g., any of the polymers described herein or known in the art).

Non-limiting exemplary microcarriers that can be used in any of the methods described herein include CytoPore™ 1 and CytoPore™ 2 (available from GE Healthcare, Life Sciences, Piscataway, N.J.). Additional examples of microcarriers that can be used in any of the methods described herein are publicly available and known in the art.

Multi-Well Plates

A variety of multi-plates are known in the art and can be used in any of the methods described herein. For example, a multi-well plate can be a 2-well plate, 4-well plate, a 6-well plate, an 8-well plate, a 9-well plate, a 10-well plate, a 12-well plate, a 15-well plate, a 18-well plate, a 20-well plate, a 24-well plate, a 36-well plate, a 48-well plate, a 60-well plate, a 72-well plate, or 96-well plate. In some examples, the well has a volume (an internal volume) of between about 0.3 mL and about 25 mL (e.g., between about 0.3 mL and about 24 mL, between about 0.3 mL and about 22 mL, between about 0.3 mL and about 20 mL, between about 0.3 mL and about 18 mL, between about 0.3 mL and about 16 mL, between about 0.3 mL and about 14 mL, between about 0.3 mL and about 12 mL, between about 0.3 mL and about 10 mL, between about 0.3 mL and about 8 mL, between about 0.3 mL and about 6 mL, between about 0.3 mL and about 5 mL, between about 0.3 mL and about 4 mL, between about 0.3 mL and about 3 mL, between about 0.3 mL and about 2 mL, between about 0.3 mL and about 1 mL, between about 0.5 mL and about 25 mL, between about 0.5 mL and about 24 mL, between about 0.5 mL and about 22 mL, between about 0.5 mL and about 0.5 mL, between about 20 mL, between about 0.5 mL and about 18 mL, between about 0.5 mL and about 16 mL, between about 0.5 mL and about 14 mL, between about 0.5 mL and about 12 mL, between about 0.5 mL and about 10 mL, between about 0.5 mL and about 8 mL, between about 0.5 mL and about 6 mL, between about 0.5 mL and about 5 mL, between about 0.5 mL and about 4 mL, between about 0.5 mL and about 3 mL, between about 0.5 mL and about 2 mL, between about 0.5 mL and about 1 mL, between about 1 mL and about 25 mL, between about 1 mL and about 24 mL, between about 1 mL and about 22 mL, between about 1 mL and about 20 mL, between about 1 mL and about 18 mL, between about 1 mL and about 16 mL, between about 1 mL and about 14 mL, between about 1 mL and about 12 mL, between about 1 mL and about 10 mL, between about 1 mL and about 8 mL, between about 1 mL and about 7 mL, between about 1 mL and about 6 mL, between about 1 mL and about 5 mL, between about 1 mL and about 4 mL, between about 1 mL and about 3.5 mL, between about 1 mL and about 3 mL, between about 1 mL and about 2.5 mL, between about 1 mL and about 2 mL, between about 1 mL and about 1.5 mL, between about 1.5 mL and about 25 mL, between about 1.5 mL and about 24 mL, between about 1.5 mL and about 22 mL, between about 1.5 mL and about 20 mL, between about 1.5 mL and about 18 mL, between about 1.5 mL and about 16 mL, between about 1.5 mL and about 14 mL, between about 1.5 mL and about 12 mL, between about 1.5 mL and about 10 mL, between about 1.5 mL and about 8 mL, between about 1.5 mL and about 6 mL, between about 1.5 mL and about 5 mL, between about 1.5 mL and about 4 mL, between about 1.5 mL and about 3.5 mL, between about 1.5 mL and about 3 mL, between about 1.5 mL and about 2.5 mL, between about 1.5 mL to about 2.0 mL, between about 2 mL and about 25 mL, between about 2 mL and about 24 mL, between about 2 mL and about 22 mL, between about 2 mL and about 20 mL, between about 2 mL and about 18 mL, between about 2 mL and about 16 mL, between about 2 mL and about 14 mL, between about 2 mL and about 12 mL, between about 2 mL and about 10 mL, between about 2 mL and about 8 mL, between about 2 mL and about 6 mL, or between about 2 mL and about 5 mL).

In some examples, the multi-well plate is a deep-well plate. For example, internal height of a well in a deep-well plate can be between 1 cm and about 12 cm (e.g., between about 1 cm and about 11 cm, between about 1 cm and about 10 cm, between about 1 cm and about 9 cm, between about 1 cm and about 8 cm, between about 1 cm and about 7 cm, between about 1 cm and about 6 cm, between about 1 cm and about 5 cm, between about 1 cm and about 4 cm, between about 1 cm and about 3 cm, between about 1.2 cm and about 12 cm, between about 1.2 cm and about 11 cm, between about 1.2 cm and about 10 cm, between about 1.2 cm and about 9 cm, between about 1.2 cm and about 8 cm, between about 1.2 cm and about 7 cm, between about 1.2 cm and about 6 cm, between about 1.2 cm and about 5 cm, between about 1.2 cm and about 4 cm, between about 1.2 cm and about 3 cm, between about 1.5 cm and about 11 cm, between about 1.5 cm and about 10 cm, between about 1.5 cm and about 9 cm, between about 1.5 cm and about 8 cm, between about 1.5 cm and about 7 cm, between about 1.5 cm and about 6 cm, between about 1.5 cm and about 5 cm, between about 1.5 cm and about 4 cm, between about 1.5 cm and about 3 cm, between about 2 cm and about 12 cm, between about 2 cm and about 11 cm, between about 2 cm and about 10 cm, between about 2 cm and about 9 cm, between about 2 cm and about 8 cm, between about 2 cm and about 7 cm, between about 2 cm and about 6 cm, between about 2 cm and about 5 cm, between about 2 cm and about 4 cm, between about 2 cm and about 3 cm, between about 2.5 cm and about 12 cm, between about 2.5 cm and about 11 cm, between about 2.5 cm and about 10 cm, between about 2.5 cm and about 9 cm, between about 2.5 cm and about 8 cm, between about 2.5 cm and about 7 cm, between about 2.5 cm and about 6 cm, between about 2.5 cm and about 5 cm, between about 2.5 cm and about 4 cm, between about 3 cm and about 12 cm, between about 3 cm and about 11 cm, between about 3 cm and about 10 cm, between about 3 cm and about 9 cm, between about 3 cm and about 8 cm, between about 3 cm and about 7 cm, between about 3 cm and about 6 cm, between about 3 cm and about 5 cm, between about 4 cm and about 12 cm, between about 4 cm and about 11 cm, between about 4 cm and about 10 cm, between about 4 cm and about 9 cm, between about 4 cm and about 8 cm, between about 4 cm and about 7 cm, between about 4 cm and about 6 cm, between about 5 cm and about 12 cm, between about 5 cm and about 11 cm, between about 5 cm and about 10 cm, between about 5 cm and about 9 cm, between about 5 cm and about 8 cm, or between about 5 cm and about 7 cm).

In some examples, the well (e.g., in a deep-well multi-well plate) can have a flat bottom (also called square bottom), a round bottom (also called hemispherical bottom), a cone bottom, or a pyramid bottom. In some embodiments, the diameter of any of the wells described herein can be between about 4.0 mm and about 50 mm (e.g., between about 4.0 mm and about 45 mm, between about 4.0 mm and about 40 mm, between about 4.0 mm and about 35 mm, between about 4.0 mm and about 30 mm, between about 4.0 mm and about 25 mm, between about 4.0 mm and about 20 mm, between about 4.0 mm and about 15 mm, between about 4.0 mm and about 10 mm, between about 6.0 mm and about 50 mm, between about 6.0 mm and about 45 mm, between about 6.0 mm and about 40 mm, between about 6.0 mm and about 35 mm, between about 6.0 mm and about 30 mm, between about 6.0 mm and about 25 mm, between about 6.0 mm and about 25 mm, between about 6.0 mm and about 20 mm, between about 6.0 mm and about 15 mm, between about 6.0 mm and about 10 mm, between about 8 mm and about 50 mm, between about 8 mm and about 45 mm, between about 8 mm and about 40 mm, between about 8 mm and about 35 mm, between about 8 mm and about 30 mm, between about 8 mm and about 25 mm, between about 8 mm and about 20 mm, between about 8 mm and about 15 mm, between about 10 mm and about 50 mm, between about 10 mm and about 45 mm, between about 10 mm and about 40 mm, between about 10 mm and about 35 mm, between about 10 mm and about 30 mm, between about 10 mm and about 25 mm, between about 10 mm and about 20 mm, between about 15 mm and about 50 mm, between about 15 mm and about 45 mm, between about 15 mm and about 40 mm, between about 15 mm and about 35 mm, between about 15 mm and about 30 mm, between about 15 mm and about 25 mm, or between about 15 mm and about 20 mm).

In some examples, the multi-well plate is sealed (e.g., sealed with a gas-permeable disposable membrane or a gas-permeable silicone layer). Non-limiting examples of materials used to seal a multi-well plate are described in the Examples. Additional materials used to seal a multi-well plate are well known in the art.

The interior surface of the well(s) may have at least one coating (e.g., at least one coating of gelatin, collagen, poly-L-ornithine, polystyrene, and laminin). Additional examples of multi-well plates (e.g., different shapes and dimensions of well(s)) and interior surface coatings of well(s) are known in the art and can be used in the present methods.

Agitation

The methods described herein require the rotary agitation of the culture containing the mammalian cell and the first and/or second liquid culture medium. The rotary agitation can occur at a frequency of about 300 RPM to about 600 RPM (e.g., about 300 RPM to about 580 RPM, about 300 RPM to about 560 RPM, about 300 RPM to about 540 RPM, about 300 RPM to about 520 RPM, about 300 RPM to about 500 RPM, about 300 RPM to about 480 RPM, about 300 RPM to about 460 RPM, about 300 RPM to about 440 RPM, about 300 RPM to about 420 RPM, about 300 RPM to about 400 RPM, about 300 RPM to about 380 RPM, about 300 RPM to about 360 RPM, about 320 RPM to about 600 RPM, about 320 RPM to about 580 RPM, about 320 RPM to about 560 RPM, about 320 RPM to about 540 RPM, about 320 RPM to about 520 RPM, about 320 RPM to about 500 RPM, about 320 RPM to about 480 RPM, about 320 RPM to about 460 RPM, about 320 RPM to about 440 RPM, about 320 RPM to about 420 RPM, about 320 RPM to about 400 RPM, about 320 RPM to about 380 RPM, about 330 RPM to about 600 RPM, about 330 RPM to about 580 RPM, about 330 RPM to about 560 RPM, about 330 RPM to about 540 RPM, about 330 RPM to about 520 RPM, about 330 RPM to about 500 RPM, about 330 RPM to about 480 RPM, about 330 RPM to about 460 RPM, about 330 RPM to about 440 RPM, about 330 RPM to about 420 RPM, about 330 RPM to about 400 RPM, about 330 RPM to about 380 RPM, about 340 RPM to about 600 RPM, about 340 RPM to about 580 RPM, about 340 RPM to about 560 RPM, about 340 RPM to about 540 RPM, about 340 RPM to about 520 RPM, about 340 RPM to about 500 RPM, about 340 RPM to about 480 RPM, about 340 RPM to about 460 RPM, about 340 RPM to about 440 RPM, about 340 RPM to about 420 RPM, about 340 RPM to about 400 RPM, about 360 RPM to about 600 RPM, about 360 RPM to about 580 RPM, about 360 RPM to about 560 RPM, about 360 RPM to about 540 RPM, about 360 RPM to about 520 RPM, about 360 RPM to about 500 RPM, about 360 RPM to about 480 RPM, about 360 RPM to about 460 RPM, about 360 RPM to about 440 RPM, about 360 RPM to about 420 RPM, about 380 RPM to about 600 RPM, about 380 RPM to about 580 RPM, about 380 RPM to about 560 RPM, about 380 RPM to about 540 RPM, about 380 RPM to about 520 RPM, about 380 RPM to about 500 RPM, about 380 RPM to about 480 RPM, about 380 RPM to about 460 RPM, about 380 RPM to about 440 RPM, about 400 RPM to about 600 RPM, about 400 RPM to about 580 RPM, about 400 RPM to about 560 RPM, about 400 RPM to about 540 RPM, about 400 RPM to about 520 RPM, about 400 RPM to about 500 RPM, about 400 RPM to about 480 RPM, or about 400 RPM to about 460 RPM) (e.g., in an incubator, such as a shake incubator with throw (orbit) diameter from about 3 mm to about 50 mm).

As can be appreciated in the art, the level of agitation (e.g., RPM speed) can be varied depending upon the size and shape of the well (e.g., one or more of the diameter, shape, and height of the well) and the throw (orbit) diameter of the incubator that is used to perform the incubating. For example, a smaller throw (orbit) diameter can require a higher level of agitation (e.g., a higher RPM speed), while a larger throw (orbit) diameter can require a lower level of agitation (e.g., a lower RPM speed) to achieve a similar level of fluid sheer force and dissolved $O_2$ concentration. In another example, a well having a larger diameter can require a lower RPM speed, while a well having a smaller diameter can require a higher RPM speed to achieve a similar level of fluid sheer force and dissolved $O_2$ concentration.

In some embodiments, the incubating is performed using a shake tube incubator with a throw (orbit) diameter of between about 3 mm to about 50 mm (e.g., between about 3 mm and about 25 mm, or between about 25 mm and about 50 mm) and an agitation of between about 320 RPM and about 500 RPM (e.g., between about 320 RPM and about 480 RPM, between about 320 RPM and about 460 RPM, about 320 RPM and about 400 RPM, between about 320 RPM and about 380 RPM, between about 320 RPM and about 360 RPM, between about 320 RPM and about 350 RPM, between about 320 RPM and about 340 RPM, between about 330 RPM and about 500 RPM, between about 330 RPM and about 480 RPM, between about 330 RPM and about 460 RPM, between about 330 RPM and about 440 RPM, between about 330 RPM and about 420 RPM, between about 330 RPM and about 400 RPM, between about 330 RPM and about 380 RPM, between about 330 RPM and about 370 RPM, between about 330 RPM and about 360 RPM, between about 330 RPM and about 350 RPM, between about 340 RPM and about 500 RPM, between about 340 RPM and about 480 RPM, 340 RPM and about 460 RPM, between about 340 RPM and about 440 RPM, between about 340 RPM and about 420 RPM, between about 340 RPM and about 400 RPM, between about 340 RPM and about 380 RPM, between about 340 RPM and about 370 RPM, between about 340 RPM and about 360 RPM, between about 350 RPM and about 500 RPM, between about 350 RPM and about 480 RPM, between about 350 RPM and about 460 RPM, between about 350 RPM and about 440 RPM, between about 350 RPM and about 420 RPM, between about 350 RPM and about 400 RPM, between about 350 RPM and about 390 RPM, between about 350 RPM and about 380 RPM, between about 350 RPM and about 370 RPM, between about 360 RPM and about 500 RPM, between about 360 RPM and about 480 RPM, between about 360 RPM and about 460 RPM, between about 360 RPM and about 440 RPM, between about 360 RPM and about 420 RPM, between about 360 RPM and about 400 RPM, between about 360 RPM and about 380 RPM, or between about 400 RPM and about 500 RPM). Rotary agitation can be performed, e.g., using rotary circular shaking or rotary ellipsoidal shaking. The agitation can be performed continuously or periodically.

The rotary agitation of the multi-well plate can result in essentially the same fluid sheer force and dissolved oxygen ($O_2$) concentration as that achieved in a square-bottom well having a diameter of between about 6.0 mm and about 35 mm (e.g., between about 6.0 mm and about 30 mm, between about 6.0 mm and about 25 mm, between about 6.0 mm and about 20 mm, between about 6.0 mm and about 15 mm, between about 10 mm and about 35 mm, between about 10 mm and about 30 mm, between about 10 mm and about 25 mm, between about 10 mm and about 20 mm, between about 15 mm and about 35 mm, between about 15 mm and about 30 mm, between about 15 mm and about 25 mm, between about 20 mm and about 35 mm, between about 20 mm and about 30 mm, or between about 25 mm and about 35 mm) and a height of between about 40 mm and about 50 mm (e.g., between about 40 mm and about 45 mm or between about 45 mm and about 50 mm) containing a liquid culture medium that occupies about 10% to about 40% (e.g., about 10% to about 35%, about 10% to about 30%, about 10% to about 25%, about 10% to about 20%, about 10% to about 15%, between about 15% to about 40%, about 15% to about 35%, about 15% to about 30%, about 15% to about 25%, about 15% to about 20%, about 20% to about 40%, about 20% to about 35%, about 20% to about 30%, about 20% to about 25%, about 25% to about 40%, about 25% to about 35%, about 25% to about 30%, about 30% to about 40%, about 30% to about 35%, or between about 35% and about 40%) volume of the well is incubated at a temperature of about 31° C. to about 40° C., and agitated at a frequency of about 320 RPM to about 450 RPM (e.g., about 320 RPM to about 440 RPM, about 320 RPM to about 430 RPM, about 320 RPM to about 420 RPM, about 320 RPM to about 410 RPM, about 320 RPM to about 400 RPM, about 320 RPM to about 390 RPM, about 320 RPM to about 380 RPM, about 320 RPM to about 370 RPM, about 320 RPM to about 360 RPM, about 320 RPM to about 350 RPM, about 320 RPM to about 340 RPM, about 320 RPM to about 330 RPM, about 330 RPM to about 450 RPM, about 330 RPM to about 440 RPM, about 330 RPM to about 430 RPM, about 330 RPM to about 420 RPM, about 330 RPM to about 410 RPM, about 330 RPM to about 400 RPM, about 330 RPM to about 390 RPM, about 330 RPM to about 380 RPM, about 330 RPM to about 370 RPM, about 330 RPM to about 360 RPM, about 330 RPM to about 350 RPM, about 330 RPM to about 340 RPM, about 340 RPM to about 450 RPM, about 340 RPM to about 440 RPM, about 340 RPM to about 430 RPM, about 340 RPM to about 420 RPM, about 340 RPM to about 410 RPM, about 340 RPM to about 400 RPM, about 340 RPM to about 390 RPM, about 340 RPM to about 380 RPM, about 340 RPM to about 370 RPM, about 340 RPM to about 360 RPM, about 340 RPM to about 350 RPM, about 350 RPM to about 450 RPM, about 350 RPM to about 440 RPM, about 350 RPM to about 430 RPM, about 350 RPM to about 420 RPM, about 350 RPM to about 410 RPM, about 350 RPM to about 400 RPM, about 350 RPM to about 390 RPM, about 350 RPM to about 380 RPM, about 350 RPM to about 370 RPM, about 350 RPM to about 360 RPM, about 360 RPM to about 450 RPM, about 360 RPM to about 440 RPM, about 360 RPM to about 430 RPM, about 360 RPM to about 420 RPM, about 360 RPM to about 410 RPM, about 360 RPM to about 400 RPM, about 360 RPM to about 390 RPM, about 360 RPM to about 380 RPM, about 360 RPM to about 370 RPM, about 370 RPM to about 450 RPM, about 370 RPM to about 430 RPM, about 370 RPM to about 410 RPM, about 370 RPM to about 390 RPM, about 390 RPM to about 450 RPM, about 390 RPM to about 430 RPM, about 390 RPM to about 410 RPM, about 410 RPM to about 450 RPM, about 410 RPM to about 430 RPM, or about 430 RPM to about 450 RPM).

The rotary agitation can be performed using a humidified atmosphere controlled incubator (e.g., at a humidity of greater than 20%, 30%, 40%, 50%, 60%, 70%, 75%, 80%, 85%, 90%, or 95%, or a humidity of 100%) with a mechanical device that provides the agitation of one or more of the multi-well plates containing the mammalian cell and a liquid culture medium (e.g., the first and/or second liquid culture medium).

Temperature

The culturing methods described herein can be performed at a temperature of about 31° C. to about 40° C. Skilled practitioners will appreciate that the temperature can be changed at specific time point(s) in the culturing method, e.g., on an hourly or daily basis. For example, the temperature can be changed or shifted (e.g., increased or decreased) at about one day, two days, three days, four days, five days, six days, seven days, eight days, nine days, ten days, eleven days, twelve days, fourteen days, fifteen days, sixteen days, seventeen days, eighteen days, nineteen days, or about twenty days or more after the initial seeding of the well with the mammalian cell). For example, the temperature can be shifted upwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20 degrees C.). For example, the temperature can be shifted downwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20° C.).

Culture Medium Removal and Replacement

The methods described herein include removing from the well(s) a first volume of a first liquid culture medium (e.g., containing any concentration of mammalian cells, e.g., a first volume of a first liquid culture medium that is substantially free of cells), and adding to the first liquid culture medium a second volume of a second liquid culture medium. Removal and adding can be performed simultaneously or sequentially, or a combination of the two. Further, removal and adding can be performed continuously (e.g., at a rate that removes and replaces a volume of between 0.1% to 700% (e.g., between 1% and 600%, between 1% and 500%, between 1% and 400%, between 1% and 350%, between 1% and 300%, between 1% and 250%, between 1% and 100%, between 100% and 200%, between 5% and 150%, between 10% and 50%, between 15% and 40%, between 8% and 80%, or between 4% and 30%) of the volume of the well or the first liquid culture medium volume over any given time period (e.g., over a 24-hour period, over an incremental time period of about 1 hour to about 24 hours, or over an incremental time period of greater than 24 hours)) or periodically (e.g., once every third day, once every other day, once a day, twice a day, three times a day, four times a day, or five times a day), or any combination thereof. Where performed periodically, the volume that is removed or replaced (e.g., within about a 24-hour period, within an incremental time period of about 1 hour to about 24 hours, or within an incremental time period of greater than 24 hours) can be, e.g., between 0.1% to 700% (e.g., between 1% and 700%, between 1% and 600%, between 1% and 500%, between 1% and 400%, between 1% and 300%, between 1% and 200%, between 1% and 100%, between 100% and 200%, between 5% and 150%, between 10% and 50%, between 15% and 40%, between 8% and 80%, or between 4% and 30%) of the volume of the well or the first liquid culture medium volume. The first volume of the first liquid culture medium removed and the second volume of the second liquid culture medium added can in some instances be held approximately the same over each 24-hour period (or, alternatively, an incremental time period of about 1 hour to about 24 hours or an incremental time period of greater than 24 hours) over the entire or part of the culturing period. As is known in the art, the rate at which the first volume of the first liquid culture medium is removed (volume/unit of time) and the rate at which the second volume of the second liquid culture medium is added (volume/unit of time) can be varied. The rate at which the first volume of the first liquid culture medium is removed (volume/unit of time) and the rate at which the second volume of the second liquid culture medium is added (volume/unit of time) can be about the same or can be different.

Alternatively, the volume removed and added can change (e.g., gradually increase) over each 24-hour period (or alternatively, an incremental time period of between 1 hour and about 24 hours or an incremental time period of greater than 24 hours) during the culturing period. Non-limiting examples of methods that include a gradual increase in volumes are described herein. For example the volume of the first liquid culture medium removed and the volume of the second liquid culture medium added within each 24-hour period (or alternatively, an incremental time period of between about 1 hour and above 24 hours or an incremental time period of greater than 24 hours) over the culturing period can be increased (e.g., gradually or through staggered increments) over the culturing period from a volume that is between 0.5% to about 30% of the well volume or the first liquid culture medium volume to about 30% to about 200% of the well volume or the first liquid culture medium volume.

In some embodiments of any of the methods described herein, the multi-well plate is incubated for a period of time greater than 7 days, and on days 1 through 3 of incubation, in each 24-hour period, the first volume of the first liquid culture medium removed and the second volume of the second liquid culture medium added is between about 30% to about 50% of the volume of the first liquid culture medium; on days 4 through 6 of the incubation, the first volume of the first liquid culture medium removed and the second volume of the second liquid culture medium added is between about 30% to about 50% of the volume of the first liquid culture medium; and on day 7 and afterwards of incubation, in each 24-hour period, the first volume of the first liquid culture medium removed and the second volume of the second liquid culture medium added is about 90% to about 150% of the volume of the first liquid culture medium.

In other examples, after about the first 24 to 48 hours of the period of time, in each 24-hour period, the first volume of the first liquid culture medium removed and the second volume of the second liquid culture medium added is about 30% to about 300% (e.g., about 30% to about 280%, about 30% to about 260%, about 30% to about 240%, about 30% to about 220%, about 30% to about 200%, about 30% to about 180%, about 30% to about 160%, about 30% to about 150%, about 30% to about 140%, about 30% to about 120%, about 30% to about 100%, about 30% to about 80%, about 30% to about 60%, about 30% to about 50%, about 40% to about 300%, about 40% to about 280%, about 40% to about 260%, about 40% to about 240%, about 40% to about 220%, about 40% to about 200%, about 40% to about 180%, about 40% to about 160%, about 40% to about 140%, about 40% to about 120%, about 40% to about 100%, about 40% to about 80%, about 40% to about 60%, about 50% to about 300%, about 50% to about 280%, about 50% to about 260%, about 50% to about 240%, about 50% to about 220%, about 50% to about 200%, about 50% to about 180%, about 50% to about 160%, about 50% to about 140%, about 50% to about 120%, about 50% to about 100%, or about 50% to about 80% of the volume of the first liquid culture medium.

Skilled practitioners will appreciate that the first liquid culture medium and the second liquid culture medium can be the same type of media. In other instances, the first liquid culture medium and the second liquid culture medium can be different.

The first volume of the first liquid culture medium can be removed, e.g., by centrifuging (e.g., slow-speed swinging bucket centrifugation) the multi-well plate, and removing the first volume of the first liquid culture that is substantially free of cells from the supernatant. Alternatively or in addition, the first volume of the first liquid culture medium can be removed by seeping or gravity flow of the first volume of the first liquid culture medium through a sterile membrane with a molecular weight cut-off that excludes the mammalian cell. Alternatively or in addition, the first liquid culture medium can be removed ceasing agitation for a period of time of at least 30 seconds (e.g., at least one minute, at least two minutes, at least three minutes, at least four minutes, or at least five minutes) prior to removing the first volume of the first liquid culture medium. The first volume of the first liquid culture medium can be removed manually (e.g., by aspirating or pipetting off the first volume of the first liquid culture medium from the well) or in an automated fashion (e.g., using an automated device or any of the multi-well cell culture plate systems described herein).

The second volume of the second liquid culture medium can be added to the first liquid culture medium, e.g., by perfusion pump. The second liquid culture medium can be added to the first liquid culture medium manually (e.g., by pipetting the second volume of the second liquid culture medium directly onto the first liquid culture medium) or in an automated fashion (e.g., using an automated device or any of the multi-well cell culture plate systems described herein).

In some examples, the first volume of the first liquid culture medium can be removed and the second volume of the second liquid culture medium can be added to the first liquid culture medium using any of the multi-well cell culture plate systems provided herein.

In some instances, removing the first volume of the first liquid culture medium (e.g., a first volume of the first liquid culture medium that is substantially free of mammalian cells) and adding to the first liquid culture medium a second volume of the second liquid culture medium does not occur within at least 1 hour (e.g., within 2 hours, within 3 hours, within 4 hours, within 5 hours, within 6 hours, within 7 hours, within 8 hours, within 9 hours, within 10 hours, within 12 hours, within 14 hours, within 16 hours, within 18 hours, within 24 hours, within 36 hours, within 48 hours, within 72 hours, within 96 hours, or after 96 hours) of the seeding of the well(s) with a mammalian cell.

Some embodiments further include periodically adding an additional volume of second liquid culture medium to each of the plurality of wells in order to offset any decrease in the volume of the first liquid culture medium due to evaporation. For example, such an additional volume of second liquid culture medium can be added to each well, e.g., at least once every 24-hours, at least once every 48-hours, at least once every 72-hours, or at least once every 96-hours. This additional volume of second liquid culture medium can be added manually or in an automated fashion (e.g., using an automated device or using any of the multi-well cell culture plate systems described herein).

$CO_2$

Methods described herein can further include incubating the multi-well plate in an atmosphere containing at most or about 15% $CO_2$ (e.g., at most or about 14% $CO_2$, 12% $CO_2$, 10% $CO_2$, 8% $CO_2$, 6% $CO_2$, 5% $CO_2$, 4% $CO_2$, 3% $CO_2$, 2% $CO_2$, or at most or about 1% $CO_2$). Moreover, any of the methods described herein can include incubating the multi-well plate in a humidified atmosphere (e.g., at least or about 20%, 30%, 40%, 50%, 60%, 70%, 85%, 80%, 85%, 90%, or at least or about 95% humidity, or about 100% humidity).

Exemplary Devices

Non-limiting examples of devices that can be used to perform the culturing methods described herein include: Appropriate Technical Resources (Maryland, USA) distributes INFORS Multiron shake incubator (INFORS; Basel, Switzerland), and Kuhner shake incubator (Kuhner AG; Basel, Switzerland). Non-limiting examples of devices that can be used to perform the culturing methods include a rotary incubator with a throw (orbit) diameter of between about 3 mm to about 50 mm (e.g., between about 1 mm and about 25 mm, or between about 25 mm and about 50 mm) Additional examples of shake incubators and rolling culture incubators are known in the art.

Dissolved $O_2$ and Liquid Sheer Force

Also provided are culturing methods that include culturing in a gradient perfusion process a mammalian cell suspended in a liquid culture medium disposed within a well of a multi-well plate under conditions that generate in the medium a fluid sheer force and dissolved oxygen ($O_2$) concentration that are the same as (or essentially the same as) that achieved in a medium occupying about 10% to about 40% (e.g., about 10% to about 35%, about 10% to about 30%, about 10% to about 25%, about 10% to about 20%, about 10% to about 15%, between about 15% to about 40%, about 15% to about 35%, about 15% to about 30%, about 15% to about 25%, about 15% to about 20%, about 20% to about 40%, about 20% to about 35%, about 20% to about 30%, about 20% to about 25%, about 25% to about 40%, about 25% to about 35%, about 25% to about 30%, about 30% to about 40%, about 30% to about 35%, or between about 35% and about 40%) of the volume of a square-bottom well having a diameter of between about 6.0 mm and about 35 mm (e.g., between about 6.0 mm and about 30 mm, between about 6.0 mm and about 25 mm, between about 6.0 mm and about 20 mm, between about 6.0 mm and about 15 mm, between about 10 mm and about 35 mm, between about 10 mm and about 30 mm, between about 10 mm and about 25 mm, between about 10 mm and about 20 mm, between about 15 mm and about 35 mm, between about 15 mm and about 30 mm, between about 15 mm and about 25 mm, between about 20 mm and about 35 mm, between about 20 mm and about 30 mm, or between about 25 mm and about 35 mm) and a height of between about 40 mm and about 50 mm (e.g., between about 40 mm and about 45 mm or between about 45 mm and about 50 mm), incubated at a temperature of about 31° C. to about 40° C., and agitated at a frequency of about 320 RPM to about 450 RPM (e.g., about 320 RPM to about 440 RPM, about 320 RPM to about 430 RPM, about 320 RPM to about 420 RPM, about 320 RPM to about 410 RPM, about 320 RPM to about 400 RPM, about 320 RPM to about 390 RPM, about 320 RPM to about 380 RPM, about 320 RPM to about 370 RPM, about 320 RPM to about 360 RPM, about 320 RPM to about 350 RPM, about 320 RPM to about 340 RPM, about 320 RPM to about 330 RPM, about 330 RPM to about 450 RPM, about 330 RPM to about 440 RPM, about 330 RPM to about 430 RPM, about 330 RPM to about 420 RPM, about 330 RPM to about 410 RPM, about 330 RPM to about 400 RPM, about 330 RPM to about 390 RPM, about 330 RPM to about 380 RPM, about 330 RPM to about 370 RPM, about 330 RPM to about 360 RPM, about 330 RPM to about 350 RPM, about 330 RPM to about 340 RPM, about 340 RPM to about 450 RPM, about 340 RPM to about 440 RPM, about 340 RPM to about 430 RPM, about 340 RPM to about 420 RPM, about 340 RPM to about 410 RPM, about 340 RPM to about 400 RPM, about 340 RPM to about 390 RPM, about 340 RPM to about 380 RPM, about 340 RPM to about 370 RPM, about 340 RPM to about 360 RPM, about 340 RPM to about 350 RPM, about 350 RPM to about 450 RPM, about 350 RPM to about 440 RPM, about 350 RPM to about 430 RPM, about 350 RPM to about 420 RPM, about 350 RPM to about 410 RPM, about 350 RPM to about 400 RPM, about 350 RPM to about 390 RPM, about 350 RPM to about 380 RPM, about 350 RPM to about 370 RPM, about 350 RPM to about 360 RPM, about 360 RPM to about 450 RPM, about 360 RPM to about 440 RPM, about 360 RPM to about 430 RPM, about 360 RPM to about 420 RPM, about 360 RPM to about 410 RPM, about 360 RPM to about 400 RPM, about 360 RPM to about 390 RPM, about 360 RPM to about 380 RPM, about 360 RPM to about 370 RPM, about 370 RPM to about 450 RPM, about 370 RPM to about 430 RPM, about 370 RPM to about 410 RPM, about 370 RPM to about 390 RPM, about 390 RPM to about 450 RPM, about 390 RPM to about 430 RPM, about 390 RPM to about 410 RPM, about 410 RPM to about 450 RPM, about 410 RPM to about 430 RPM, or about 430 RPM to about 450 RPM).

As is known in the art, a variety of cell culture parameters can be adjusted to achieve a specific dissolved $O_2$ concentration and a specific fluid sheer force. Non-limiting examples of such parameters that can be adjusted include: the well volume, the volume of the liquid culture medium, the shape of the well (e.g., one or more of the diameter, height, and shape of the well bottom), the type of agitation (e.g., rotary circular agitation and/or rotary ellipsoidal agitation), the frequency of agitation, the type of liquid culture medium, the interior coating of the well, and the temperature of the liquid culture medium. Additional examples of such culture parameters are known in the art. Any combination of culture parameters described herein or known in the art can be combined in any fashion to achieve in the culture medium a fluid sheer force and dissolved oxygen ($O_2$) concentration that is the same as (or essentially the same as) that achieved in a medium occupying about 10% to about 40% (e.g., about 15% to about 25%) of the volume of a square-bottom well having a diameter of between about 6.0 mm and about 35 mm and a height of between about 40 mm and about 50 mm, incubated at a temperature of about 31° C. to about 40° C., and agitated at a frequency of about 320 RPM to about 450 RPM (e.g., about 320 RPM to about 360 RPM).

Dissolved $O_2$ levels in a liquid culture medium can be detected using a variety of different methods. For example, dissolved $O_2$ can be measured using a dissolved $O_2$ electrode or probe (for example, the $O_2$ probes and electrodes available from Eutech Instruments WD-35201-80 Dissolved Oxygen Probe, Rosemount Analytical 499 Series Dissolved Oxygen/Ozone Sensor, and Extech DO705 Dissolved Oxygen Electrode). Methods of calibrating and using the $O_2$ probes and electrodes can be performed using the manufacturer's instructions.

The sheer fluid force in a liquid culture medium can be calculated using methods known in the art. A non-limiting example of a suitable textbook that describes the calculation of liquid sheer force in liquid culture medium is described in Fluid Mechanics, Robert A. Granger, 1995, Dover Publications, Inc., Mineola, N.Y., and Fundamentals of Fluid Mechanics, Bruce R. Munson et al., John Wiley & Sons, Inc., 2009.

Methods of Producing a Recombinant Protein

Also provided herein are methods of producing a recombinant protein, which include culturing a cell that is capable of producing the recombinant protein using a method described herein. Following performance of the method, the recombinant protein can be recovered from the mammalian cell and/or from the first or second culture medium. In some embodiments, the recombinant protein is recovered from the first and/or second liquid culture medium at any given time point during the culturing method (e.g., recovered from the first and/or second liquid culture medium on one or more of days 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 of culture, or after more than 100 days of culture). Some embodiments of these methods further include adding a volume of a third culture medium or a volume of a fourth liquid culture medium, but in each instance the total volume of liquid culture medium in the well should be about equal or less than the first liquid culture medium volume.

Skilled practitioners will appreciate that any of the various culture parameters (e.g., multi-well plates, wells, volumes, rates or frequencies of replacing culture volumes, agitation frequencies, temperatures, media, and $CO_2$ concentrations described herein) can be used in any combination in to perform these methods. Further, any of the mammalian cells described herein or known in the art can be used to produce a recombinant protein.

A nucleic acid encoding a recombinant protein can be introduced into a mammalian cell using a wide variety of methods known in molecular biology and molecular genetics. Non-limiting examples include transfection (e.g., lipofection), transduction (e.g., lentivirus, adenovirus, or retrovirus infection), and electroporation. In some instances, the nucleic acid that encodes a recombinant protein is not stably integrated into a chromosome of the mammalian cell (transient transfection); while in others the nucleic acid is integrated. Alternatively or in addition, the nucleic acid encoding a recombinant protein can be present in a plasmid and/or in a mammalian artificial chromosome (e.g., a human artificial chromosome). Alternatively or in addition, the nucleic acid can be introduced into the cell using a viral vector (e.g., a lentivirus, retrovirus, or adenovirus vector). The nucleic acid can be operably linked to a promoter sequence (e.g., a strong promoter, such as a β-actin promoter and CMV promoter, or an inducible promoter). A vector containing the nucleic acid can, if desired, also contain a selectable marker (e.g., a gene that confers hygromycin, puromycin, or neomycin resistance to the mammalian cell).

In some instances, the recombinant protein is a secreted protein and is released by the mammalian cell into the extracellular medium (e.g., the first and/or second liquid culture medium). For example, a nucleic acid sequence encoding a soluble recombinant protein can contain a sequence that encodes a secretion signal peptide at the N- or C-terminus of the recombinant protein, which is cleaved by an enzyme present in the mammalian cell, and subsequently released into the extracellular medium (e.g., the first and/or second liquid culture medium). For example, such a secreted recombinant protein can be a secreted immunoglobulin, a secreted enzyme, a secreted growth factor, a secreted protein fragment, or a secreted engineered protein. In other instances, the recombinant protein is a soluble protein that is not secreted, and the recombinant protein is recovered from within the mammalian cell. For example, a recombinant protein that is not secreted can be an immunoglobulin, an enzyme, a growth factor, a protein fragment, or an engineered protein.

Non-limiting examples of recombinant proteins that can be produced by the methods provided herein include immunoglobulins (including light and heavy chain immunoglobulins, antibodies, or antibody fragments (e.g., any of the antibody fragments described herein), enzymes (e.g., a galactosidase (e.g., an alpha-galactosidase), Myozyme, or Cerezyme), proteins (e.g., a growth factor, human erythropoietin, tumor necrosis factor (TNF), or an interferon alpha or beta), an engineered protein, or immunogenic or antigenic proteins or protein fragments (e.g., proteins for use in a vaccine). In some embodiments, the recombinant protein is an engineered antigen-binding polypeptide that contains at least one multifunctional recombinant protein scaffold (see, e.g., the recombinant antigen-binding proteins described in Gebauer et al., *Current Opin. Chem. Biol.* 13:245-255, 2009; and U.S. Patent Application Publication No. 2012/0164066 (herein incorporated by reference in its entirety)). Non-limiting examples of recombinant proteins that are antibodies include: panitumumab, omalizumab, abagovomab, abciximab, actoxumab, adalimumab, adecatumumab, afelimomab, afutuzumab, alacizumab, alacizumab, alemtuzumab, alirocumab, altumomab, amatuximab, anatumomab, apolizumab, atinumab, tocilizumab, basilizimab, bectumomab, belimumab, bevacizumab, biciromab, canakinumab, cetuximab, daclizumab, densumab, eculizumab, edrecolomab, efalizumab, efungumab, ertumaxomab, etaracizumab, golimumab, infliximab, natalizumab, palivizumab, panitumumab, pertuzumab, ranibizumab, rituximab, tocilizumab, and trastuzumab. Additional examples of therapeutic antibodies that can be produced by the methods described herein are known in the art. Additional non-limiting examples of recombinant proteins that can be produced by the present methods include: alglucosidase alfa, laronidase, abatacept, galsulfase, lutropin alfa, antihemophilic factor, agalsidase beta, interferon beta-1a, darbepoetin alfa, tenecteplase, etanercept, coagulation factor IX, follicle stimulating hormone, interferon beta-1a, imiglucerase, dornase alfa, epoetin alfa, and alteplase.

A secreted, soluble recombinant protein can be recovered from the liquid culture medium (e.g., the first and/or second liquid culture medium) by removing or otherwise physically separating the liquid culture medium from the mammalian cells. A variety of different methods for removing liquid culture medium from mammalian cells are known in the art, including, for example, centrifugation, filtration, pipetting, and/or aspiration. The secreted recombinant protein can then be recovered and further purified from the liquid culture medium using a variety of biochemical techniques including various types of chromatography (e.g., affinity chromatography, molecular sieve chromatography, cation exchange chromatography, or anion exchange chromatography) and/or filtration (e.g., molecular weight cut-off filtration).

To recover an intracellular recombinant protein, the mammalian cell can be lysed. A wide variety of methods for lysing mammalian cells are known in the art, including, for example, sonication and/or detergent, enzymatic, and/or chemical lysis. A recombinant protein can be purified from a mammalian cell lysate using a variety of biochemical methods known in the art, typically starting with a step of centrifugation to remove the cellular debris, and then one or more additional steps (e.g., one or more types of chromatography (e.g., affinity chromatography, molecular sieve chromatography, cation exchange chromatography, or anion exchange chromatography) and/or filtration (e.g., molecular weight cut-off filtration)).

In some embodiments, the recovered recombinant protein is at least or about 50% pure by weight, e.g., at least or about 55% pure by weight, at least 60% pure by weight, at least 65% pure by weight, at least 70% pure by weight, at least 75% pure by weight, at least 80% pure by weight, at least 85% pure by weight, at least 90% pure by weight, at least 95% pure by weight, at least 96% pure by weight, at least 97% pure by weight, at least 98% pure by weight, or at least or about 99% pure by weight, or greater than 99% pure by weight.

EXAMPLES

The invention is further described in the following examples, which do not limit the scope of the invention described in the claims.

Example 1

Beneficial Properties of an Exemplary Culturing Method

Experiments were performed to generate a small-scale high throughput model of perfusion cultures and to determine whether such cultures can achieve cell densities similar to that of production perfusion cultures.

Materials and Methods

Recombinant Galactosidase Suspension Cell Culture

The same clonal cell line that produced recombinant galactosidase was used in each cell culture process run, and the culture medium used in each cell culture process run is listed in Table 1.

TABLE 1

Culture Media used in the Studies.

| Cell Culture Process Run | Medium (Lot No.) |
| --- | --- |
| I | CD-CHO (021113M) |
| II | CD-CHO (021113M) |
| III | CD-CHO (041013M) |
| IV | CD-CHO (041013M) |
| V | CD-CHO (041013M) |

Equipment and Reagents

The following equipment and reagents were used in the cell culture process runs described in this Example: Multitron shaker incubator (Appropriate Technical Resources, Inc.) (Model No. AJ125), Cellometer® Auto1000 (Nexcelom Bioscience LLC), Beckman Coulter Allegra centrifuge (Model No. Allegra X-14 R), TubeSpin® Bioreactors 50 (Techno Plastic Products AG, Trasadingen, Switzerland), 96-Well MASTERBLOCK® microplates 2-mL (Griener Bio One, Frickenhausen, Germany), 96-Well MASTERBLOCK® microplates 1-mL (Griener Bio One, Frickenhausen, Germany), Olympus white light bench top microscope (Model No. BH-s), Olympus white light bench top microscope (Model No. BX40), Olympus white light bench top microscope (Model No. BX41), 0.4% Trypan Blue solution (Sigma), 0.2% Trypan Blue solution (Sigma), Reichert Bright-Line® hemacytometer chamber, Thermo Scientific microscope cover glass, Fisher Scientific Laboratory Counter, SAS® JMP Software (version X), Applikon MicroFlask microtiter plate clamping device (Applikon Biotechnology Inc.), AeraSeal, microporous disposable membrane seals (Phenix Research Products), Beckman Coulter Biomek® 3000 Laboratory Automation Workstation, RAININ Pipetting 360° Pipet-Lite™ XLS™ Pipettor (Mettler Toledo), Ergenomic High-Performance Pipettor (VWR®), and Reagent Reservoir (VistaLab Technologies).

Methods

Studies were performed to test a range of varying conditions for agitation (RPM), well shape, and working volume.

The studies were designed to cover the ranges of agitation of between 320 RPM to 360 RPM, round-bottom (1-mL nominal volume) or square-bottom (2-mL nominal volume) wells, and between 100 μL to 600 μL working volume. Cell Culture Process Run I was performed to determine a basis for operating conditions for round-bottom deep-well plates (1-mL nominal volume). Cell Culture Process Run II was performed to determine the round-bottom deep-well plates' ability to support high density cell cultures. Cell Culture Process Run III was performed to establish parameter ranges for design optimization, as well as compare the Applikon MicroFlask microtiter plate clamping device (Applikon Biotechnology, Inc., Foster City, Calif.) to the sterile, microporous membrane seals (AeraSeal, Phenix Research Products, Candler N.C.). Cell Culture Process Runs IV and V were designed for model optimization purposes.

Cell Culture Process Run V was designed using JMP software's custom design tool. The model was designed as an I-optimal with two continuous variables (shaking speed and working volume) and one categorical response (well shape) taking into account third-order interactions. The lower and upper limits were set according to Table 2 (with the working volumes listed as a fraction of the total vessel volume). The design was customized to have a power of 2 to account for any non-linear relations between variables. Lastly, the study was designed to have a total of 15 conditions per experiment (six for round- and nine for square-bottom wells) ran in duplicate.

TABLE 2

Continuous Variable Settings Used in JMP.

| Variable | Lower Limit | Upper Limit |
|---|---|---|
| Shaking Speed (RPM) | 320 | 360 |
| Working Volume | 0.1 | 0.3 |
| Working Volume (mL) | 2 | 30 |

All vessels were inoculated at $5 \times 10^6$ viable cells/mL using cells from seed cultures expanded in shake flasks for 9, 10, 7, 0, and 7 passages for Cell Culture Process Runs 1-5, respectively, following vial thaw of cell banks. Cell cultures were maintained in a controlled environment of 5% $CO_2$, 37° C., and 80% relative humidity in a shaking incubator. A control shake tube condition was run with each experiment with a constant working volume of 10 mL per tube, with a shaking angle of 45° and an agitation of 160 RPM. For all experiments (unless noted otherwise), evaporation was accounted for according to Table 3.

TABLE 3

Evaporation Supplementation

| Variable | Round DWP | Square DWP |
|---|---|---|
| Applikon | 20 μL | 20 μL |
| Disposable Membrane | 20 μL | 40 μL |

For Cell Culture Process Run I, a round-bottom deep well plate was inoculated at $5 \times 10^5$ viable cells/mL and $1 \times 10^6$ viable cells/mL. Starting on day 1 after the inoculation, the cultures were sampled daily (10 μL) to determine the viable cell density (VCD) by manual count (trypan blue exclusion) for 2 days.

For Cell Culture Process Run II, starting on day one after the inoculation, the cultures were sampled daily (10 μL) to determine the VCD by manual count for 11 days. Following the cell count, the plates were centrifuged at −233×g for 5 minutes, and the spent media removed. The culture medium was exchanged at ratios described in Table 4.

Round-bottom (1-mL) deep-well plates and square-bottom (2-mL) deep-well plates were used for Cell Culture Process Runs III and IV. Beginning on day one post-inoculation, the cultures were sampled on every Monday, Wednesday, and Friday (2-2-3 schedule) (10 μL) to determine the VCD through Cellometer® Auto 1000. Following the cell count, the plates were centrifuged at −233×g for 5 minutes, and the spent media removed. The culture medium was exchanged at ratios described in Table 4.

For Cell Culture Process Run V, the Biomek 3000 liquid handler was used. Beginning on day one post-inoculation, the cultures were sampled every Monday, Wednesday, and Friday (0.10× working volume) to determine the VCD through Cellometer® Auto 1000. Following the cell counting, the plates were centrifuged at 233×g for 5 minutes, and the removed spent media were used immediately or stored at −80° C. until recombinant human α-galactosidase (rha-Gal) activity assays were performed to determine product titer. The culture medium was exchanged at ratios described in Table 5, and the rha-Gal volumetric and specific productivity rates were calculated using Equations 1 and 2 below. Additionally, integrated viable cell densities (IVCDs) were calculated using Equation 3 below.

TABLE 4

Batch Refeed Schedule

| Day of Culture after Seeding[1] | Refeed Rate (reactor volume per day) |
|---|---|
| Days 1-3 | 0.5 RV/d |
| Days 4-6 | 0.7 RV/d |
| Day 7 onwards | 1.0 RV/d |

[1]Seeding density at inoculation is $5 \times 10^5$ cells/mL.

TABLE 5

Modified Batch Refeed Schedule

| Day of Culture after Seeding[1] | Refeed Rate (reactor volume per day) |
|---|---|
| Days 1-3 | 0.4 RV/d |
| Days 4-6 | 0.5 RV/d |
| Days 7-10 | 0.7 RV/d |
| Day 11 onward | 2 × 0.5 RV/d |

[1]Seeding density at inoculation is $5 \times 10^5$ cells/mL.

$$VPR = Titer * PR \quad \text{Equation 1}$$

$$SPR = \frac{VPR}{Xv} \quad \text{Equation 2}$$

$$IVCD_n = IVCD_{n-1} + \left(\left(\frac{Xv_n + Xv_{n-1}}{2}\right) * (t_n - t_{n-1})\right) \quad \text{Equation 3}$$

PR: Perfusion rate
VPR: Volumetric productivity rate (U/L/d)
Titer: rh α-Gal activity (U/L)
SPR: Specific productivity rate (U/E9 cells/d)
Xv: Viable cell count (E6 cells/mL)
IVCD: Integrated viable cell density (cells-d/mL)
t: Time (d)

Manual Cell Counting

The hemocytometer chamber and cover-slip were cleaned with isopropyl alcohol (IPA). The corner of the cover-slips were wetted with IPA and affixed to the hemocytometer. The cell samples were homogenously mixed with 1:1 with 0.4% trypan blue. An aliquot of 10 µL was transferred to a hemocytometer chamber. The cells were counted in the four larger outer squares: each large outer square contained a grid of 16 smaller squares. Cells lying on the boundaries of the larger square were counted only on two of the four sides. Uncolored cells were counted as viable, while those stained in blue were considered dead. Percent viability and viable cell density were calculated using Equations 4 and 5 below.

$$\text{Viability} = \left(\frac{\text{Viable Cells}}{\text{Total Cells}}\right) \cdot 100\% \quad \text{Equation 4}$$

$$\text{Viable Cell Density} = \left(\frac{\text{Viable Cells}}{\text{Squares Counted}}\right) \cdot \text{Dilution Factor} \cdot 10^4 \quad \text{Equation 5}$$

Total Cells: Sum of Viable Cells and Dead Cells

Nexcelom Cellometer Cell Counting

The cell samples were homogenously mixed 1:1 with 0.2% trypan blue. An aliquot of 20 µL of the mixture was transferred to instrument-specific slides. Cells were counted in the four images taken by a digital camera incorporated in the instrument. Uncolored cells were counted as viable, while those stained blue were considered dead.

Statistical Analysis

Statistical analysis was performed using JMP software. The responses used were peak viable cell density (VCD or Xv) and volumetric productivity rate (VPR) with maximized desirability. The statistical model was assessed through the 'Fit Model' function with an effect screening report. The 'Sorted Parameter Estimates' reported the factors that significantly effected response variables, which is statistically determined through a t-test. Lastly, the 'Prediction Profiler' plots the independent trends of the effects of the parameters on response variables and uses the model to predict the best conditions through maximizing the desirability function.

Results

Cell Culture Process Run I

In this experiment, on day 27 after vial thaw, a rha-Gal CHO cell line (in the CD CHO medium) was used to inoculate vessels under three different conditions (Table 6). The cell culture proliferation profile was followed over 11 days.

TABLE 6

Cell Culture Process I Tested Conditions

| Vessel-type | Total Volume | Working Volume | Shaking Speed |
|---|---|---|---|
| Shake Tube | 50 mL | 10 mL | 160 RPM |
| 96 DWP (Round) | 1 mL | 200 µL | 330 RPM |
| 96 DWP (Round) | 1 mL | 300 µL | 330 RPM |

Figure 5:
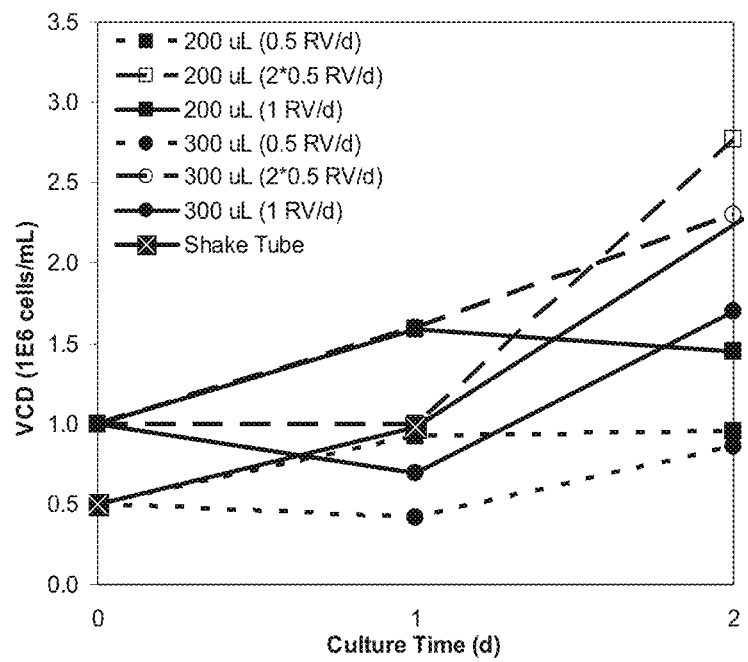
FIG. 5 is a graph of the viable cell density over two days of cells perfusion cultured in a 50-mL shake tube containing 10-mL culture medium and agitated at 160 RPM or a round-bottom 96-deep-well plate containing 200 µL or 300 µL of culture medium and agitated at 330 RPM, and cultured during different batch re-feed rates. The error bars represent a standard deviation of n=2.
Figure 6:
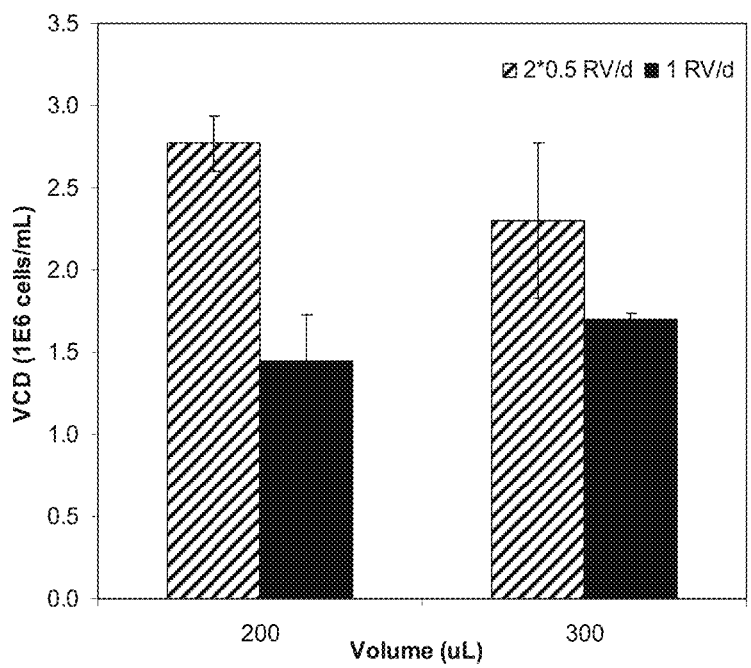
FIG. 6 is a graph of the end-point viable cell density of a two-day culture of cells perfusion cultured in a round-bottom 96-deep-well plate containing 200 µL or 300 µL of culture medium and agitated at 330 RPM, and cultured at different batch re-feed rates (2×0.5 reactor volume/day or 1 reactor volume/day). The error bars represent a standard deviation of n=2.

The viable cell density profiles of the cultures maintained in CD CHO medium for eleven days are shown in FIG. 5. Growth was observed in all the experimental cultures. For the cells seeded at $5 \times 10^5$ cells/mL, there was minimal growth in both working volumes (200 µL and 300 µL) reaching a VCD of $1 \times 10^6$ cells/mL. This suggests that the cells are capable of growth at low seeding densities in the round-bottom deep-well plates. The cultures seeded at $1 \times 10^6$ cells/mL also exhibited growth by day 2, with the cultures being re-fed twice a day at 0.5 RV having better growth (FIG. 6). The cultures re-fed twice a day reached a VCD above $2 \times 10^6$ cells/mL at day 2: $2.7 \times 10^6$ cells/mL at 200 µL and $2.3 \times 10^6$ cells/mL at 300 µL. The cultures re-fed at approximately 1.0 RV/day had much lower VCD at day 2, which could have also resulted from unintentional cell loss during spent media removal. These data indicate that a perfusion rate of 2×0.5 RV/day allows for better cell growth than a perfusion rate of 1.0 RV/day. These data suggest that round-bottom 1-mL 96-deep-well plates are capable of supporting cell growth. Throughout the experiment, the cultures were observed to have small cell pellets when immediately removed from the shaking incubator, possibly due to insufficient agitation. This observation suggests that a higher agitation speed should be used for the round-bottom 1-mL deep-well plates.

Cell Culture Process Run II

A set of experiments was performed to optimize the perfusion rate used to culture cells in round-bottom (1-mL) 96-deep-well plates. In these experiments, rha-Gal cells (on day 30 after vial thaw) in CD CHO medium were used to inoculate wells of round-bottom 96-deep-well plates and shake tubes (as described in Table 7). Cell culture performance was evaluated in an 11-day batch re-feed process.

TABLE 7

Cell Culture Process Run Tested Conditions

| Vessel-type | Total Volume | Working Volume | Shaking Speed |
|---|---|---|---|
| Shake Tube | 50 mL | 10 mL | 160 RPM |
| 96 DWP (Round) | 1 mL | 300 µL | 360 RPM |

Figure 7:
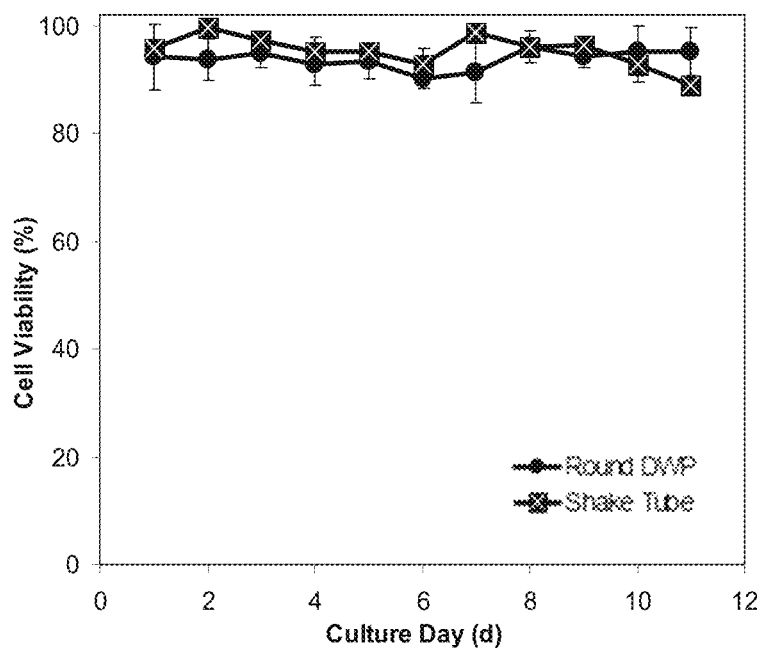
FIG. 7 is a graph of the percentage cell viability of an 11-day culture of cells perfusion cultured in a round-bottom 96-deep-well plate containing 300 µL of culture medium and agitated at 360 RPM or in a shake tube containing 10 mL culture medium and agitated at 160 RPM. The error bars represent a standard deviation of n=2 for the shake tube cultures and n=8 for the round-bottom 96-deep-well plate cultures.
Figure 8:
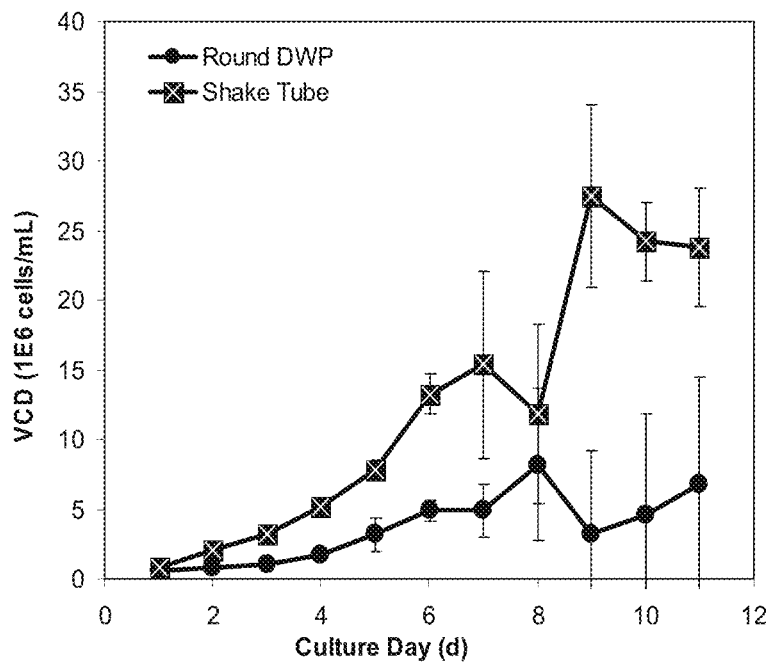
FIG. 8 is the viable cell density of cultures of an 11-day culture of cells perfusion cultured in a round-bottom 96-deep-well plate containing 300 µL of culture medium and agitated at 360 RPM or in a shake tube containing 10 mL culture medium and agitated at 160 RPM. The error bars represent a standard deviation of n=2 for the shake tube cultures and n=8 for the round-bottom 96-deep-well cultures.

All cultures maintained a percentage cell viability of above 85% (FIG. 7). The viable cell density profiles of the 11-day cultures of the cells maintained in CD CHO medium are shown in FIG. 8. Growth was observed for all cultures up to day 9 when the experimental control (the shake tube culture) cell growth plateaued at a peak density of $25 \times 10^6$ cells/mL. The culture in the round-bottom 96-deep well plates exhibited a slower growth rate than the experimental control, reaching a peak VCD at $8 \times 10^6$ cells/mL. At day 8, a bolus (50 µL) of media was added to the round-bottom 96-deep-well plate cultures accounting for evaporation loss.

Figure 9:
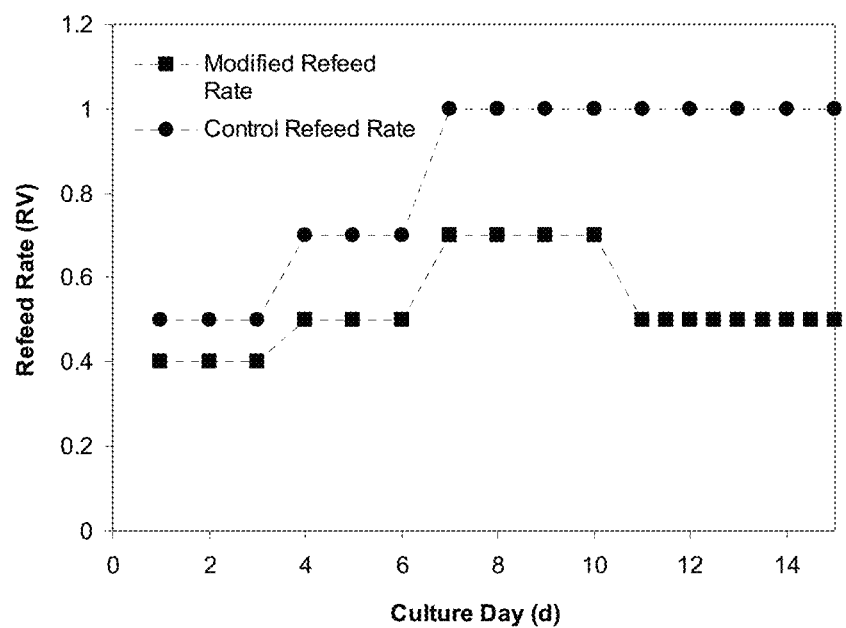
FIG. 9 is a graph of the reefed rate (in reactor volume(s)) used on each day of a 15-day culture in the modified refeed rate protocol and the control refeed rate protocol.

These data for the round-bottom 96-deep-well plate suggest that the refeed schedule should be adjusted. A modified refeed schedule is shown in FIG. 9 and Table 3.

Cell Culture Process Run III

A set of experiments was performed to optimize the refeed rate used to culture cells in round-bottom 96-deep-well plates. These experiments were performed using both 1-mL round-bottom and 2-mL square-bottom 96-deep-well plates and the modified refeed rate protocol shown in FIG. 9. On day 8 after vial thaw, the rha-Gal cells in CD CHO culture media were used to inoculate both types of deep-well plates and shake tubes (see, Table 8). The square-bottom 96-deep-well cultures contained a culture volume of 300 µL or 500 µL, while the round-bottom 96-deep-well cultures contained a culture volume of 200 µL or 300 µL (1 mL nominal volume). The wells were either sealed using the Applikon system or using AeraSeal membranes. All of the 96-deep-well plate cultures were agitated at either 330 RPM or 360 RPM. The cell culture growth was measured over 9 days. All the viable cell counts for the 96-deep-well plate cultures were counted in triplicate wells and averaged.

Figure 10:
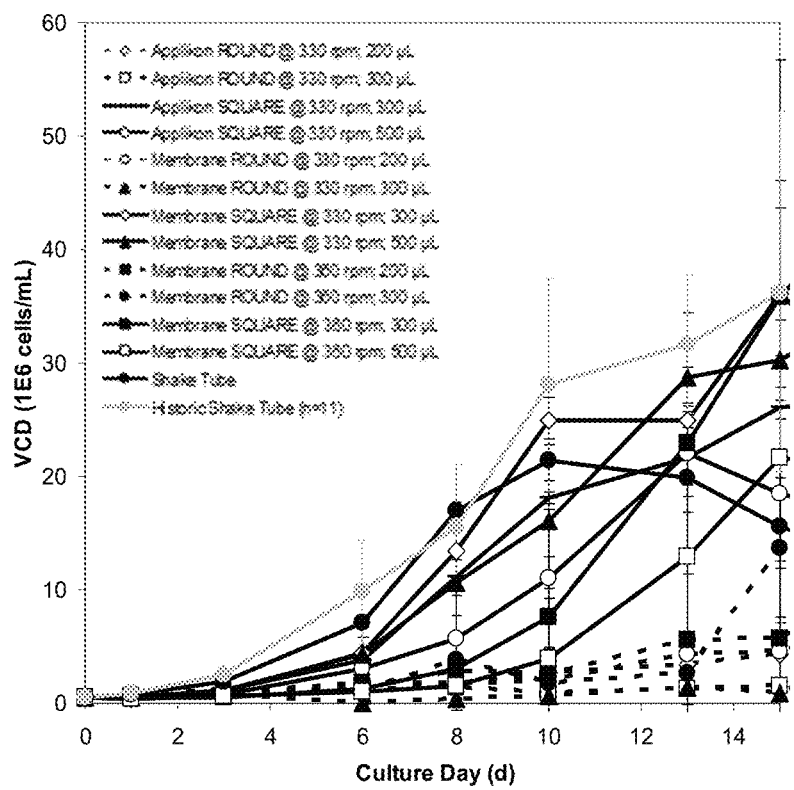
FIG. 10 is graph of the viable cell density over time of cells cultured in square-bottom or round-bottom 96-deep-well plates containing either 200 µL, 300 µL, or 500 µL culture medium, agitated at 330 RPM or 360 RPM, and sealed using the Applikon system or a disposable membrane; or cultured in control shake tubes. The error bars represent the standard deviation of n=3.

The viable cell density profiles of the 15-day cell cultures are shown in FIG. 10. Similar growth profiles were exhibited for the square-bottom 96-deep-well plate cultures covered using the Applikon system or covered using the disposable membrane seals (lying within one standard deviation (1 SD) of each other). The highest viable cell density in the 96-well plate format was a viable cell density of $35 \times 10^6$ cells/mL, which was achieved in the square-bottom 96-deep-well plates at day 15. The highest viable cell density achieved in the control shake tube cultures was $21 \times 10^6$ cells/mL at day 10. The square-bottom 96-deep-well plate cultures also closely resembled the growth profile of the control shake tube cultures until day 13. However, the square-bottom 96-deep-well plate cultures resembled the historic shake tube control (n=11) for the entire 15-day process. The two square-bottom 96-deep-well plate cultures that most closely resembled the historic shake tube control cultures used disposable membrane covers and were agitated at 330 RPM and had a culture volume of 300 µL or 500 µL.

Figure 11:
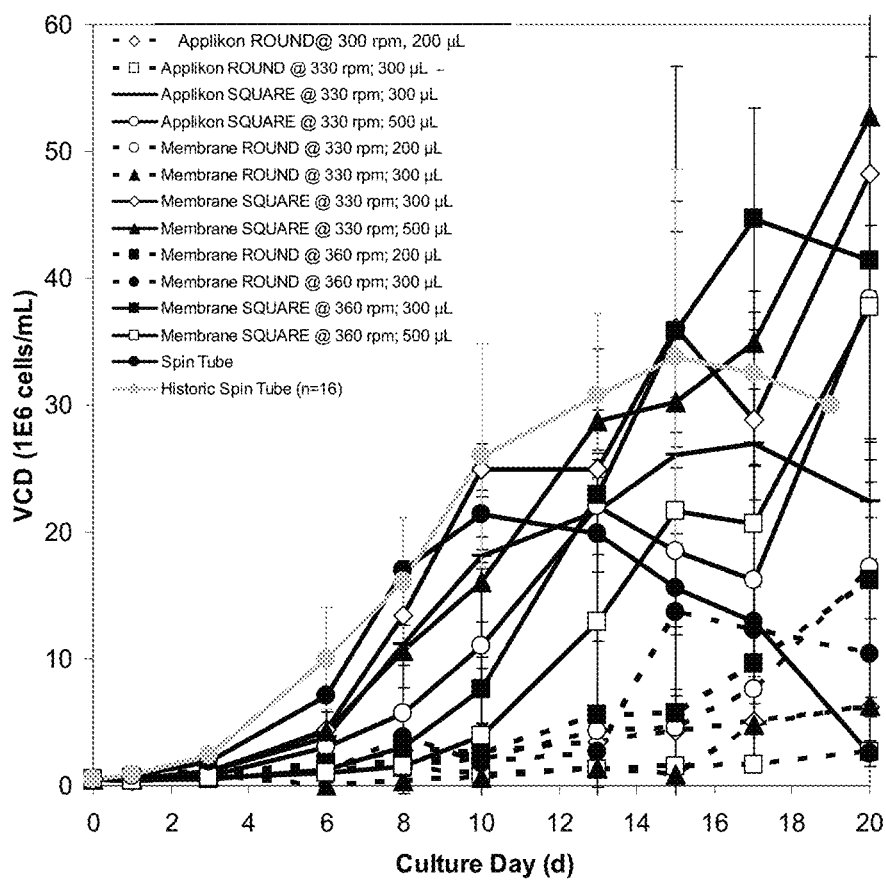
FIG. 11 is a graph of the percentage of viable cells over time of cells cultured in square-bottom or round-bottom 96-deep-well plates containing either 200 µL, 300 µL, or 500 µL culture medium, agitated at 330 RPM or 360 RPM, and sealed using the Applikon system or a disposable membrane; or cultured in control shake tubes. The error bars represent the standard deviation of n=3.
Figure 12:
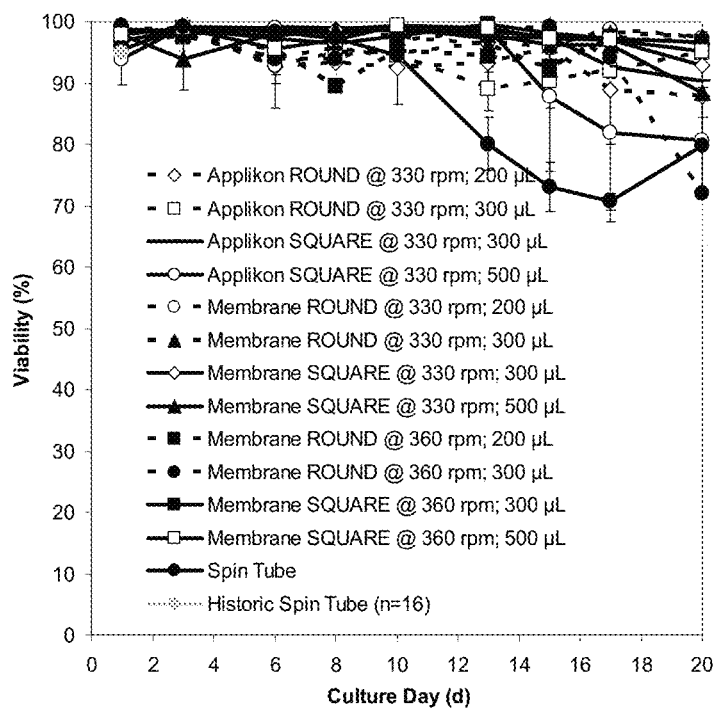
FIG. 12 is graph of the viable cell density over time of cells cultured in square-bottom or round-bottom 96-deep-well plates containing either 200 µL, 300 µL, or 500 µL culture medium, agitated at 330 RPM or 360 RPM, and sealed using the Applikon system or a disposable membrane; or cultured in control shake tubes. The error bars represent the standard deviation of n=3.
Figure 13:
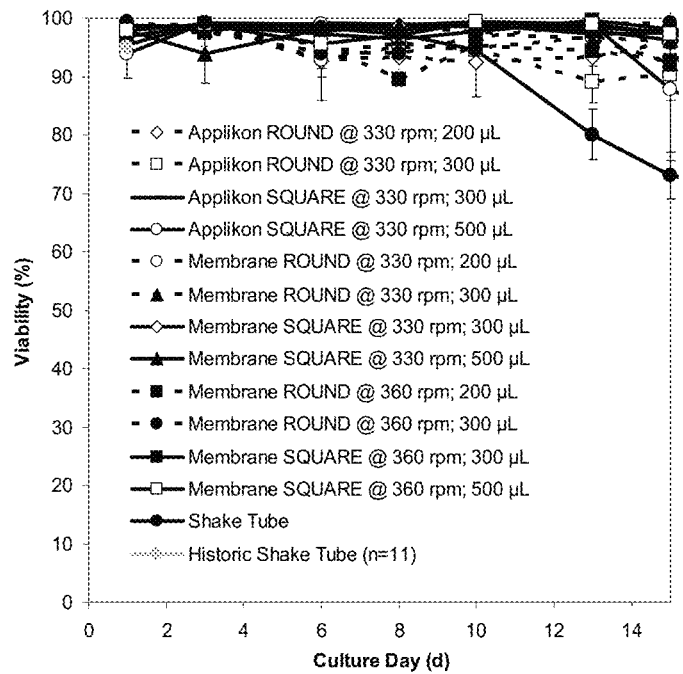
FIG. 13 is a graph of the percentage of viable cells over time of cells cultured in square-bottom or round-bottom 96-deep-well plates containing either 200 µL, 300 µL, or 500 µL culture medium, agitated at 330 RPM or 360 RPM, and sealed using the Applikon system or a disposable membrane; or cultured in control shake tubes. The error bars represent the standard deviation of n=3.

The round-bottom 96-deep-well plate cultures in this experiment did not exhibit comparable growth to the control shake tube cultures. The highest viable cell density observed in the round-bottom 96-deep-well plate cultures was $14 \times 10^6$ cells/mL at day 15. All cultures maintained a percentage cell viability above 85% (FIG. 11), until entering the decline phase. Unlike the shake tube control, cultures in both well shapes continued to proliferate beyond day 14, reaching viable cell densities of $50 \times 10^6$ cells/mL (square-bottom) and $17 \times 10^6$ cells/mL by day 20 (round-bottom) (FIGS. 12 and 13). These data indicate that the round-bottom 96-deep well plates are capable of supporting high cell densities.

TABLE 8

Cell Culture Process Run III Tested Conditions

| Vessel-type | Total Volume | Working Volume | Shaking Speed | Sterile Cover |
|---|---|---|---|---|
| Shake Tube | 50 mL | 10 mL | 160 RPM | Vented cap |
| 96 DWP (Round) | 1 mL | 200 µL | 330 RPM | Applikon |
| 96 DWP (Round) | 1 mL | 300 µL | 330 RPM | Applikon |
| 96 DWP (Round) | 1 mL | 200 µL | 330 RPM | Disposable Membrane |
| 96 DWP (Round) | 1 mL | 300 µL | 330 RPM | Disposable Membrane |
| 96 DWP (Round) | 1 mL | 200 µL | 360 RPM | Disposable Membrane |
| 96 DWP (Round) | 1 mL | 300 µL | 360 RPM | Disposable Membrane |
| 96 DWP (Square) | 2 mL | 300 µL | 330 RPM | Disposable Membrane |
| 96 DWP (Square) | 2 mL | 500 µL | 330 RPM | Disposable Membrane |
| 96 DWP (Square) | 2 mL | 300 µL | 330 RPM | Disposable Membrane |
| 96 DWP (Square) | 2 mL | 500 µL | 330 RPM | Disposable Membrane |
| 96 DWP (Square) | 2 mL | 300 µL | 360 RPM | Disposable Membrane |
| 96 DWP (Square) | 2 mL | 500 µL | 360 RPM | Disposable Membrane |

Cell Culture Process Run IV

An additional set of experiments was performed to optimize cell growth in square-bottom 96-deep-well plates (2-mL nominal volume). In these experiments, on day 1 after vial thaw, the cells in CD CHO culture medium was used to inoculate square-bottom 96-deep-well plates and shake tubes (n=3) (see, Table 9). The culture volume used in these experiments was 300 µL or 500 µL, and the cultures were agitated at 320 RPM, 330 RPM, or 340 RPM. Cell growth in the cultures was evaluated over 14 days. All of the viable cell counts for the cultures were counted from triplicate wells and averaged.

TABLE 9

Cell Culture Process Run IV Tested Conditions

| Vessel-type | Total Volume | Working Volume | Shaking Speed | Sterile Cover |
|---|---|---|---|---|
| Shake Tube | 50 mL | 10 mL | 160 RPM | Vented cap |
| 96 DWP (Square) | 2 mL | 300 µL | 320 RPM | Disposable Membrane |
| 96 DWP (Square) | 2 mL | 500 µL | 320 RPM | Disposable Membrane |
| 96 DWP (Square) | 2 mL | 300 µL | 330 RPM | Disposable Membrane |
| 96 DWP (Square) | 2 mL | 500 µL | 330 RPM | Disposable Membrane |
| 96 DWP (Square) | 2 mL | 300 µL | 340 RPM | Disposable Membrane |
| 96 DWP (Square) | 2 mL | 500 µL | 340 RPM | Disposable Membrane |

Figure 14:
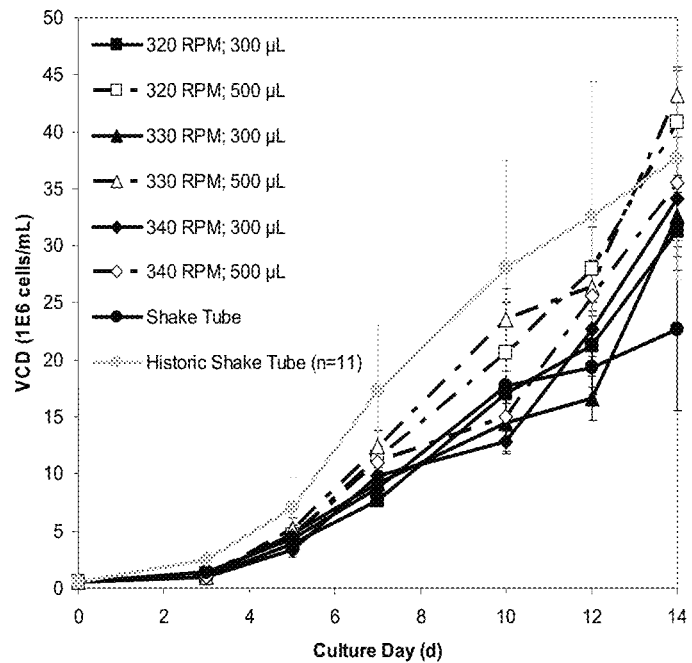
FIG. 14 is a graph of the viable cell density over time of cells cultured in square-bottom 96-deep-well plates containing either 300 µL or 500 µL culture medium and agitated at 320 RPM, 330 RPM, or 340 RPM; or cultured in control shake tubes. The error bars represent a standard deviation of n=3.

The viable cell density profiles of the square-bottom 96-deep-well plate cultures over 14 days is shown in FIG. 14. Similar growth profiles were exhibited for all tested conditions until day 7. After day 7, the square-bottom 96-deep-well plate cultures having a culture volume of 500 µL and agitated at 320 RPM or 330 RPM demonstrated better cell growth. Although all tested culture conditions continued to proliferate past day 13, reaching a viable cell density of $30 \times 10^6$ cells/mL to $35 \times 10^6$ cells/mL, the two culture conditions with better growth performance reached viable cell densities above $40 \times 10^6$ cells/mL. The viable cell densities achieved in the square-bottom 96-deep-well plate cultures having a culture volume of 500 µL and an agitation rate of 320 RPM or 330 RPM surpassed the viable cell densities observed historically in cultures of the same cell line in shake tubes (falling within 1 standard deviation) after day 12. Up to day 12 of the cultures, similar growth patterns were observed in the square-bottom 96-deep-well plate cultures having a culture volume of 500 µL and an agitation rate of 320 RPM or 330 RPM and the shake tube cultures.

Cell Culture Process Run V

A further set of experiments were performed to optimize the cell culture operating conditions (see, description of Design of Experiment methods above). In these experiments, on day 21 after vial thaw, cells in CD CHO were used to inoculate either square-bottom or round-bottom 96-deep-well plates, or shake tubes. The operating conditions for each tested culture are shown in Table 10. Each of the tested 96-deep-well plates were covered with AeraSeal disposable membranes. The shake tube cultures served as the control (n=4): one set of two shake tube cultures followed the control refeed schedule, and another set of two shake tube cultures followed the modified refeed rate used in the 96-deep-well plates (depicted in FIG. 9). All conditions were tested in duplicate. Cell growth was evaluated in a 9-day batch refeed process.

TABLE 10

Cell Culture Process Run V Tested Conditions

| Vessel-type | Total Volume | Working Volume | Shaking Speed | Sterile Cover |
|---|---|---|---|---|
| Shake Tube | 50 mL | 10 mL | 160 RPM | Vented cap |
| 96 DWP (Round) | 1 mL | 100 µL | 320 RPM | Disposable Membrane |
| 96 DWP (Round) | 1 mL | 300 µL | 320 RPM | Disposable Membrane |
| 96 DWP (Round) | 1 mL | 200 µL | 340 RPM | Disposable Membrane |
| 96 DWP (Round) | 1 mL | 100 µL | 360 RPM | Disposable Membrane |
| 96 DWP (Round) | 1 mL | 300 µL | 360 RPM | Disposable Membrane |
| 96 DWP (Square) | 2 mL | 200 µL | 320 RPM | Disposable Membrane |
| 96 DWP (Square) | 2 mL | 400 µL | 320 RPM | Disposable Membrane |
| 96 DWP (Square) | 2 mL | 600 µL | 320 RPM | Disposable Membrane |
| 96 DWP (Square) | 2 mL | 200 µL | 340 RPM | Disposable Membrane |
| 96 DWP (Square) | 2 mL | 400 µL | 340 RPM | Disposable Membrane |
| 96 DWP (Square) | 2 mL | 600 µL | 340 RPM | Disposable Membrane |
| 96 DWP (Square) | 2 mL | 200 µL | 360 RPM | Disposable Membrane |
| 96 DWP (Square) | 2 mL | 400 µL | 360 RPM | Disposable Membrane |
| 96 DWP (Square) | 2 mL | 600 µL | 360 RPM | Disposable Membrane |

Figure 15:
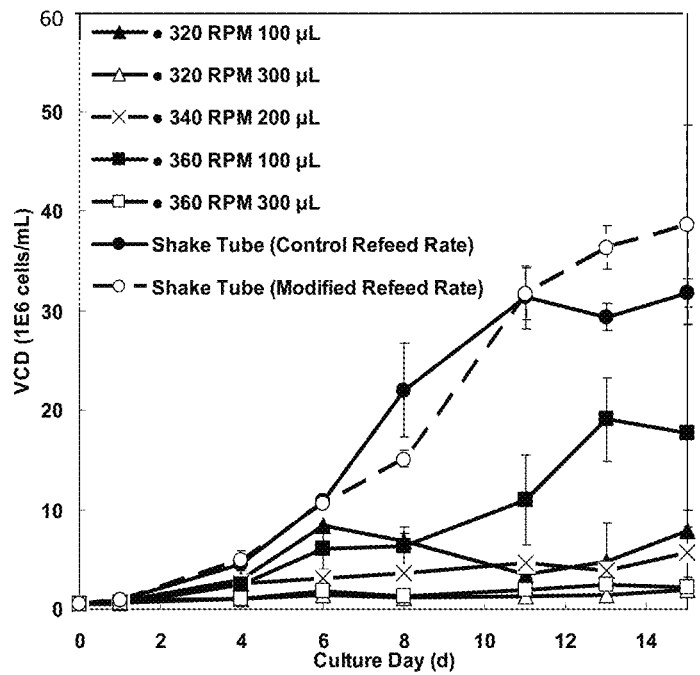
FIG. 15 is a graph of the viable cell density over time of cells cultured in round-bottom 96-deep-well plates containing either 100 µL, 200 µL, or 300 µL CD CHO culture medium and agitated at 320 RPM, 340 RPM, or 360 RPM, or cells cultured in a shake tube (with media perfusion performed using the control refeed rate or the modified refeed rate). The error bars represent a standard deviation of n=2.
Figure 16:
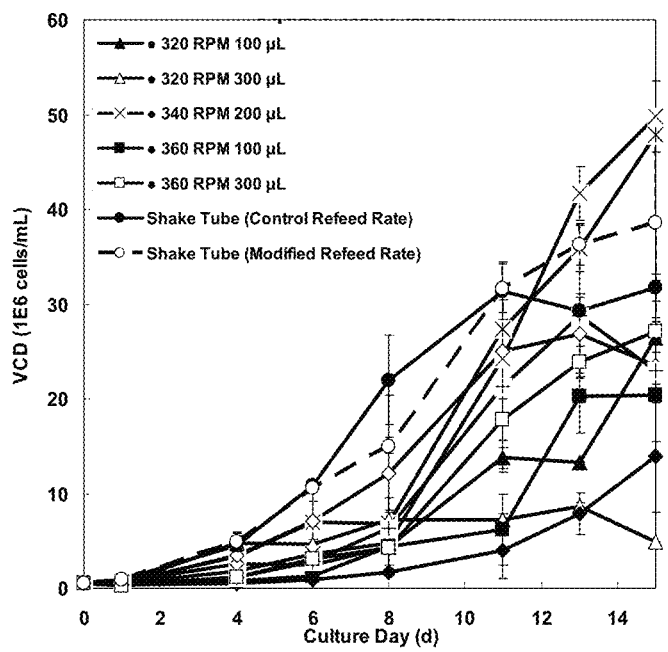
FIG. 16 is a graph of the viable cell density over time of cells cultured in square-bottom 96-deep-well plates containing either 200 µL, 400 µL, or 600 µL CD CHO culture medium and agitated at 320 RPM, 340 RPM, or 360 RPM, or cells cultured in a shake tube (with media perfusion performed using the control refeed rate or the modified refeed rate). The error bars represent a standard deviation of n=2.
Figure 17:
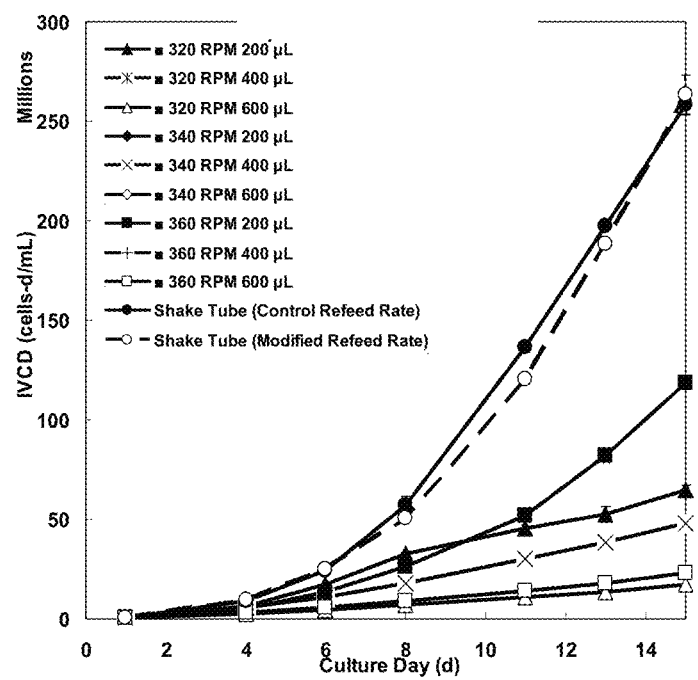
FIG. 17 is a graph of the integrated viable cell density of cells cultured in round-bottom 96-deep-well plates containing either 100 µL, 200 µL, or 300 µL CD CHO culture medium and agitated at 320 RPM, 340 RPM, or 360 RPM, or cells cultured in a shake tube (with media perfusion performed using the control refeed rate or the modified refeed rate). The error bars represent a standard deviation of n=2.
Figure 18:
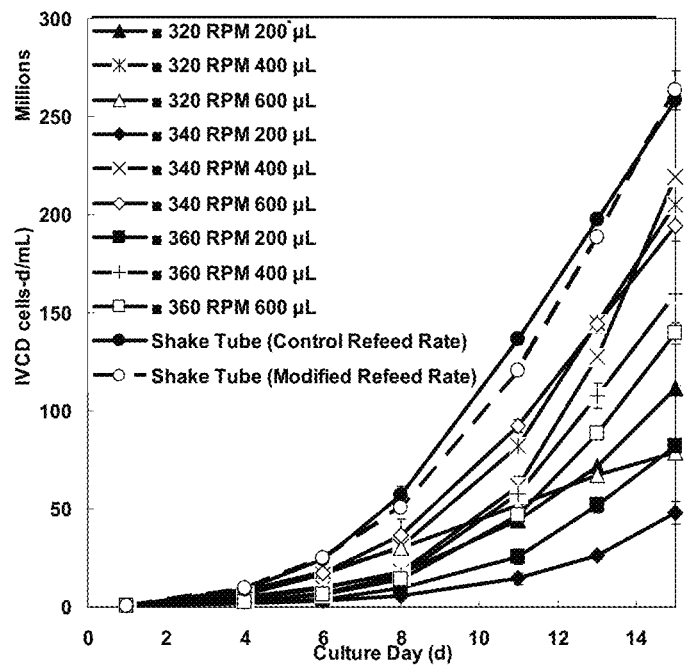
FIG. 18 is a graph of the integrated viable cell density of cells cultured in square-bottom 96-deep-well plates containing either 200 µL, 400 µL, or 600 µL CD CHO culture medium and agitated at 320 RPM, 340 RPM, or 360 RPM, or cells cultured in a shake tube (with media perfusion performed using the control refeed rate or the modified refeed rate). The error bars represent a standard deviation of n=2.

The viable cell density profiles of the 15-day cultures of cells maintained in CD CHO medium listed in Table 10 are shown in FIGS. 15 and 16. The round-bottom 96-deep-well plate cultures did not perform as well as the square-bottom cultures under the presently tested conditions (FIG. 15 and FIG. 16, respectively). The highest viable cell density reached in the round-bottom 96-deep well plates was $20\times10^6$ cells/mL for the 100 µL cultures agitated at 360 RPM. The square-bottom 96-deep-well plates cultures had comparable viable cell densities (within 1 standard deviation) (when the modified refeed rate described above was used) compared to the control shake tube cultures—with a peak viable cell density close to $40\times10^6$ cells/mL. The best square-bottom 96-deep well cell culture performance was achieved using a culture volume of 400 µL and an agitation of 320 RPM or 340 RPM, reaching a peak viable cell density of approximately $50\times10^6$ cells/mL on day 15. Moreover, the square-bottom 96-deep-well having a culture volume of 600 µL and agitation of 340 RPM resulted in cell growth up to $27\times10^6$ cells/mL on day 13 and produced comparable results to the shake tube control cultures (control refeed rate) that reached a peak viable cell density of $31\times10^6$ cells/mL. All the tested cultures maintained a percentage of viable cells greater than 85%. The comparison between the integrated viable cell density for the shake tube control cultures and the 96-deep-well cultures are shown in FIGS. 17 and 18.

Figure 19:
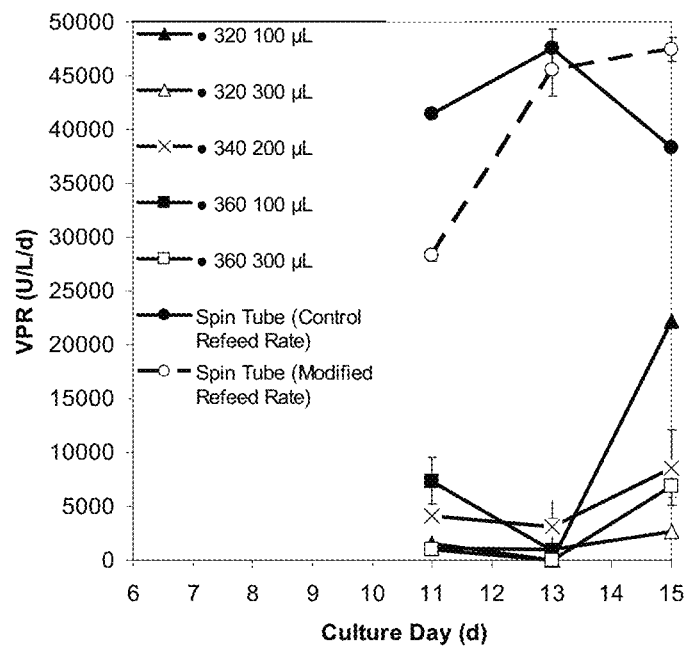
FIG. 19 is a graph of the volumetric productivity rate of cells cultured in round-bottom 96-deep-well plates containing either 100 µL, 200 µL, or 300 µL if CD CHO culture medium and agitated at 320 RPM, 340 RPM, or 360 RPM, or cells cultured in a shake tube (with media perfusion performed at the control refeed rate or the modified refeed rate). The error bars represent a standard deviation of n=2.
Figure 20:
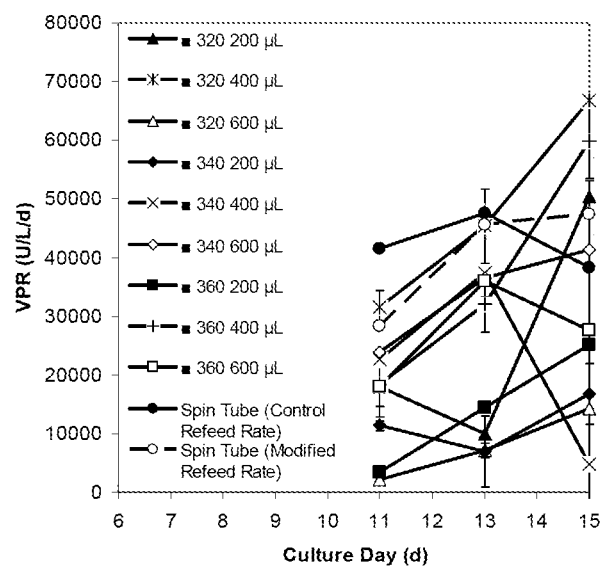
FIG. 20 is a graph of the volumetric productivity rate of cells cultured in square-bottom 96-deep-well plates containing either 200 µL, 400 µL, or 600 µL CD CHO culture medium and agitated at 320 RPM, 340 RPM, or 360 RPM, or cells cultured in a shake tube (with media perfusion performed at the control refeed rate or the modified refeed rate). The error bars represent a standard deviation of n=2.

The volumetric productivity rate profiles of the 15-day cultures of cells cultured in CD CHO are shown in FIGS. 19 and 20. As expected based on the viable cell growth, the cultures grown in the round-bottom 96-deep-well plates had less productivity (FIG. 19). The best volumetric productivity rate of 22,000 units/L/day was observed at day 15 in cultures grown in the round-bottom 96-deep-well plates in 100 µL culture medium and at an agitation of 320 RPM (FIG. 19). However, a round-bottom 96-deep-well plate culture having the same culture volume and agitation had a low volumetric productivity rate (<5000 units/L/day) for the days prior. Improved volumetric productivity rates were observed in the square-bottom 96-deep-well cultures (FIG. 20) which closely followed the growth profiles. Comparable activity (40000 units/L/day by day 15) was observed for the cultures whose growth patterns closely resembled the shake tube cultures (the square-bottom cultures having 600 µL volume and agitated at 340 RPM). Several cultures with an initial lag in growth, but ultimately with a similar peak viable cell density as the control shake tube cultures (square-bottom 96-deep-well cultures having a volume of 400 µL and an agitation of 340 RPM, or a volume of 400 µL or 600 µL and an agitation of 360 RPM) exhibited a similar volumetric productivity rate up to day 13 (reaching a volumetric productivity rate of approximately 40,000 units/L/day). After day 13, the volumetric productivity rate decreased except for cultures grown at a volume of 400 µL and agitated at 360 RPM, which reached a volumetric productivity rate of 60,000 units/L/day by day 15. The best productivity was observed in the square-bottom 96-deep-well cultures having a volume of 400 µL and agitated at 320 RPM, which reached a volumetric productivity rate of 67,000 units/L/day at day 15.

Figure 21:
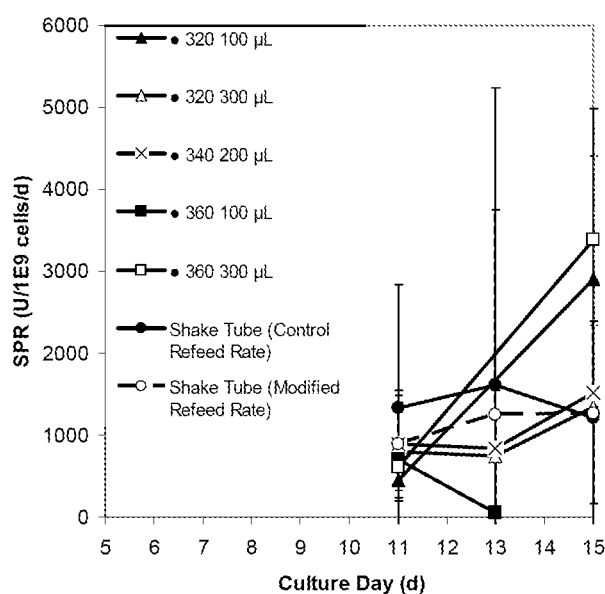
FIG. 21 is a graph of the specific productivity rate of cells cultured in round-bottom 96-deep-well plates containing either 100 µL, 200 µL, or 300 µL CD CHO culture medium and agitated at 320 RPM, 340 RPM, or 360 RPM, or cells cultured in a shake tube (with media perfusion performed at the control refeed rate or the modified refeed rate). The error bars represent a standard deviation of n=2.
Figure 22:
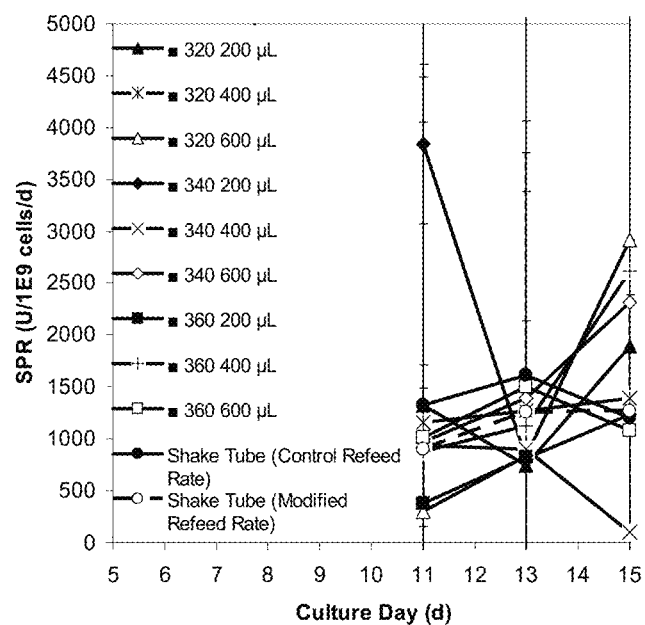
FIG. 22 is a graph of the specific productivity rate of cells cultivated in square-bottom 96-deep-well plates containing either 200 µL, 400 µL, or 600 µL CD CHO culture medium and agitated at 320 RPM, 340 RPM, or 360 RPM, or cells cultivated in a shake tube (with media perfusion performed at the control refeed rate or the modified refeed rate). The error bars represent a standard deviation of n=2.

Most conditions for the round-bottom 96-deep-well plate cultures exhibited comparable or lower specific productivity rates (SPR) as compared to the control shake tube cultures, with the exception of cultures grown in a volume of 100 µL and agitated at 320 RPM, or a volume of 300 µL and agitated at 360 RPM (FIG. 21). These cultures had increased specific productivity rate at day 15. The five square-bottom 96-deep-well plate cultures with comparable or greater volumetric productivity rate also exhibited a comparable or greater specific productivity rate as compared to the control shake tube cultures (1600 unites/$1\times10^9$ cells/day) (FIG. 22).

Figure 23:
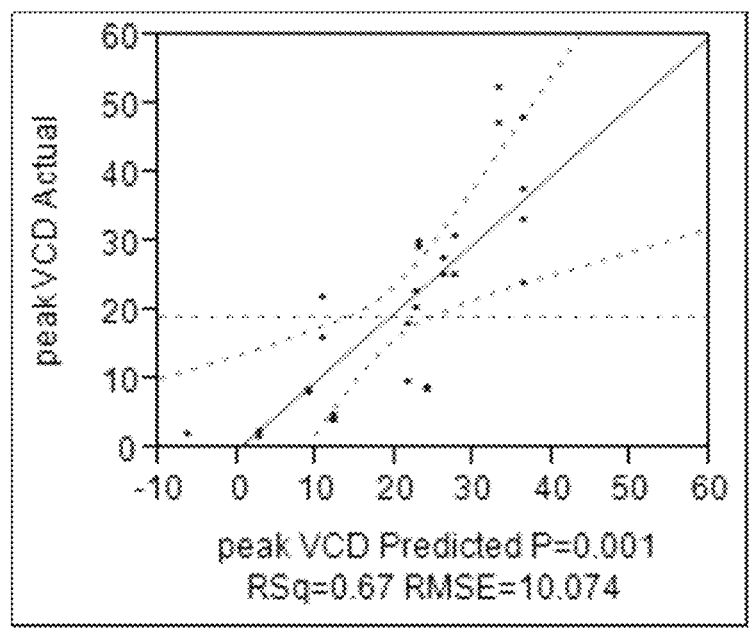
FIG. 23 is a graph of the fit of the real-time data to model predictions of viable cell density.
Figure 24:
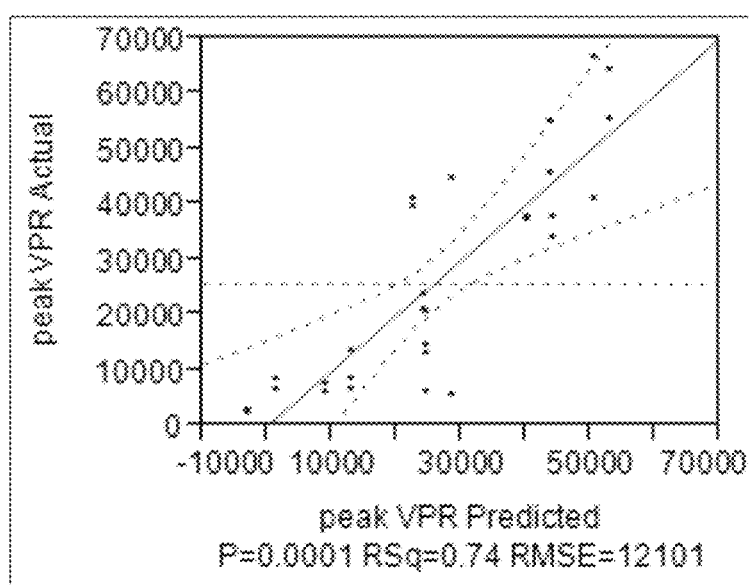
FIG. 24 is a graph of the fit of the real-time data to model predictions of volumetric productivity rate.

The collected data were fed into the JMP experimental design, to predict the best operating condition based on statistical analysis. The best operating condition was predicted using three responses: peak viable cell density, peak volumetric productivity rate, and peak specific productivity rate. All response limits were set to maximize the outcome. First, the data was fit to the model as shown in FIGS. 23 and 24. The data collected for viable cell density (FIG. 23) and volumetric productivity rate (FIG. 24) fit the model well. Statistical analysis (t-test) revealed that the well shape and working volume significantly affected both the viable cell density and productivity, whereas the shaking speed significantly affected the productivity only.

Figure 25:
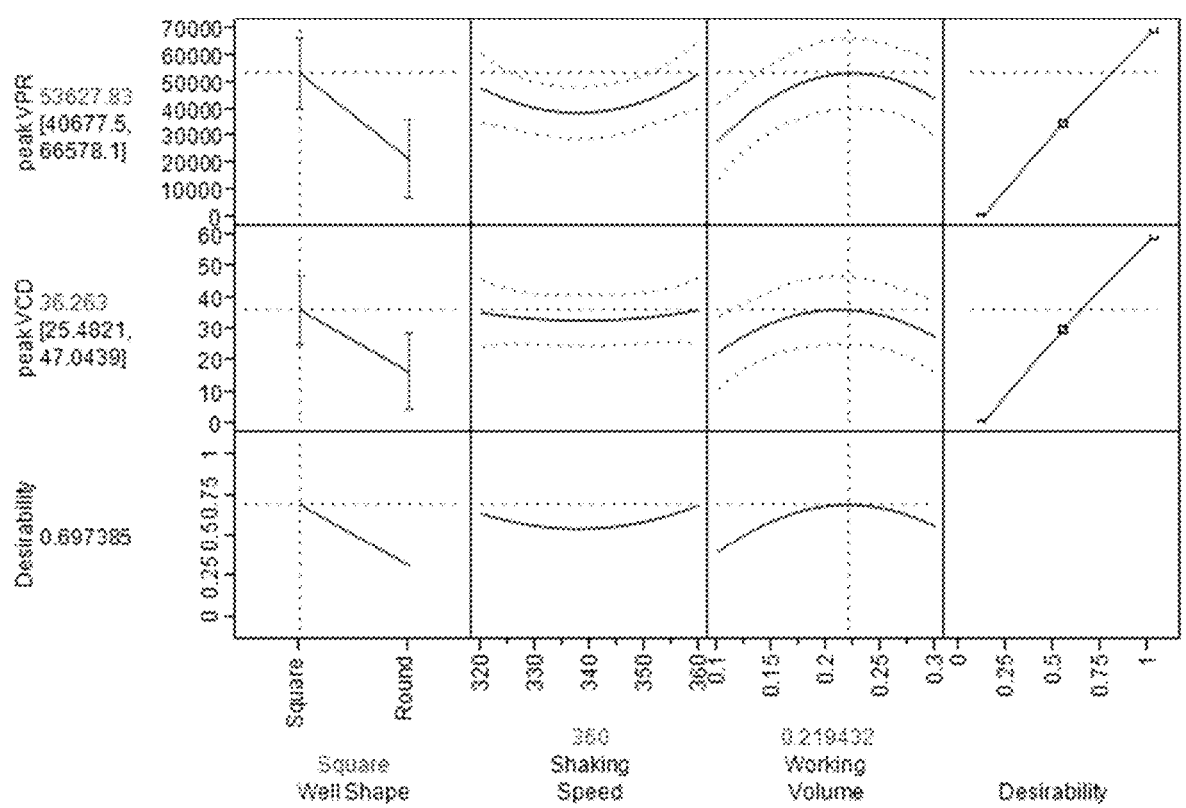
FIG. 25 is a set of twelve graphs showing the best operating conditions based on empirical data input into a statistical model taking into account standard deviations.
Figure 26:
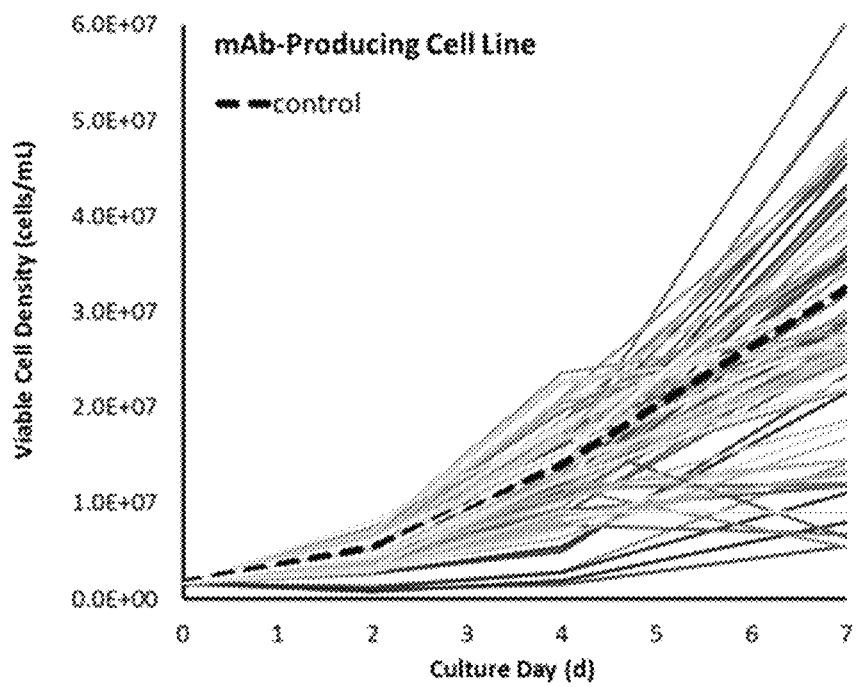
FIG. 26 is a graph of the viable cell density profile of a mammalian cell line producing a recombinant monoclonal antibody in 500 µL of one of a variety of different culture medium placed in a square-bottom 96-deep-well plate and agitated at a frequency of 330 RPM. The control data represent CD CHO medium.
Figure 27:
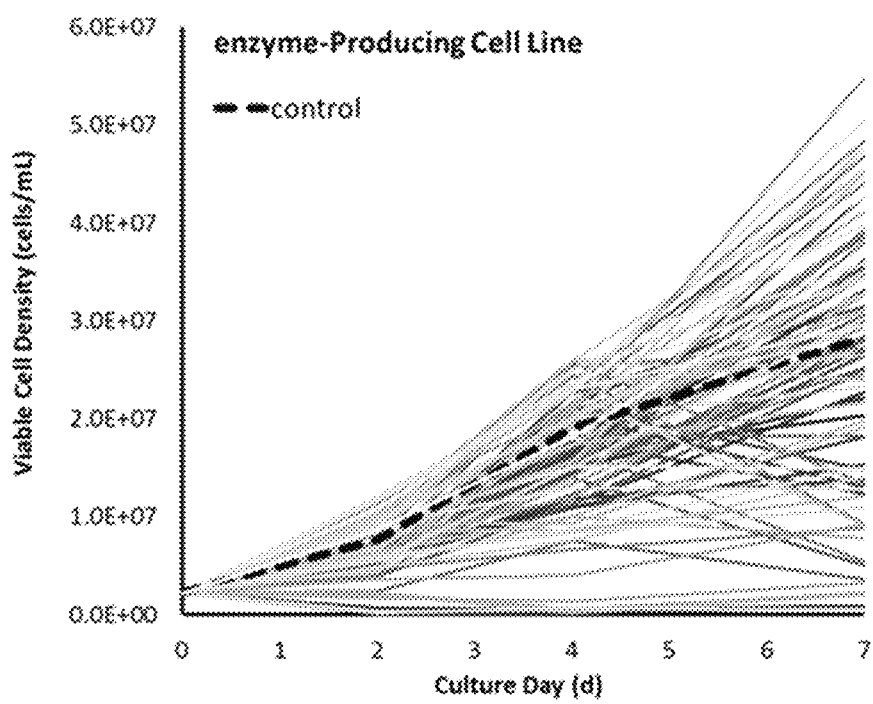
FIG. 27 is a graph of the viable cell density profile of a mammalian cell line producing a recombinant enzyme in a square-bottom 96-deep-well plate and agitated at a frequency of 330 RPM. The control data represent CD CHO medium.
Figure 28:
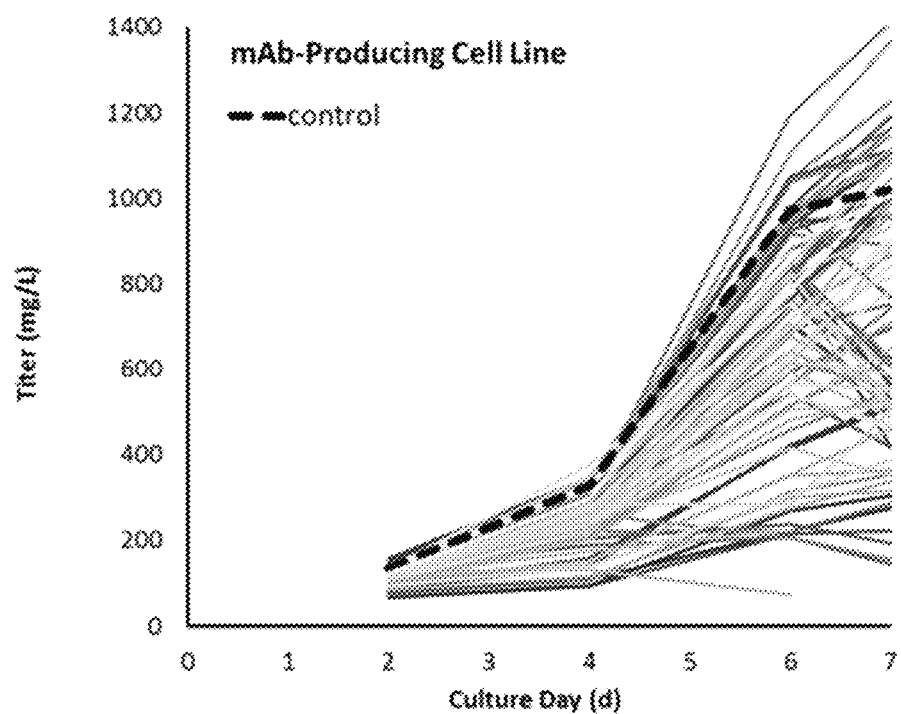
FIG. 28 is a graph of the titer (mg/mL) of a culture of a mammalian cell line producing a recombinant monoclonal antibody in 500 µL of one or a variety of different culture medium placed in a square-bottom 96-deep-well plate and agitated at a frequency of 330 RPM. The control data represent CD CHO medium.
Figure 29:
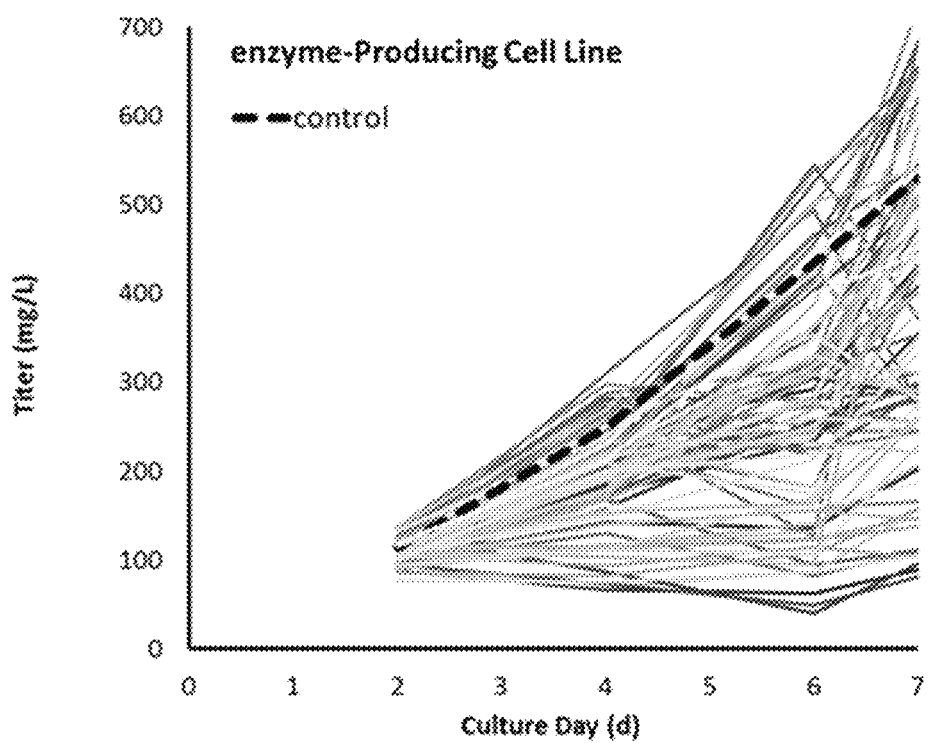
FIG. 29 is a graph of the titer (mg/mL) of a culture of a mammalian cell line producing a recombinant enzyme in 500 µL of one or a variety of different culture medium placed in a square-bottom 96-deep-well plate and agitated at a frequency of 330 RPM. The control data represent CD CHO medium.

The best operating conditions were predicted using the JMP profiler (FIG. 25). Based on the analysis, the best cell performance should be obtained when using square-bottom 96-deep-well plates with a working volume of 440 µL and agitated at 360 RPM. Taking into account the standard deviations and maintaining the same desirability, the best operating range for square-bottom 96-deep-well plates is a working volume is between about 350 µL and about 550 µL, and a shaking speed of between about 320 RPM and about 360 RPM.

In sum, the data show that the presently provided methods can be used as a model of larger scale perfusion bioreactor cell cultures (e.g., by achieving similar cell densities over a similar time frame). The presently provided methods can be used for high throughput screening of tissue culture media (and components within tissue culture media).

Example 2

Use of 96-Deep-Well Culturing Methods to Screen Culture Medium

A further set of experiments were performed to test a variety of different tissue culture medium using the 96-deepwell culturing methods described herein. In these experiments, a recombinant mammalian cell line producing a monoclonal antibody (mAb-producing cell) or a recombinant mammalian cell line producing an enzyme (enzyme-producing cell) was used to inoculate square-bottom 96-deep-well plates, and the cells were cultured for one week in 500 µL of one of at least 102 different tissue culture media with agitation at 330 RPM. The control in these experiments was the viable cell density achieved using the same 96-deep-well plate, the same culture medium, the sample cell line, and CD CHO medium. Both the viable cell density and the titer of the culture were measured over seven days.

The data in FIGS. 26-29 show that the 96-deep-well culturing methods described herein are capable of screening the effect of different tissue culture media on viable cell density and the productivity of the cultured cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of perfusion culturing a mammalian cell, the method comprising:
   providing a multi-well plate comprising at least one well comprising a mammalian cell disposed in a first liquid culture medium, wherein the first liquid culture medium occupies about 5% to about 70% of the volume of the well;
   incubating the multi-well plate for a period of time at about 31° C. to about 40° C. and with a rotary agitation of about 320 revolutions per minute (RPM) to about 380 RPM; and
   continuously, during the period of time, removing a first volume of the first liquid culture medium and adding to the first liquid culture medium a second volume of a second liquid culture medium,
   wherein:
   the first volume of the first liquid culture medium removed and the second volume of the second liquid culture medium added are about equal,
   the first volume of the first liquid culture medium is substantially free of mammalian cells, and
   the method results in a viable cell density of greater than $15 \times 10^6$ cells/mL.

2. The method of claim 1, wherein the mammalian cell contains a nucleic acid encoding a recombinant protein, and the method further comprises recovering the recombinant protein from the mammalian cell or from the first or second culture medium.

3. The method of claim 2, further detecting the recombinant protein in the mammalian cell or in the first or second liquid culture medium; and
   comparing the amount of recombinant protein present in the mammalian cell or in the first or second liquid culture medium to a reference level of recombinant protein.

4. The method of claim 3, wherein the reference level of recombinant protein is a level of recombinant protein produced using a different culturing method.

5. The method of claim 1, wherein the first volume of the first liquid culture medium removed and the second volume of the second liquid culture medium added are increased over time.

6. The method of claim 1, wherein:
   the multi-well plate is incubated for a period of time greater than 7 days, and on days 1 through 3 of incubation, in each 24-hour period, the first volume of the first liquid culture medium removed and the second volume of the second liquid culture medium added is between about 30% to about 50% of the volume of the first liquid culture medium;
   on days 4 through 6 of the incubation, in each 24-hour period, the first volume of the first liquid culture medium removed and the second volume of the second liquid culture medium added is between about 40% and about 70% of the volume of the first liquid culture medium; and
   on day 7 and onwards of incubation, in each 24-hour period, the first volume of the first liquid culture medium removed and the second volume of the second liquid culture medium added is about 90% to about 150% of the volume of the first liquid culture medium.

7. The method of claim 1, wherein the multi-well plate is a deep-well plate.

8. The method of claim 1, wherein:
   the diameter of the bottom of the well is between about 6.0 mm and about 35 mm;
   the height of the wall is about 12 mm to about 50 mm; or
   the well has a volume of about 1 mL to about 18 mL.

9. The method of claim 1, wherein the mammalian cell is suspended in about 150 µL to about 15 mL of the first culture medium.

10. The method of claim 1, wherein after about the first 24 to 48 hours of the period of time, in each 24-hour period, the first volume of the first liquid culture medium removed and the second volume of the second liquid culture medium added is about 30% to about 150% of the volume of the first liquid culture medium.

11. The method of claim 1, wherein the multi-well plate is sealed with a gas-permeable disposable membrane or a gas-permeable silicone layer.

12. The method of claim 1, wherein the well has a flat bottom or a round bottom.

13. The method of claim 1, wherein the rotary agitation is about 320 RPM to about 360 RPM.

14. The method of claim 1, wherein the method results in a viable cell density of greater than $15 \times 10^6$ cells/mL at 8 days or more after the beginning of the period of time.

15. The method of claim 1, wherein the method results in a viable cell density of greater than $20 \times 10^6$ cells/mL.

16. The method of claim 15, wherein the method results in a viable cell density of greater than $20 \times 10^6$ cells/mL at 8 days or more after the beginning of the period of time.

17. The method of claim 1, wherein the method results in a viable cell density of greater than $25 \times 10^6$ cells/mL.

18. The method of claim 17, wherein the method results in a viable cell density of greater than $25 \times 10^6$ cells/mL at 8 days or more after the beginning of the period of time.

* * * * *